US008597919B2

(12) United States Patent
Lewis

(10) Patent No.: US 8,597,919 B2
(45) Date of Patent: *Dec. 3, 2013

(54) METHODS AND SYSTEMS FOR PRODUCING ETHANOL USING RAW STARCH AND SELECTING PLANT MATERIAL

(75) Inventor: Stephen M. Lewis, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/043,345

(22) Filed: Mar. 8, 2011

(65) Prior Publication Data

US 2011/0250312 A1    Oct. 13, 2011

Related U.S. Application Data

(63) Continuation of application No. 11/546,522, filed on Oct. 10, 2006, now Pat. No. 7,919,289.

(60) Provisional application No. 60/725,465, filed on Oct. 10, 2005.

(51) Int. Cl.
| C12C 7/04 | (2006.01) |
| C12P 7/06 | (2006.01) |
| C12P 19/20 | (2006.01) |
| C12N 9/26 | (2006.01) |
| C12Q 1/40 | (2006.01) |
| C12Q 1/34 | (2006.01) |
| C12C 1/00 | (2006.01) |
| C12P 19/04 | (2006.01) |

(52) U.S. Cl.
USPC ............ 435/161; 426/11; 435/18; 435/22; 435/93; 435/96; 435/105; 435/201

(58) Field of Classification Search
USPC ............ 435/18, 22, 93, 96, 105, 161, 201
See application file for complete search history.

(56) References Cited

U.S. PATENT DOCUMENTS

| 2,440,925 A | 5/1948 | Boeckeler |
| 3,940,492 A | 2/1976 | Ehnstrom |
| 4,009,074 A | 2/1977 | Walon |
| 4,092,434 A | 5/1978 | Yoshizumi et al. |
| 4,243,750 A | 1/1981 | Muller et al. |
| 4,279,747 A | 7/1981 | Chen |
| 4,287,303 A | 9/1981 | Dahlberg et al. |
| 4,309,254 A | 1/1982 | Dahlstrom et al. |
| 4,316,956 A | 2/1982 | Lutzen |
| 4,358,536 A | 11/1982 | Thorsson et al. |
| 4,361,651 A | 11/1982 | Keim |
| 4,376,163 A | 3/1983 | Ehnstrom |
| 4,460,687 A | 7/1984 | Ehnstrom |
| 4,474,883 A | 10/1984 | Yamamoto et al. |
| 4,490,469 A | 12/1984 | Kirby et al. |
| 4,514,496 A | 4/1985 | Yoshizumi et al. |
| 4,522,920 A | 6/1985 | Thorsson et al. |
| 4,540,663 A | 9/1985 | Witt |
| 4,591,560 A | 5/1986 | Kainuma et al. |
| 4,618,579 A | 10/1986 | Dwiggins et al. |
| 4,716,218 A | 12/1987 | Chen et al. |
| 4,727,026 A | 2/1988 | Sawada et al. |
| 4,760,025 A | 7/1988 | Estell et al. |
| 4,863,864 A | 9/1989 | Ashikari et al. |
| 4,876,196 A | 10/1989 | Salzbrunn et al. |
| 4,933,279 A | 6/1990 | Carroll et al. |
| 5,061,497 A | 10/1991 | Thacker et al. |
| 5,084,385 A | 1/1992 | Ashikari et al. |
| 5,087,417 A | 2/1992 | Dumbroff et al. |
| 5,177,008 A | 1/1993 | Kampen |
| 5,177,009 A | 1/1993 | Kampen |
| 5,180,669 A | 1/1993 | Antrim |
| 5,231,017 A | 7/1993 | Lantero et al. |
| 5,250,182 A | 10/1993 | Bento et al. |
| 5,260,089 A | 11/1993 | Thornberg |
| RE34,606 E | 5/1994 | Estell et al. |
| 5,322,778 A | 6/1994 | Antrim et al. |
| 5,364,770 A | 11/1994 | Berka et al. |
| 5,545,543 A | 8/1996 | Zinnamosca et al. |
| 5,559,031 A | 9/1996 | Zinnamosca et al. |
| 5,652,127 A | 7/1997 | Mitchinson et al. |
| 5,688,674 A | 11/1997 | Choi et al. |

(Continued)

FOREIGN PATENT DOCUMENTS

| CA | 1143677 | 3/1983 |
| DE | 267508 | 5/1989 |
| EP | 0138428 | 4/1985 |
| EP | 0 140 410 | 5/1985 |
| EP | 0 171 218 | 2/1986 |
| GB | 2089836 | 6/1982 |
| JP | 58-005145 | 1/1983 |
| JP | 59-179093 | 10/1984 |
| RU | 2001103 | 10/1993 |
| RU | 2127760 | 3/1999 |

(Continued)

OTHER PUBLICATIONS

Maier et al. 1992. Grain Quality Fact Sheet #5. Low-Temperature Drying of the 1992 Indiana Corn Crop. Purdue University, Cooperative Extension Service, West Lafayette, Indiana, pp. 1-8, http://www.extension.purdue.edu/extmedia/GQ/GQ-5.html printed Dec. 15, 2012.*

U.S. Appl. No. 12/716,989, filed Mar. 3, 2010, Kwiatkowski.

Abouzied, et al., Direct fermentation of potato starch to ethanol by cocultures of *Aspergillus niger* and *Saccharomyces cerevisiae*, Appl Environ Microbiol, 1986, 52(5):1055-9.

(Continued)

*Primary Examiner* — Jon P Weber
*Assistant Examiner* — Kailash C Srivastava
(74) *Attorney, Agent, or Firm* — Foley & Lardner LLP

(57) ABSTRACT

The present invention relates to methods for producing high levels of alcohol during fermentation of plant material, and to the high alcohol beer produced. The method can include selecting plant material. Selecting can include excluding plant material that has been exposed to high temperatures or that has had high moisture content.

7 Claims, 29 Drawing Sheets

(56) References Cited

U.S. PATENT DOCUMENTS

| | | | |
|---|---|---|---|
| 5,721,127 | A | 2/1998 | Deweer et al. |
| 5,721,128 | A | 2/1998 | Deweer et al. |
| 5,736,375 | A | 4/1998 | Deweer et al. |
| 5,736,499 | A | 4/1998 | Mitchinson et al. |
| 5,756,714 | A | 5/1998 | Antrim et al. |
| 5,817,498 | A | 10/1998 | Deweer et al. |
| 5,824,532 | A | 10/1998 | Barnett et al. |
| 5,849,549 | A | 12/1998 | Barnett et al. |
| 5,958,739 | A | 9/1999 | Mitchinson et al. |
| 5,981,237 | A | 11/1999 | Meagher et al. |
| 6,074,854 | A | 6/2000 | Deweer et al. |
| 6,136,576 | A | 10/2000 | Diaz-Torres et al. |
| 6,171,817 | B1 | 1/2001 | Berka et al. |
| 6,228,177 | B1 | 5/2001 | Torget |
| 6,313,328 | B1 | 11/2001 | Ulrich et al. |
| 6,423,145 | B1 | 7/2002 | Nguyen et al. |
| 6,451,063 | B1 | 9/2002 | Clarkson et al. |
| 6,509,180 | B1 | 1/2003 | Verser et al. |
| 6,538,182 | B1 | 3/2003 | Thompson et al. |
| 6,616,948 | B2 | 9/2003 | Gustavsson et al. |
| 6,664,095 | B1 | 12/2003 | Suryanarayan et al. |
| 6,709,527 | B1 | 3/2004 | Fechter et al. |
| 6,774,284 | B1 | 8/2004 | Thompson et al. |
| 6,803,218 | B1 | 10/2004 | Seyfried et al. |
| 6,849,439 | B2 | 2/2005 | Henson et al. |
| 6,849,782 | B2 | 2/2005 | Thompson et al. |
| 6,855,529 | B2 | 2/2005 | Thompson et al. |
| 6,867,237 | B1 | 3/2005 | Taylor et al. |
| 6,878,860 | B1 | 4/2005 | Thompson et al. |
| 7,344,876 | B2 | 3/2008 | Levine |
| 7,579,177 | B2 | 8/2009 | Olsen et al. |
| 7,622,284 | B2 | 11/2009 | Op Den Camp et al. |
| 7,919,291 | B2 * | 4/2011 | Lewis et al. ............ 435/161 |
| 2003/0134395 | A1 | 7/2003 | Shetty et al. |
| 2003/0134396 | A1 | 7/2003 | Shetty et al. |
| 2003/0180900 | A1 | 9/2003 | Lanteo |
| 2003/0203454 | A1 | 10/2003 | Chotani et al. |
| 2004/0023349 | A1 | 2/2004 | Bisgaard-Frantzen et al. |
| 2004/0043117 | A1 | 3/2004 | Cope et al. |
| 2004/0063184 | A1 | 4/2004 | Grichko |
| 2004/0080923 | A1 | 4/2004 | Janisch |
| 2004/0091983 | A1 | 5/2004 | Veit et al. |
| 2004/0115779 | A1 | 6/2004 | Olsen et al. |
| 2004/0157301 | A1 | 8/2004 | Chotani et al. |
| 2004/0192896 | A1 | 9/2004 | Finch |
| 2004/0197409 | A1 | 10/2004 | Iyer et al. |
| 2004/0219649 | A1 | 11/2004 | Olsen et al. |
| 2004/0234649 | A1 | 11/2004 | Lewis et al. |
| 2005/0026261 | A1 | 2/2005 | Otto et al. |
| 2005/0042737 | A1 | 2/2005 | Vikso-Nielsen et al. |
| 2005/0100996 | A1 | 5/2005 | Lantero, Jr. et al. |
| 2005/0136525 | A1 | 6/2005 | Baldwin et al. |
| 2005/0208623 | A1 | 9/2005 | Baldwin et al. |
| 2005/0233030 | A1 | 10/2005 | Lewis et al. |
| 2005/0239181 | A1 | 10/2005 | Lewis et al. |
| 2006/0051847 | A1 | 3/2006 | Gunnarsson et al. |
| 2006/0246563 | A1 | 11/2006 | Eroma et al. |
| 2007/0178567 | A1 | 8/2007 | Lewis |
| 2007/0196907 | A1 | 8/2007 | Lewis |
| 2007/0202214 | A1 | 8/2007 | Lewis et al. |
| 2008/0032373 | A1 | 2/2008 | Bhargava |
| 2009/0053793 | A1 | 2/2009 | Lefebvre et al. |
| 2010/0041116 | A1 * | 2/2010 | Lewis et al. ............ 435/161 |
| 2010/0151549 | A1 | 6/2010 | Bhargava |
| 2010/0196980 | A1 | 8/2010 | Smith et al. |
| 2010/0227369 | A1 | 9/2010 | Narendranath |
| 2010/0233771 | A1 | 9/2010 | McDonald |
| 2011/0070618 | A1 | 3/2011 | Lewis et al. |
| 2011/0097446 | A1 | 4/2011 | Lewis |
| 2011/0111085 | A1 | 5/2011 | Lewis et al. |

FOREIGN PATENT DOCUMENTS

| | | |
|---|---|---|
| WO | WO 91/03543 | 3/1991 |
| WO | WO 92/20777 | 11/1992 |
| WO | WO 95/13362 | 5/1995 |
| WO | WO 97/27047 | 7/1997 |
| WO | WO 02/38787 | 5/2002 |
| WO | WO 02/074895 | 9/2002 |
| WO | WO 03/018766 | 3/2003 |
| WO | WO 03/062430 | 7/2003 |
| WO | WO03/066816 | 8/2003 |
| WO | WO 03/066826 | 8/2003 |
| WO | WO 03/068976 | 8/2003 |
| WO | WO 2004/080923 A2 | 9/2004 |
| WO | WO 2004/081193 | 9/2004 |
| WO | WO 2004/106533 A1 | 12/2004 |
| WO | WO 2005/052148 | 6/2005 |
| WO | WO 2005/082155 | 9/2005 |

OTHER PUBLICATIONS

Aden et al., 2002. Lignocellutolsic Biomass to Ethanol Process Design and Economics Utilizing Co-Current Dilute Acid Prehydrolysis and Enzymatic Hydrolysis for Corn Stover. NREL Report, pp. 1-88 and Appendices A-I.

Aldrich. "New Enzymes Lower Ethanol Production Fuel Costs", BridgeNews. Kansas City. Apr. 4, 2004.

Allison et al., "Transformation of the thermophilic fungus *Humicola grisea* var. thermoidea and overproduction of Humicola glucoamylase", Curr Genet (1992) 21:225-229.

Argus Leader.Com., Web Page—Business—Broin Goes to Court, Printed Jun. 27, 2006, pp. 1-3.

Ashikari et al., "Rhizopus Raw-Starch-Degrading Glucoamylase: Its Cloning and Expression in Yeast". Agric. Bio. Chem. 50(4), 957-964 (1986).

Author Unknown "Alcohol and Alcohol Derivative" (Internet Mar. 2003).

Author Unknown "Chapter 1. Review of the Literature—Coproducts and Near Coproducts of Fuel Ethanol Fermentation from Grain", *Agriculture and Agri-Food Canada Research Branch* (Internet Mar. 2003).

Author Unknown "Determination of acid or-Amylase activity, FIA", SOP No. EB-SM-0259.01/01 pp. 1-14 (Internet Mar. 2003).

Author Unknown "Determination of Amyloglucosidase Activity using the Auto Analyzer", Novozymes Analytical Method EB-SM-0131.02/01 (Internet Mar. 2003).

Author Unknown "Enzymatic modification of starch granules: peeling off versus porosity", TNO Nutrition and Food Research, Dec. 28, 2000, pp. 1-2.

Author Unknown "Grain Processing Enzymes for Sweetener Production", Genencor International. Apr. 2004, pp. 1-3,.

Author Unknown "Novelose" Resistant Starch—The starch that thinks it's a fiber, National Starch and Chemical Compnay, 2003.

Author Unknown "Nutrient composliton of DDGS (100% dry matter basis) from various reference—Table 1", Distillers Grains Quarterly, First Quarter 2006, pp. 27-28.

Author Unknown "Ready for Research", BioFuels Journal, pp. 20-23 (4Q04). cited by other Bothast, "Ethanol research facility one of a kind", Industrial Oil Products Article, vol. 15(8):518-519 (Aug. 2004).

Author Unknown "SIU Edwardsville National Corn to Ethanol Research Pilot Plant Process Description", Project No. 24307-78188, Washington group Nov. 12, 2001.

Author Unknown "Spirizyme Plus for ethanol production", Novozymes Application Sheet Ethano1/2002-03379-03.pdf (Internet Mar. 2003).

Author Unknown "Very High Gravity Technology", Ethanol Producer Magazine, Jan. 2006.

Bardini, G. et al., "Continuous clarification of grape must by flotation," Vini d'italia, vol. 34. No. 1 pp. 31-38 (1992)(1 page Abstract).

Belya et al., "Composition of corn and distillers dried grains with solubles from dry grind ethanol processing", Bioresource Technology 94 (2004) 293-298.

(56) References Cited

OTHER PUBLICATIONS

Berven, "The Making of Broin Project X", Ethanol Producer Magazine, Feb. 2005, pp. 66-71.
Biotimes: The enzyme e-zine, "Fuel Ethanol Products" (Jan. 2003).
Biswas et al., "Analysis of Headspace Compounds of Distillers Grains using SPME in Conjunction with GC/MS and TGA", Journal of Cereal Science, 33(2001) 223-229.
Boel et al., "Glucoamylases G1 and G2 from *Aspergillus niger* are synthesized from two different but closely related mRNAs", The EMBP Journal, vol. 3, No. 5, pp. 1097-1102 (1984).
Bothast, "Ethanol research facility one of a kind," Industrial Oil Products Article, vol. 15(8):518-519 (Aug. 2004).
Brown et al., "The effect of temperature on the ethanol tolerance of the yeast, *Saccharomyces uvarum*", Biotechnology Letters, vol. 4, 269-274 (1982).
Bryan, "Changing the Game", Ethanol Producer Magazine, pp. 58-63 (Aug. 2005).
Carlson, M., "Distillers ByProducts for Swine Diets", Missouri Value Added Development Center (Internet Mar. 2003).
Casey et al., "Reevaluation of Alcohol Synthesis and Tolerance on Brewer's Yeast", American Society of Brewing Chemists, Inc., vol. 43, No. 2, pp. 75-83 (1985).
Chen et al., "Comparison of four different chemical pretreatments of corn stover for enhancing enzymatic digestibility." Biomass and Bioenergy, vol. 33, Jun. 26, 2009, pp. 1381-1385.
Chen et al., "Effect of replacing helical glycine residues with alanines on reversible and irreversible stability and production of *Aspergillus awamori* glucoamylase", Protein Engineering, vol. 9, No. 6, pp. 499-505 (1996).
Chi Z.M.; Liu Z. R., "High-concentration alcoholic production from hydrolysate of raw ground corn by a tetraploid yeast strain" Biotechnology Letters, vol. 15, No. 8 Aug. 31, 1993, pp. 877-882.
Civil Docket Sheet for Case No. 04-cv-4202 printed Jun. 23, 2006.
International Search Report dated Jun. 1, 2005.
International Search Report mailed Dec. 9, 2005.
PCT2005US008155 Internation Search Report Dated Nov. 30, 2005 and Written Opinion.
Daugulis et al., "The Economics of Ethanol Production by Extractive Fermentation", The Canadian J. of Chemical Engineering, vol. 69, pp. 488-497 (Apr. 1991).
Dettori-Campus et al., "Hydrolysis of Starch Granules by the Amyase from *Bacillus stearothermophilus* NCA 26", Process Biochemistry, 27 (1992) 17-21.
District Court Civil Docket No. 1: Complaint, filed by Broin and Associates, Inc., Entered: Dec. 15, 2004.
District Court Civil Docket No. 102: Genencor's Notice to Take Deposition of Novozymes North America, Inc., Entered May 2, 2005.
District Court Civil Docket No. 112: Transcript of Proceedings held on Mar. 4, 2005 regarding Docket No. 69, motion Hearing, Entered: May 13, 2005.
District Court Civil Docket No. 132: Memorandum Opinion and Order regarding Docket No. 54, denying in part Motion to Dismiss as to Counts III, IV, V, and VIII and granting without prejudice to Plaintiff's right to amend as to Counts VI and VII, denying Docket No. 54, Motion for a more Definite Statement Signed by Judge Lawrence L. Piersol on Jul. 26, 2005, Entered: Jul. 26, 2005.
District Court Civil Docket No. 138: Genencor International, Inc.'s Answer to Amended Complaint and Counterclaim against Broin and Associates, Inc., by Genencor International, inc. Entered: Aug. 29, 2005.
District Court Civil Docket No. 148: Reply to Docket No. 138, Answer to Amended Complaint and Counterclaim against filed by Broin and Associates, Inc., Bronin and Associates, Inc. Entered: Sep. 20, 2005.
District Court Civil Docket No. 15-1: First Amended Complaint, filed by Broin and Associates, Inc. (Attachments: #1 Exhibit A—PRess Release #2 Exhibit B—Magazine Article), Entered Jan. 25, 2005.
District Court Civil Docket No. 15-2: Press Release dated Nov. 4, 2004, Broin Companies Announces Ethanol Technology Revolution.
District Court Civil Docket No. 153: Memorandum in Support regarding Docket No. 152, Motion to dismiss First Amended Complaint Based on Interntional Violations of Protective Order filed by Genencor International, Inc. (Sanford, Steven) (Entered: Sep. 30, 2005).
District Court Civil Docket No. 16: First Motion to Expedite Discovery and Supporting Brief by Broin and Associates, Inc., Entered: Jan. 25, 2005.
District Court Civil Docket No. 17-1: Declaration of Jeffrey C. Brown regarding (16) First Motion to Expedite Discovery and Supporting Brief, Entered: Jan. 25, 2005.
District Court Civil Docket No. 17-6: Exhibit E of Docket No. 17, Plaintiff's First Set of Interrogatories to Defendant, Entered: Jan. 25, 2005.
District Court Civil Docket No. 50-1: Affidavit of Steven W. Sanford in Support of Defendant Genencor's Opposition to Motion for Summary Judgment, Entered Feb. 14, 2005.
District Court Civil Docket No. 50-6: Exhibit D of Docket No. 50, Jan. 10, 2005 letter from Mark Skoog to Ben Brown, Entered: Feb. 14, 2005.
District Court Civil Docket No. 52: Memorandum in Opposition regarding Docket No. 16, First Motion to Expedite Discovery and Supporting Brief, filed by Genencor International, Inc., Entered: Feb. 14, 2005.
District Court Civil Docket No. 53: Motion for Discovery, Requiring Plaintiff to Specify Trade Secrets Prior to Commencement of Discovery and Supporting Brief, b y Genencor International, Inc. Entered: Feb. 14, 2005.
District Court Civil Docket No. 54: Motion to Dismiss Pursuant to FRCP 12(b)(6): Motion for a More Definite Statement Pursuant to FRCP 12(e) and Supporting Brief, by Genencor International, Inc. Entered: Feb. 14, 2005.
District Court Civil Docket No. 61: Response to Motion regarding Docket No. 53, Motion for Discovery, Requiring Plaintiff to Specify Trade Secrets Prior to Commencement of Discovery and Supporting Brief, filed by Broin and Associates, Inc., Entered: Feb. 28, 2005.
District Court Civil Docket No. 62: Reply to Motion Response regarding Docket No. 16, First Motion to Expedite Discovery and Supporting Brief, filed by Broin and Associates, Inc., Entered: Mar. 1, 2005.
District Court Civil Docket No. 67, Reply to Motion Response regarding Docket No. 53, Motion for Discovery, Requiring Plaintiff to Specify Trade Secrets Prior to Commencement of Discovery and Supporting Brief, filed by Genencor International, Inc. Entered: Mar. 2, 2005.
District Court Civil Docket No. 68: Form 35 Report of parties Planning Meeting and Scheduling Information, Entered: Mar. 2, 2005.
District Court Civil Docket No. 77, Memorandum in Opposition regarding Docket No. 54, Motion to Dismiss Pursuant to FRCP 12(b)(6): Motion for a More Definite Statement Pursuant to FRCP 12(e) and Supporting Brief, filed by Broin and Associates, inc. Entered: Mar. 9, 2005.
District Court Civil Docket No. 85: Reply to Motion Response regarding Docket No. 54, Motion to Dismiss Pursuant to FRCP 12(b0(6); Motion for a More Definite Statement Pursuant to FRCP 12(e) and Supporting Brief, filed by Genencor International, Inc., Entered: Mar. 23, 2005.
District Court Civil Docket No. 90: Response to Docket No. 87 Brief, Regarding Genencor's Objections to Broin's Identification of Trade Secrets, filed by Broin and Associates, inc., Entered: Apr. 11, 2005.
District Court Civil Docket No. 95: Form 35 Report of Parties Planning Meeting and Scheduling information, Entered: Apr. 18, 2005.
Dong, F.M. et al., "The Neutral Detergent Fiber, Acid Detergent Fiber, Crude Fiber, and Lignin Contents of Distillers' Dried Grains with Solubles," Journal of Food Science, vol. 52, No. 2, pp. 403-405, 1987.
Donohoe et al., "Detecting cellulase penetration into corn stover cell walls by immuno-electron microscopy." Biotechnology and Bioengineering, vol. 103, Feb. 11, 2009, pp. 480-489.
Dunn-Coleman et al., "Production of granular starch hydrolyzing enzymes for low energy grain ethanol production", 27th Symposium on Biotechnology for Fuels and Chemicals, Genencor Presentation (May 2005).

(56) References Cited

OTHER PUBLICATIONS

Elander et al., "Summary of findings from the Biomass Refining Consortium for Applied Fundamentals and Innovation (CAFI): corn stover pretreatment" Cellulose, vol. 16, Jun. 26, 2009, pp. 649-659.
Farid, M. et al., "Alcohol production from starch by mixed cultures of *Aspergillus awamori* and immobilized *Saccharomyces cervisiae* a different agitation speeds", J. Basic Microbio, 42(3):162-71 (2002) (Abstract only).
Form PCT/ISA/206 and Annex to Form PCT/ISA/206, invitation to Pay Additional Fees and Partial International Search for International Patent Application PCT/US2006/017041, dated Sep. 15, 2006.
Form PCT/ISA/220, International Search Report and Written Opinion of International Patent Application PCT/US2005/008156, dated Mar. 7, 2006.
Fox, B. (1997) in Fermentation and Biochemical Engineering Handbook Principles, Process Design; and Equipment, Second Edition, Vogel et al (eds.). Novea Publications, WasWood, Nlw Icrs V-07675, p. 734-758.
Fujio et al,, "Alcohol Fermentation of Raw Cassava Starch by *Rhizopus koji* without cooking." Biotechnology and Bioengineering, vol. XXVI, p. 315-319, 1984.
Fujio et al., "Ethanol Fermentation of Raw Cassava Starch with *Rhizopus koji* in a Gas Circulation Type Fermentor", Biotechnology and Bioengineering, vol. 27:1270-1273, Aug. 1985.
GCOR Lantero patent application search USPTO site.5.17.05.
Genencor Inventor Search, Oct. 3, 2005.
Hamdy et al., "Effects of virginiamycin on Fermentation Rate by Yeast", Biomass and Bioenergy, vol. 11, No. 1 pp. 1-9 (1996).
Hamelinck et al. "Ethanol from lignocellulosic biomass: techno-economic performance in short-, middle- and long term" Biomass and Bioenergy, vol. 28, 2005, pp. 384-410.
Han et al. (1987). Amylolysis of Raw Corn by *Aspergillus niger* for Simultaneous Ethanol Fermentation. Biotechnology and Bioengineering, vol. 30, pp. 225-232.
Han, M. et al., "Saccharification and Ethanol Fermentation from Uncooked Starch Using *Aspergillus niger* Koji," Korean J. Food Sci. Technol., vol. 17, No. 4,pp. 258-264 91985).
Hayashida et al., "High Concentration-Ethanol Fermentation of Raw Ground Corn", Agric. Biol. Chem., 46(7), 1947-1950 (1982).
Hayashida et al., "Molecular cloning of Glucoamylase 1 Gene of *Aspergillus awamori* var. kawachi for Localization of the Raw-starch-affinity Site", Argic. Biol. Chem., 53(4), 923-929 (1989).
Hayashida et al., Raw Starch-digestive Glucoamulase Productivity of Protease-less Mutant from *Asoergukkys awaniru* var. kawachi, Agric. Biol. Chem., 45(12)m p. 2675-2681, 1981.
Honeyman et al., "Evaluation of a Distillers Dried Grain Derivative Feedstuff on Performance of Nursery Pigs", Iowa State University (Internet Mar. 2003).
Islam et al., "Stability of virginiamycin and penicillin during alcohol fermentation", Biomass and Bioenergy, 17: 369-376 (1999).
Iwata et al. "Purification and Characterization of Rice. Alpha.-glucosidase, a key enzyme for Alcohol Fermentation of Rice Polish" Journal of Bioscience and Bioengineering. vol. 95, issue 1, p. 106-108, 2003.
Jacques et al., The Alcohol Textbook, 3rd Edition, A reference for the beverage, fuel and industrial alcohol industries, Nottingham University Press 1999, Alltech Inc. 1999 (386 pages).
Jacques et al., The Alcohol Textbook, 4th Edition, A reference for the beverage, fuel and industrial alcohol industries, Nottingham University Press 2003 Alltech Inc.(446 pages), 2003.
Jensen et al., "Purification of extracellular amylolytic enzymes from the thermophilic fungus *Thermornyces lanuginosus*", Can. J. Microbiol., vol. 34, 218-223 (1988).
Jones, "review: Biological principles for the effects of ethanol", Enzyme Microb. Technol., vol. 11, pp. 130-153 (Mar. 1989).
Joutsjoki et al., "A Novel Glucoamylase Preparation for Grain Mash Saccharification", Biotechnology Letters, vol. 15, No. 3, pp. 227-282 (Mar. 1993).

Kang, H. et al., "Effect of Initiation Factor eIF-5A Depletion on Protein Synthesis and Proliferation of *Saccharomyces cerevisiae*," J. Biol. Chem., vol. 269, No. 6, pp. 3934-3940 (Feb. 11, 1994).
Knott et al. "Effects of the Nutrient Variability of Distiller's Solubles and Grains within Ethanol Plants and the Amount of Distiller's Solubles Blended with Distiller's Grains on Fat, Protein and Phosphorus Content of DDGS." 2004.
Knott et al. "Variation in Particle Size and Bulk Density of Distiller's Dried Grains with Solubles (DDGS) Produced by 'New Generation' Ethanol Plants in Minnesota and South Dakota." 2004.
Kuyper et al., "Evolutionary engineering of mixed-sugar utilization by a xylose-fermenting *Saccharomyces cerevisiae* strain" Fems Yeast Research, vol. 5, 2005, pp. 925-934.
Lang et al., "Recycle Bioreactor for Bioethanol Production from Wheat Starch II. Fermentation and Economics", Energy Sources, 23:427-436 (2001).
Lutzen, "Enzyme Technology in the Production of Ethanol—Recent Process Development". Advances in Biotechnology, vol. II: Fuels, Chemicals, Foods and Waste Treatment, 1981 Pergarnon Pres Canada Ltd., pp. 161-167.
Makarov, O. et al. "Quality improvement of table wines following continuous clarification treatments," Kharachova Promislovist (1976)(1 page Abstract).
Matsumoto et al., "Industrialization of a Noncooking System for Alcoholic Fermentation from Grains", Agric. Biol. Chem. 46(6): 1549-1558 (1982).
Matsuoka et al., "Alcoholic Fermentation of Sweet Potato without Cooking", J. Ferment. Technol., vol. 60, No. 6, pp. 599-602 (1982).
Mcaloon et al., "Determining the Cost of Producing Ethanol from Corn Starch and Lignocellulosic Feedstocks", Technical Report NRELTP-580-28893, (Oct. 2000) www.doe.gov/bridge.
Mclean et al. A Novel Method for Quantitation of Active Yeast Cells, Technical Report, 3;5-25 (2002).
Mclean et al., "Fluorometric Method for Measuring Yeast Metabolic Activity", Technical Report, 3:5-25 (2002).
Mikuni et al., "Alcohol Fermentation of Corn Starch Digested by *Chalara paradoxa* Amylase without Cooking", Biotechnology and Bioengineering, vol. XXIX, p. 729-732 1987.
Minnesota Pollution Control Agency (i.e MPCA) (2002). Ethanol Production in Minnesota. Air Quality/General #1.20! Oct. pp. 1-4.
Morris, et al., "AFM Images of Complexes between Amylose and *Aspergillus niger* Glucoamylase Mutants, Native and Mutant Starch Binding Domains: A Model for the Action of glucoamylase", Starch/Starke, 57:1-7 (2005).
Naidu Beesabathuni, "Effect of Corn Flour Particle Size on Ethanol Yield and Soluble Solids in Thin Stillage in a Dry Grind Process." American Society of Agricultural and Biological Engineers, Paper No. 036067, 2003.
Naidu et al., "Effects of Particle Size Reduction on Saccharification in Dry Grind Corn Processing", Department of Agriculture of Biological Engineering, University of Illinois at Urbana Champaign, Poster Presentation 2002 or later.
Narendranath et al., "Acetic Acid Lactic Acid Inhibition of Growth of *Saccharomyces cerevisiac* b Different Mechanisms", American Society of Brewing Chemists, Inc. 59(4): 187-194 (2001).
Narendranath et al., "Effect of yeast inoculation rate on the metabolism of contaminating lactobailli during fermentation of corn mash", J. Ind. Microbiol. Biotechnol. 31:581-584 (2004).
Narendranath et al., "Effects of acetic acid and lactic acid on the growth of *Saccharomyces cerevisiae* in minimal medium", Journal of Industrial Microbiology & Biotechnology, 26: 171-177 (2001).
Narendranath et al., "Effects of Lactobacilli on Yeast-Catalyzed Ethanol Fermentations", Applied and Environmental Microbiology, vol. 60, No. 11, p. 4158-4163 (Nov. 1997).
Narendranath et al., "Relationship between pH and Medium Dissolved Solids in Terms of Growth and Metabolism of *Lactobacilli* and *Saccharomyces cervisiae* during Ethanol Production", Applied and Environmental Microbiology, vol. 71, No. 5, p. 2239-2243 (May 2005).
Narendranath et al., "Urea hydrogen Peroxide Reduces the Number of Laactobacilli Nourishes Yeast, and Leaves No Residues in the Ethanol Fermentation", Applied and Environmental Microbiology, vol. 66, No. 10, p. 4187-4192 (Oct. 2000).

(56) References Cited

OTHER PUBLICATIONS

Narita et al., "Efficient Production of L-(+)-Lactic Acid from Raw Starch by *Streptococcus bovis* 148" Journal of Bioscience and Bioengineering, vol. 97, No. 6, 423-425 (2004).
Patent Title Word Search, Sep. 28, 2005.
PCT Patent Title Word Search, Genencor Assignee, Oct. 4, 2005.
Porter et al., "Variability in Soy Flour Composition", JAOCS, vol. 80, No. 6, pp. 557-562 (2003).
Pourbafrani et al., "Production of biofules, limonene and pectin from citrus wastes." Bioresource Technology, vol. 10, Feb. 9, 2010, pp. 4246-4250.
Rosentrater, "Understanding Distillers Grain Storage, Handling and Flowability Challenges", Distsillers Grain Quarterly, First Quarter 2006, pp. 18-21.
Saha et al., Raw Starch Absorption, Elution and Digestion behavior of Glucoamylase of *Rhizopus niveus*, J. Ferment. Technol., vol. 61, No. 1, p. 67-72, 1983.
Schnier, J. et al., "Translation Initiation Factor 5A and its Hypusine Modification are Essential for Cell Viability in the yeast *Saccharomyces cerevisiae*," Molecular and Cellular Biology, vol. 11, No. 6, pp. 3105-3114 (Jun. 1991).
Shibuya et al., "Molecular Cloning of the Glucoamylase Gene of *Aspergillus shirousami* and its Expression in *Aspergillus oryzae*", Agric. Biol. Chem., 54(8): 1905-1914 (1990).
Shleser, R., "Ethanol Production in Hawaii: Processes, Feedstocks, and Current Economic Feasibility of Fuel Grade Ethanol Produciton in Hawaii" Hawaii State Department of Business, Economic Development & Tourism, Final Report (Jul. 1994).
Shurson, J., "Overview of Swine Nutrition Research on the Value and Application of Distiller's Dried Grains with Solubles Produced by Minnesota and South Dakota Ethanol Plants", pp. 1-40 (Internet Mar. 2003).
Shurson. "The Value of High-Protein Distillers Coproducts in Swine Feeds." Distillers Grains Quarterly, First Quarter, pp. 22-25, 2006.
Sigmund et al., "The Economics of Fair Play", Scientific American, pp. 83-87 (Jan. 2002).
Singleton, P. et al., 1991. Dictionary of Microbiology and Molecular Biology, 1991. John Wiley and Sons. p. 964, col. I, II, 45-48.
Springer Link-Article, Web Page—Article—Natural Resources—"Ethanol Fuels: Energy Balance, Economics, and Environmental Impacts Are Negative", Printed Jul. 5, 2005, pp. 1-2.
Supplementary European Search Report Dated Sep. 21, 2010 in EP application 04719274 (098797-1015).
Suresh, K. et al., "Production of ethanol by raw starch hydrolysis and fermentation of damaged grains of wheat and sorghum," Bioprocess Engineering, vol. 21, pp. 165-168 (1999).
Swanson, Company Spotlight, "Partnering in Progress", Ethanol Producer Magazine, pp. 62-68, Dec. 2004.
Taylor et al., "Dry-Grind Process for Fuel Ethanol by Continuous Fermentation and Stripping", American Chemical Society and American Institute of Chemical Engineers, accepted for publication Mar. 27, 2000, p. A-G.
Taylor et al., "Some Properties of a Glucoamylase produced by the Thermophilic Fungus *Humicola lanuginose*", Carbohydrate Research, 61:301-308 (1978).
Thammarutwasik et al., "Alcoholic Fermentation of Sorghum Without Cooking", Biotechnology and Bioengineering, vol. 28 pp. 1122-1125 (Jul. 1986).
The fuel of the future, Novozymes (May 2002).
Thomas et al., "Fuel Alcohol Production: Effects of Free Amino Nitrogen on Fermentation of Very-High-Gravity Wheat Mashes", Applied and Environmental Microbiology, vol. 56, No. 7, p. 2046-2050 (Jul. 1990).
Tosi et al., "Purification and characterization of an extracellular glucoamylase from the thermophilic fungus *Humicola grisea* var. thermoidea". Can J. Microbiol., vol. 39, pp. 846-852 (1993).
Tritto et al., "2 grants, 6 clients boot yields at ethanol center", St. Louis Business Journal, Nov. 26-Dec. 2, 2004.
Ueda et al., "Alchoholic Fermentation of Raw Starch without Cooking by Using Back-koji Amylase" J Ferment. Technol., vol. 58, No. 3, p. 237-242 (1980).
Ueda et al., "Direct hydrolysis of raw starch", Microbiological Sciences, vol. 1, No. 1, pp. 21-24 (1984).
Ueda, "Ethanol Fermentation of Starch Materials without Cooking", J. Jap. Soc. Starch Sci., 29(2):123-130 (1982), (English Abstract).
Van Maris et al., "Alcoholic fermentation of carbon sources in biomass hydrolysates by *Saccharomyces cerevisiae*: current status," Antionie Van Leeuwenhoek, vol. 90, 2006, pp. 391-418.
Van Uden et al., "Effects of ethanol on yeast performance; targets and underlying mechanisms". European Brewery Convention, Proceeding of the 19.sup.th Congress, London (1983) pp. 137-144.
Vitanen et al., "Production of a xylose utilizing *Zymomonas mobilis* strain for ethanol production from high concentrations of mixed sugars" 31st symposium on biotechnology for fuels and chemicals; San Francisco, CA May 2009, pp. 48-48.
Wang, "Argonne National Laboratory Ethanol Study: Key points." Office of Energy Efficiency and Renewal Energy—U.S. Department of Energy, pp. 1-3, 2005.
Waxy Corn, U.S. Grains Council, pp. 1-8 (Internet Mar. 2003).
Weigel et al., "Feed Co-Products of the Dry Corn Milling Process", Feed Co-Products Handbook, pp. 1-13 (Internet Mar. 2003).
Weiss et al. Updated 2009 Distillers Grains—eXtension, pp. 1-6, Printed May 8, 1010.
Weller et al., "Fuel Ethanol from Raw Corn by *Aspergilli* Hydrolysis with Concurrent Yeast Fermentation", Biotechnology and Bioengineering Symp., No. 13, pp. 437-447 (1983).
www.nrel.gov/docs/fy02osti/31195.pdf. Biofuels News, vol. 4, No. 3. Fall 2001.
Yue et al., Functionality of resistant starch in food applications:, National Starch & Chemical (reprinted from Dec. 1998 issue of Food Australia) (1999).
Zheng et al., "Enzymatic saccharification of dilute acid pretreated saline crops for fermentable sugar production." Applied Energy, vol. 86, Apr. 11, 2009, pp. 2459-2465.
Ziffer et al., 1982. "Temperature Effects in Ethanol Fermentation High Corn Media," Biotechnology Letters, vol. 4, No. 12, pp. 809-814.
Gulati et al. 1996. Assessment of Ethanol Production Options for Corn Products. Bioresource Technology, vol. 58, pp. 253-264.
Nigam et al. 1995. Enzyme and microbial systems involved in starch processing. Enzyme and Microbial Technology, vol. 17, pp. 770-778.
De Mancilha at al., "Evaluation of Ion Exchange Resins for Removal of Inhibitory Compounds from Corn Stover Hydrolyzate for Xylitol Fermentation", Biotechnology Progress, 2003, vol. 19, pp. 1837-1841.
Jeffries et al., "Fermentation of Hemiceilubsic Sugars and Sugar Mixtures by Candida shehatee", Biotechnology and Bioengineering, 1988, vol. 31, pp. 502-506.
Nilvebrandt et al., "Detoxification of Lignocellulose Hydrolysates with Ion-Exchange Resins", Applied Biochemistry and Biotechnology, vols. 91-93, 2001, pp. 35-49.
Extended European Search Report dated Oct. 29, 2012 in related European Application Serial #12184429.4.
Taherzedeh, et al., Pretreatment of Lignocellulosic Wastes to Improve Ethanol and Biogas Production: A Review, Int. J. Mol. Sci., 9:1621-1651 (2008).

* cited by examiner

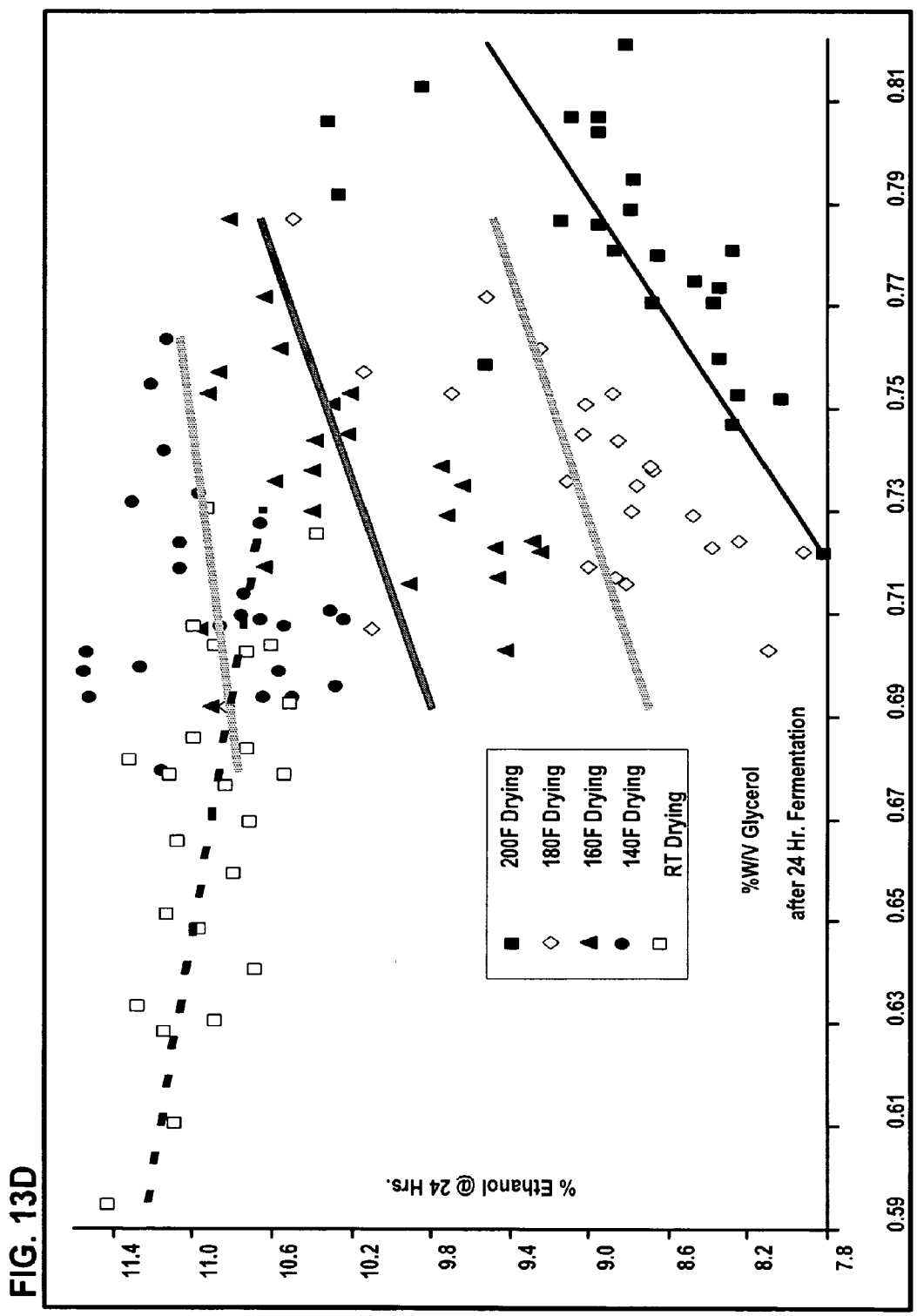

METHODS AND SYSTEMS FOR PRODUCING ETHANOL USING RAW STARCH AND SELECTING PLANT MATERIAL

CROSS REFERENCE TO RELATED APPLICATIONS

The present application claims priority to and is a continuation of U.S. application Ser. No. 11/546,522, filed Oct. 10, 2006, now U.S. Pat. No. 7,919,289, which claims the benefit of Provisional Application No. 60/725,465, filed on Oct. 10, 2005, and incorporates by reference in their entirety that application and U.S. patent application Ser. No. 11/077,969, filed Mar. 10, 2005, and Ser. No. 10/798,226, filed Mar. 10, 2004.

FIELD OF THE INVENTION

The present invention relates to methods for producing high levels of alcohol during fermentation of plant material, and to the high alcohol beer produced. The method can include selecting plant material. Selecting can include excluding plant material that has been exposed to high temperatures or that has had high moisture content.

BACKGROUND OF THE INVENTION

Numerous conventional methods exist for converting plant material to ethanol. However, these methods suffer from numerous inefficiencies. There remains a need for additional more effective methods for converting plant material to ethanol and for producing improved fermentation products.

SUMMARY OF THE INVENTION

The present invention relates to methods for producing high levels of alcohol during fermentation of plant material, and to the high alcohol beer produced. The method can include selecting plant material. Selecting can include excluding plant material that has been exposed to high temperatures or that has had high moisture content.

In an embodiment, the present invention relates to a process for producing ethanol from plant material. The method can include selecting plant material. Selecting plant material can include excluding plant material previously exposed to a temperature in excess of about 200° F. Selecting plant material can include excluding plant material of or that previously had moisture content in excess of 40%. This method includes fractionating the plant material; grinding the plant material (e.g., fractionated plant material) to produce ground plant material (e.g., fractionated plant material) including starch; saccharifying the starch, without cooking; fermenting the incubated starch; and recovering the ethanol from the fermentation. The present method can include varying the temperature during fermentation. The present method can include employing plant material (e.g., fractionated plant material) with a particle size such that more than 50% of the material fits though a sieve with a 0.5 mm mesh. The present method can yield a composition including at least 18 vol-% ethanol.

BRIEF DESCRIPTION OF THE FIGURES

FIGS. 13A, 13B, 13C, 13D, and 13E depict the effects of drying temperature (FIG. 13A and 13B), initial corn moisture content (FIG. 13C), and glycerol concentrations (FIG. 13E) on ethanol yields upon fermentation.

DETAILED DESCRIPTION OF THE INVENTION

Definitions

Figure 1:
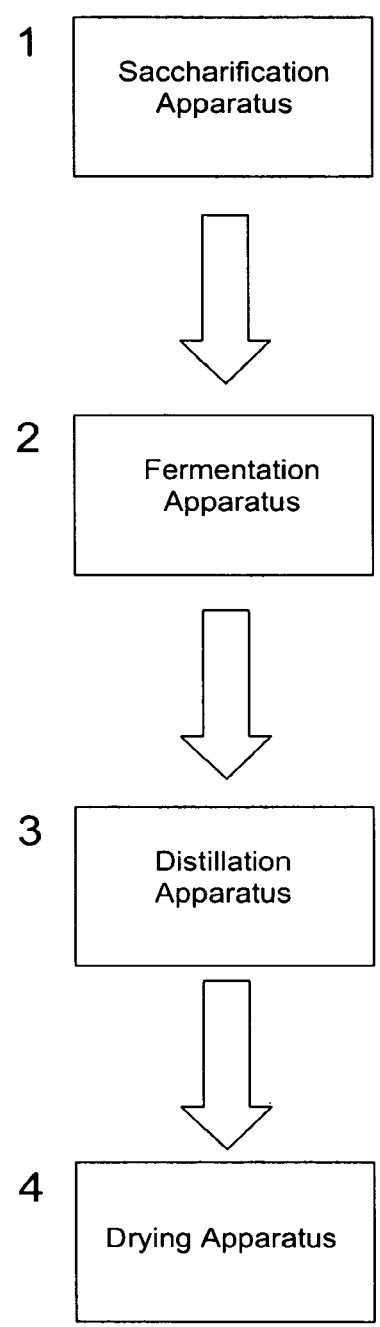
FIG. 1 schematically illustrates a fermentation system according to an embodiment of the present invention.

As used herein, the phrase "without cooking" refers to a process for converting starch to ethanol without heat treatment for gelatinization and dextrinization of starch using alpha-amylase. Generally, for the process of the present invention, "without cooking" refers to maintaining a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polymer type. In the method of the present invention, dextrinization of starch using conventional liquefaction techniques is not necessary for efficient fermentation of the carbohydrate in the grain.

As used herein, the phrase "plant material" refers to all or part of any plant (e.g., cereal grain), typically a material including starch. Suitable plant material includes grains such as maize (corn, e.g., whole ground corn), sorghum (milo), barley, wheat, rye, rice, and millet; and starchy root crops, tubers, or roots such as sweet potato and cassava. The plant material can be a mixture of such materials and byproducts of such materials, e.g., corn fiber, corn cobs, stover, or other cellulose and hemicellulose containing materials such as wood or plant residues. Suitable plant materials include corn, either standard corn or waxy corn.

As used herein, the phrase "fractionated plant material" refers to plant material that includes only a portion or fraction of the total plant material, typically a material including starch. Fractionated plant material can include fractionated grains such as fractionated maize (fractionated corn), fractionated sorghum (fractionated milo), fractionated barley, fractionated wheat, fractionated rye, fractionated rice, and fractionated millet; and fractionated starchy root crops, tubers, or roots such as fractionated sweet potato and fractionated cassava. Suitable fractionated plant materials include fractionated corn, either fractionated standard corn or fractionated waxy corn.

As used herein, the terms "saccharification" and "saccharifying" refer to the process of converting starch to smaller polysaccharides and eventually to monosaccharides, such as glucose. Conventional saccharification uses liquefaction of gelatinized starch to create soluble dextrinized substrate which glucoamylase enzyme hydrolyzes to glucose. In the present method, saccharification refers to converting raw starch to glucose with enzymes, e.g., glucoamylase and acid fungal amylase (AFAU). According to the present method, the raw starch is not subjected to conventional liquefaction and gelatinization to create a conventional dextrinized substrate.

As used herein, a unit of acid fungal amylase activity (AFAU) refers to the standard Novozymes units for measuring acid fungal amylase activity. The Novozymes units are described in a Novozymes technical bulletin SOP No.: EB-SM-0259.02/01. Such units can be measured by detecting products of starch degradation by iodine titration. 1 unit is defined as the amount of enzyme that degrades 5.260 mg starch dry matter per hour under standard conditions.

As used herein, a unit of glucoamylase activity (GAU) refers to the standard Novozymes units for measuring glucoamylase activity. The Novozymes units and assays for determining glucoamylase activity are described in a publicly available Novozymes technical bulletin.

As used herein, a unit of amyloglucosidase activity (AGU) refers to the standard Novozymes units for measuring amyloglucosidase activity. The Novozymes units are described in a Novozymes technical bulletin SOP No.: EB-SM-0131.02/01. Such units can be measured by detecting conversion of maltose to glucose. The glucose can be determined using the glucose dehydrogenase reaction. 1 unit is defined as the amount of enzyme that catalyzes the conversion of 1 mmol maltose per minute under the given conditions.

As used herein, the term "about" modifying any amount refers to the variation in that amount encountered in real world conditions of producing sugars and ethanol, e.g., in the lab, pilot plant, or production facility. For example, an amount of an ingredient employed in a mixture when modified by "about" includes the variation and degree of care typically employed in measuring in an ethanol production plant or lab. For example, the amount of a component of a product when modified by "about" includes the variation between batches in an ethanol production plant or lab and the variation inherent in the analytical method. Whether or not modified by "about," the amounts include equivalents to those amounts. Any quantity stated herein and modified by "about" can also be employed in the present invention as the amount not modified by "about."

Converting Starch to Ethanol

The present invention relates to methods for producing high levels of alcohol during fermentation of plant material (e.g., fractionated plant material), and to the high alcohol beer produced. The present invention also relates to methods for producing high protein distiller's dried grain from fermentation of plant material (e.g., fractionated plant material), to the high protein distiller's dried grain produced, and to the cleaner dryer stack emissions.

The present method converts starch from plant material (e.g., fractionated plant material) to ethanol. In an embodiment, the present method can include preparing the plant material (e.g., fractionated plant material) for saccharification, converting the prepared plant material (e.g., fractionated plant material) to sugars without cooking, and fermenting the sugars.

The plant material (e.g., fractionated plant material) can be prepared for saccharification by any a variety of methods, e.g., by grinding, to make the starch available for saccharification and fermentation. In an embodiment, the vegetable material can be ground so that a substantial portion, e.g., a majority, of the ground material fits through a sieve with a 0.1-0.5 mm screen. For example, in an embodiment, about 70% or more, of the ground vegetable material can fit through a sieve with a 0.1-0.5 mm screen. In an embodiment, the reduced plant material (e.g., fractionated plant material) can be mixed with liquid at about 20 to about 50 wt-% or about 25 to about 45 wt-% dry reduced plant material (e.g., fractionated plant material).

The present process can include converting reduced plant material (e.g., fractionated plant material) to sugars that can be fermented by a microorganism such as yeast. This conversion can be effected by saccharifying the reduced plant material (e.g., fractionated plant material) with an enzyme preparation, such as a saccharifying enzyme composition. A saccharifying enzyme composition can include any of a variety of known enzymes suitable for converting reduced plant material (e.g., fractionated plant material) to fermentable sugars, such as amylases (e.g., α-amylase and/or glucoamylase). In an embodiment, saccharification is conducted at a pH of about 6.0 or less, for example, about 4.5 to about 5.0, for example, about 4.5 to about 4.8.

The present process includes fermenting sugars from reduced plant material (e.g., fractionated plant material) to ethanol. Fermenting can be effected by a microorganism, such as yeast. In an embodiment, fermentation is conducted at a pH of about 6 or less, for example, about 4.5 to about 5, for example, about 4.5 to about 4.8. In an embodiment, the present method can include varying the pH. For example, fermentation can include filling the fermenter at pH of about 3 to about 4.5 during the first half of fill and at a pH of about 4.5 to about 6 (e.g., about 4.5 to about 4.8) during the second half of the fermenter fill cycle. In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, fermentation is conducted for about 25 (e.g., 24) to about to 150 hours, for example, for about 48 (e.g., 47) to about 96 hours.

The present process can include simultaneously converting reduced plant material (e.g., fractionated plant material) to sugars and fermenting those sugars with a microorganism such as yeast.

The product of the fermentation process is referred to herein as "beer". Ethanol can be recovered from the fermentation mixture, from the beer, by any of a variety of known processes, such as by distilling. The remaining stillage includes both liquid and solid material. The liquid and solid can be separated by, for example, centrifugation.

Selecting the Plant Material

The present method converts starch from plant material (e.g., fractionated plant material) to ethanol. The plant material (e.g., fractionated plant material) can be selected for having any of a variety of advantageous properties or for lacking any of a variety of disadvantageous properties. In an embodiment, the method can include selecting plant material with low to moderate water content, selecting plant material that has not been exposed to high temperatures, or both. Although not limiting to the present invention, it is believed that gentle drying of plant material can reduce water content while maintaining activity of advantageous enzymes within the plant material, such as glycosidase and protease.

In an embodiment, the present method includes selecting plant material that has not been exposed to high temperatures. That is, this embodiment excludes plant material that has been exposed to high temperatures, for example, during drying, shipping, other processing, or the like. This embodiment can include selecting plant material, the selected plant material excluding plant material previously exposed to a temperature in excess of about 200° F. For example, the method can include excluding plant material previously exposed to a temperature in excess of about 170° F. or excluding plant material previously exposed to a temperature in excess of about 140° F.

By way of further example, in certain embodiments: The present method can include excluding plant material previously exposed to a temperature in excess of about 200° F. The present method can include excluding plant material previously exposed to a temperature in excess of about 195° F. The present method can include excluding plant material previously exposed to a temperature in excess of about 190° F. The present method can include excluding plant material previously exposed to a temperature in excess of about 185° F. The present method can include excluding plant material previously exposed to a temperature in excess of about 180° F. The present method can include excluding plant material previously exposed to a temperature in excess of about 175° F. The present method can include excluding plant material previously exposed to a temperature in excess of about 170° F. The present method can include excluding plant material previously exposed to a temperature in excess of about 165° F. The present method can include excluding plant material previously exposed to a temperature in excess of about 160° F. The present method can include excluding plant material previously exposed to a temperature in excess of about 155° F. The present method can include excluding plant material previously exposed to a temperature in excess of about 150° F. The present method can include excluding plant material previously exposed to a temperature in excess of about 145° F. The present method can include excluding plant material previously exposed to a temperature in excess of about 140° F. The present method can include excluding plant material previously exposed to a temperature in excess of about 135° F. The present method can include excluding plant material previously exposed to a temperature in excess of about 130° F.

By way of further example, in certain embodiments: The present method can include selecting plant material that had not previously been exposed to a temperature in excess of about 200° F. The present method can include selecting plant material that had not previously been exposed to a temperature in excess of about 195° F. The present method can include selecting plant material that had not previously been exposed to a temperature in excess of about 190° F. The present method can include selecting plant material that had not previously been exposed to a temperature in excess of about 185° F. The present method can include selecting plant material that had not previously been exposed to a temperature in excess of about 180° F. The present method can include selecting plant material that had not previously been exposed to a temperature in excess of about 175° F. The present method can include selecting plant material that had not previously been exposed to a temperature in excess of about 170° F. The present method can include selecting plant material that had not previously been exposed to a temperature in excess of about 165° F. The present method can include selecting plant material that had not previously been exposed to a temperature in excess of about 160° F. The present method can include selecting plant material that had not previously been exposed to a temperature in excess of about 155° F. The present method can include selecting plant material that had not previously been exposed to a temperature in excess of about 150° F. The present method can include selecting plant material that had not previously been exposed to a temperature in excess of about 145° F. The present method can include selecting plant material that had not previously been exposed to a temperature in excess of about 140° F. The present method can include selecting plant material that had not previously been exposed to a temperature in excess of about 135° F. The present method can include selecting plant material that had not previously been exposed to a temperature in excess of about 130° F.

In an embodiment, the present method can include excluding plant material that was subjected to drying at more than a threshold temperature. Drying includes contacting the plant material with heated air. The present method can include excluding plant material contacted with air above a threshold temperature. By way of example, in certain embodiments: The present method can include present method can include excluding plant material dried at a temperature in excess of about 200° F. The present method can include excluding plant material dried at a temperature in excess of about 195° F. The present method can include present method can include excluding plant material dried at a temperature in excess of about 190° F. The present method can include excluding plant material dried at a temperature in excess of about 185° F. The present method can include excluding plant material dried at a temperature in excess of about 180° F. The present method can include excluding plant material dried at a temperature in excess of about 175° F. The present method can include excluding plant material dried at a temperature in excess of about 170° F. The present method can include excluding plant material dried at a temperature in excess of about 165° F. The present method can include excluding plant material dried at a temperature in excess of about 160° F. The present method can include excluding plant material dried at a temperature in excess of about 155° F. The present method can include excluding plant material dried at a temperature in excess of about 150° F. The present method can include excluding plant material dried at a temperature in excess of about 145° F. The present method can include excluding plant material dried at a temperature in excess of about 140° F. The present method can include excluding plant material dried at a temperature in excess of about 135° F. The present method can include excluding plant material dried at a temperature in excess of about 130° F.

By way of example, in certain embodiments: The present method can include present method can include selecting plant material dried at a temperature in below of about 200° F. The present method can include present method can include selecting plant material dried at a temperature in below of about 195° F. The present method can include present method can include selecting plant material dried at a temperature in below of about 190° F. The present method can include present method can include selecting plant material dried at a temperature in below of about 185° F. The present method can include present method can include selecting plant material dried at a temperature in below of about 180° F. The present method can include present method can include selecting plant material dried at a temperature in below of about 175° F. The present method can include present method can include selecting plant material dried at a temperature in below of about 170° F. The present method can include present method can include selecting plant material dried at a temperature in below of about 165° F. The present method can include present method can include selecting plant material dried at a temperature in below of about 160° F. The present method can include present method can include selecting plant material dried at a temperature in below of about 155° F. The present method can include present method can include selecting plant material dried at a temperature in below of about 150° F. The present method can include present method can include selecting plant material dried at a temperature in below of about 145° F. The present method can include present method can include selecting plant material dried at a temperature in below of about 140° F. The present method can include present method can include selecting plant material dried at a temperature in below of about 135° F. The present method can include present method can include selecting plant material dried at a temperature in below of about 130° F.

In an embodiment, the present method includes selecting plant material that has not had high moisture content, for example, as growing plant in the field or as freshly harvested plant material. That is, this embodiment excludes plant material that has had a high moisture content when growing, upon harvesting, upon storage, during other processing, or the like. This embodiment can include selecting plant material, the selected plant material excluding plant material of or that previously had moisture content in excess of 40 wt-%. For example, the method can include excluding plant material of or that previously had moisture content in excess of about 35 wt-% or excluding plant material of or that previously had moisture content in excess of about 30 wt-%.

By way of further example, in certain embodiments: The present method can include excluding plant material of or that previously had moisture content in excess of about 40 wt-%. The present method can include excluding plant material of or that previously had moisture content in excess of 39 wt-%. The present method can include excluding plant material of or that previously had moisture content in excess of 38 wt-%. The present method can include excluding plant material of or that previously had moisture content in excess of 37 wt-%. The present method can include excluding plant material of or that previously had moisture content in excess of 36 wt-%. The present method can include excluding plant material of or that previously had moisture content in excess of about 35 wt-%. The present method can include excluding plant material of or that previously had moisture content in excess of 34 wt-%. The present method can include excluding plant material of or that previously had moisture content in excess of 33 wt-%. The present method can include excluding plant material of or that previously had moisture content in excess of 32 wt-%. The present method can include excluding plant material of or that previously had moisture content in excess of 31 wt-%. The present method can include excluding plant material of or that previously had moisture content in excess of about 30 wt-%. The present method can include excluding plant material of or that previously had moisture content in excess of 29 wt-%. The present method can include excluding plant material of or that previously had moisture content in excess of 28 wt-%. The present method can include excluding plant material of or that previously had moisture content in excess of about 25 wt-%.

By way of further example, in certain embodiments: The present method can include selecting plant material of or that had not previously had moisture content in excess of about 40 wt-%. The present method can include selecting plant material of or that had not previously had moisture content in excess of 39 wt-%. The present method can include selecting plant material of or that had not previously had moisture content in excess of 38 wt-%. The present method can include selecting plant material of or that had not previously had moisture content in excess of 37 wt-%. The present method can include selecting plant material of or that had not previously had moisture content in excess of 36 wt-%. The present method can include selecting plant material of or that had not previously had moisture content in excess of about 35 wt-%. The present method can include selecting plant material of or that had not previously had moisture content in excess of 34 wt-%. The present method can include selecting plant material of or that had not previously had moisture content in excess of 33 wt-%. The present method can include selecting plant material of or that had not previously had moisture content in excess of 32 wt-%. The present method can include selecting plant material of or that had not previously had moisture content in excess of 31 wt-%. The present method can include selecting plant material of or that had not previously had moisture content in excess of about 30 wt-%. The present method can include selecting plant material of or that had not previously had moisture content in excess of 29 wt-%. The present method can include selecting plant material of or that had not previously had moisture content in excess of 28 wt-%. The present method can include selecting plant material of or that had not previously had moisture content in excess of 25 wt-%.

Although not limiting to the present invention, it is believed that plant material of lower moisture content can be advantageous because it requires less heat for drying. Plant material, such as corn or soybeans, can be dried by the grower to a moisture content of about 13 wt-%. This moisture content retards spoilage but retains weight in the plant material. Plant material that is grown or harvested at a moisture content above, but close to, 13 wt-% (e.g., 28 wt-%) can be dried gently, at with lower temperature air or with shorter exposure to higher temperature air. Thus, the lower moisture content can correlate with exposure to lower temperature or less heat. In contrast, plant material grown or harvested with a higher moisture content (e.g., 37 wt-%) requires more heat and/or higher temperatures for drying to about 13 wt-% moisture.

Preparing the Plant Material

The present method converts starch from plant material (e.g., fractionated plant material) to ethanol. The plant material (e.g., fractionated plant material) can be reduced by a variety of methods, e.g., by grinding, to make the starch available for saccharification and fermentation. Other methods of plant material reduction are available. For example, vegetable material, such as kernels of corn, can be ground with a ball mill, a roller mill, a hammer mill, or another mill known for grinding vegetable material, and/or other materials for the purposes of particle size reduction. The use of emulsion technology, rotary pulsation, and other means of particle size reduction can be employed to increase surface area of plant material (e.g., fractionated plant material) while raising the effectiveness of flowing the liquefied media. The prepared plant material (e.g., fractionated plant material) can be referred to as being or including "raw starch".

A fine grind exposes more surface area of the plant material (e.g., fractionated plant material), or vegetable material, and can facilitate saccharification and fermentation. In an embodiment, the vegetable material is ground so that a substantial portion, e.g., a majority, of the ground material fits through a sieve with a 0.1-0.5 mm screen. In an embodiment, about 35% or more of the ground vegetable material can fit through a sieve with a 0.1-0.5 mm screen. In an embodiment, about 35 to about 70% of the ground vegetable material can fit through a sieve with a 0.1-0.5 mm screen. In an embodiment, about 50% or more of the ground vegetable material can fit through a sieve with a 0.1-0.5 mm screen. In an embodiment, about 90% of the ground vegetable material can fit through a sieve with a 0.1-0.5 mm screen. In an embodiment, all of the ground vegetable material can fit through a sieve with a 0.1-0.5 mm screen. In an embodiment, the ground vegetable material has an average particle size of about 0.25 mm.

Plant Material Reduction

Preparing the plant material (e.g., fractionated plant material) can employ any of a variety of techniques for plant material (e.g., fractionated plant material) reduction. For example, the present method of preparing plant material (e.g., fractionated plant material) can employ emulsion technology, rotary pulsation, sonication, magnetostriction, ferromagnetic materials, or the like. These methods of plant material reduction can be employed for substrate pretreatment. Although not limiting to the present invention, it is believed that these methods can increase surface area of plant material (e.g., fractionated plant material) while raising the effectiveness of flowing of liquefied media (i.e. decreased viscosity). These methods can include electrical to mechanical, mechanical to electrical, pulse, and sound based vibrations at varying speeds. This can provide varying frequencies over a wide range of frequencies, which can be effective for pretreating the plant material (e.g., fractionated plant material) and/or reducing particle size.

Although not limiting to the present invention, it is believed that certain of these sonic methods create low pressure around a particle of plant material (e.g., fractionated plant material) and induce cavitation of the particle or disruption of the particle structure. The cavitated or disrupted particle can increase availability of plant material (e.g., starch) to an enzyme, for example, by increasing surface area. It is believed that such pretreatment can decrease quantity of enzyme rates in the present method for ethanol production.

In an embodiment, the present method includes vibrating plant material (e.g., fractionated plant material) and cavitating the fluid containing the plant material. This can result in disrupting the plant material and/or decreasing the size of the plant material (e.g., fractionated plant material). In certain embodiments, the present method includes treating plant material (e.g., fractionated plant material) with emulsion technology, with rotary pulsation, with magnetostriction, or with ferromagnetic materials. This can result in disrupting the plant material and/or decreasing the size of the plant material (e.g., fractionated plant material). In an embodiment, the present method includes sonicating the plant material (e.g., fractionated plant material). This can result in disrupting the plant material and/or decreasing the size of the plant material (e.g., fractionated plant material).

In an embodiment, the present method can include employing sound waves for reducing plant material (e.g., fractionated plant material). The sound waves can be ultrasound. The present method can include sonicating the plant material (e.g., fractionated plant material). The method can include sonicating the plant material at a frequency (e.g., measured in kHz), power (e.g., measured in watts), and for a time effective to reduce (or to assist in reducing) the particle size to sizes described hereinabove. For example, the method can include sonicating the plant material (e.g., fractionated plant material) at 20,000 Hz and up to about 3000 W for a sufficient time and at a suitable temperature. Such sonicating can be carried out with commercially available apparatus, such as high powered ultrasonics available from ETREMA (Ames, Iowa).

In an embodiment, the present method can include employing rotary pulsation for reducing plant material (e.g., fractionated plant material). The method can include rotary pulsating the plant material (e.g., fractionated plant material) at a frequency (e.g., measured in Hz), power (e.g., measured in watts), and for a time effective to reduce (or to assist in reducing) the particle size to sizes described hereinabove. Such rotary pulsating can be carried out with known apparatus, such as apparatus described in U.S. Pat. No. 6,648,500, the disclosure of which is incorporated herein by reference.

In an embodiment, the present method can include employing pulse wave technology for reducing plant material (e.g., fractionated plant material). The method can include rotary pulsing the plant material at a frequency (e.g., measured in Hz), power (e.g., measured in watts), and for a time effective to reduce (or to assist in reducing) the particle size to sizes described hereinabove. Such pulsing can be carried out with known apparatus, such as apparatus described in U.S. Pat. No. 6,726,133, the disclosure of which is incorporated herein by reference.

Fractionation

In an embodiment, the vegetable material can be fractionated into one or more components. For example, a vegetable material such as a cereal grain or corn can be fractionated into components such as fiber (e.g., corn fiber), germ (e.g., corn germ), and a mixture of starch and protein (e.g., a mixture of corn starch and corn protein). One or a mixture of these components can be fermented in a process according to the present invention. Fractionation of corn or another plant material can be accomplished by any of a variety of methods or apparatus. For example, a system manufactured by Satake can be used to fractionate plant material such as corn.

In an embodiment, the germ and fiber components of the vegetable material can be fractionated and separated from the remaining portion of the vegetable material. In an embodiment, the remaining portion of the vegetable material (e.g., corn endosperm) can be further milled and reduced in particle size and then combined with the larger pieces of the fractioned germ and fiber components for fermenting.

In an embodiment, the vegetable material can be milled to access value added products (such as neutraceuticals, leutein, carotenoids, xanthrophils, pectin, cellulose, lignin, mannose, xylose, arabinose, galactose, galacturonic acid, GABA, corn oil, albumins, globulins, prolamins, gluetelins, zein and the like).

Fractionation can be accomplished by any of a variety of methods and apparatus, such as those disclosed in U.S. Patent Application Publication No. 2004/0043117, the disclosure of which is incorporated herein by reference. Suitable methods and apparatus for fractionation include a sieve, sieving, and elutriation. Suitable apparatus include a frictional mill such as a rice or grain polishing mill (e.g., those manufactured by Satake, Kett, or Rapsco)

Saccharification and Fermentation

Saccharification

The present process can include converting reduced plant material (e.g., fractionated plant material) to sugars that can be fermented by a microorganism such as yeast. This conversion can be effected by saccharifying the reduced plant material (e.g., fractionated plant material) with any of a variety of known saccharifying enzyme compositions. In an embodiment, the saccharifying enzyme composition includes an amylase, such as an alpha amylase (e.g., an acid fungal amylase). The enzyme preparation can also include glucoamylase. The enzyme preparation need not, and, in an embodiment, does not include protease. However, ethanol production methods according to the present invention can conserve water by reusing process waters (backset) which may contain protease. In an embodiment, the present method employs acid fungal amylase for hydrolyzing raw starch.

Saccharifying can be conducted without cooking. For example, saccharifying can be conducted by mixing source of saccharifying enzyme composition (e.g., commercial enzyme), yeast, and fermentation ingredients with ground grain and process waters without cooking.

In an embodiment, saccharifying can include mixing the reduced plant material (e.g., fractionated plant material) with a liquid, which can form a slurry or suspension and adding saccharifying enzyme composition to the liquid. In an embodiment, the method includes mixing the reduced plant material (e.g., fractionated plant material) and liquid and then adding the saccharifying enzyme composition. Alternatively, adding enzyme composition can precede or occur simultaneously with mixing.

In an embodiment, the reduced plant material (e.g., fractionated plant material) can be mixed with liquid at about 20 to about 50 wt-%, about 25 to about 45 (e.g., 44) wt-%, about 30 to about 40 (e.g., 39) wt-%, or about 35 wt-% dry reduced plant material (e.g., fractionated plant material). As used herein, wt-% of reduced plant material in a liquid refers to the percentage of dry substance reduced plant material or dry solids. In an embodiment, the method of the present invention can convert raw or native starch (e.g., in dry reduced plant material) to ethanol at a faster rate at higher dry solids levels compared to conventional saccharification with cooking. Although not limiting to the present invention, it is believed that the present method can be practiced at higher dry solids levels because, unlike the conventional process, it does not include gelatinization, which increases viscosity.

Suitable liquids include water and a mixture of water and process waters, such as stillage (backset), scrubber water, evaporator condensate or distillate, side stripper water from distillation, or other ethanol plant process waters. In an embodiment, the liquid includes water. In an embodiment, the liquid includes water in a mixture with about 1 to about 70 vol-% stillage, about 15 to about 60 vol-% stillage, about 30 to about 50 vol-% stillage, or about 40 vol-% stillage.

In the conventional process employing gelatinization and liquefaction, stillage provides nutrients for efficient yeast fermentation, especially free amino nitrogen (FAN) required by yeast. The present invention can provide effective fermentation with reduced levels of stillage and even without added stillage. In an embodiment, the present method employs a preparation of plant material (e.g., fractionated plant material) that supplies sufficient quantity and quality of nitrogen for efficient fermentation under high gravity conditions (e.g., in the presence of high levels of reduced plant material). Thus, in an embodiment, no or only low levels of stillage can suffice.

However, the present method provides the flexibility to employ high levels of stillage if desired. The present method does not employ conventional liquefaction. Conventional liquefaction increases viscosity of the fermentation mixture and the resulting stillage. The present method produces lower viscosity stillage. Therefore, in an embodiment, increased levels of stillage can be employed in the present method without detrimental increases in viscosity of the fermentation mixture or resulting stillage.

Further, although not limiting to the present invention, it is believed that conventional saccharification and fermentation processes require added FAN due to undesirable "Maillard Reactions" which occur during high temperature gelatinization and liquefaction. The Maillard Reactions consume FAN during cooking. As a result, the conventional process requires adding stillage (or another source of FAN) to increase levels of FAN in fermentation. It is believed that the present process avoids temperature induced Maillard Reactions and provides increased levels of FAN in the reduced plant material, which are effectively utilized by the yeast in fermentation.

Saccharification can employ any of a variety of known enzyme sources (e.g., a microorganism) or compositions to produce fermentable sugars from the reduced plant material (e.g., fractionated plant material). In an embodiment, the saccharifying enzyme composition includes an amylase, such as an alpha amylase (e.g., an acid fungal amylase) or a glucoamylase.

In an embodiment, saccharification is conducted at a pH of about 6.0 or less, pH of about 3.0 to about 6.0, about 3.5 to about 6.0, about 4.0 to about 5.0, about 4.0 to about 4.5, about 4.5 to about 5.0, or about 4.5 to about 4.8. In an embodiment, saccharification is conducted at a pH of about 4.1 to about 4.6 or about 4.9 to about 5.3. The initial pH of the saccharification mixture can be adjusted by addition of, for example, ammonia, sulfuric acid, phosphoric acid, process waters (e.g., stillage (backset), evaporator condensate (distillate), side stripper bottoms, and the like), and the like. Activity of certain saccharifying enzyme compositions (e.g., one including acid fungal amylase) can be enhanced at pH lower than the above ranges.

In an embodiment, saccharification is conducted at a temperature of about 25 to about 40° C. or about 30 to about 35° C.

In an embodiment, saccharifying can be carried out employing quantities of saccharifying enzyme composition selected to maintain low concentrations of dextrin in the fermentation broth. For example, the present process can employ quantities of saccharifying enzyme composition selected to maintain maltotriose (DP3) at levels at or below about 0.2 wt-% or at or below about 0.1 wt-%. For example, the present process can employ quantities of saccharifying enzyme composition selected to maintain dextrin with a degree of polymerization of 4 or more (DP4+) at levels at or below about 1 wt-% or at or below about 0.5 wt-%.

In an embodiment, saccharifying can be carried out employing quantities of saccharifying enzyme composition selected to maintain low concentrations of maltose in the fermentation broth. For example, the present process can employ quantities of saccharifying enzyme composition selected to maintain maltose at levels at or below about 0.3 wt-%. For maintaining low levels of maltose, suitable levels of acid fungal amylase and glucoamylase include about 0.05 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 0.1 to about 2 AFAU/gram dry solids reduced plant material (e.g., DSC) of acid fungal amylase and about 1 to about 2.5 AGU per gram dry solids reduced plant material (e.g., DSC) of glucoamylase. In an embodiment, the reaction mixture includes about 0.3 to about 2 AFAU/gram dry solids reduced plant material (e.g., DSC) of acid fungal amylase and about 1 to about 2.5 AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

Glucoamylase

In certain embodiments, the present method can employ a glucoamylase. Glucoamylase is also known as amyloglucosidase and has the systematic name 1,4-alpha-D-glucan glucohydrolase (E.C. 3.2.1.3). Glucoamylase refers to an enzyme that removes successive glucose units from the non-reducing ends of starch. For example, certain glucoamylases can hydrolyze both the linear and branched glucosidic linkages of starch, amylose, and amylopectin. A variety of suitable glucoamylases are known and commercially available. For example, suppliers such as Novozymes and Genencor provide glucoamylases. The glucoamylase can be of fungal origin.

The amount of glucoamylase employed in the present process can vary according to the enzymatic activity of the amylase preparation. Suitable amounts include about 0.05 to about 6.0 glucoamylase units (AGU) per gram dry solids reduced plant material (e.g., DSC). In an embodiment, the reaction mixture can include about 1 to about 6 AGU per gram dry solids reduced plant material (e.g., DSC). In an embodiment, the reaction mixture can include about 1 to about 3 AGU per gram dry solids reduced plant material (e.g., DSC). In an embodiment, the reaction mixture can include about 1 to about 2.5 (e.g., 2.4) AGU per gram dry solids reduced plant material (e.g., DSC). In an embodiment, the reaction mixture can include about 1 to about 2 AGU per gram dry solids reduced plant material (e.g., DSC). In an embodiment, the reaction mixture can include about 1 to about 1.5 AGU per gram dry solids reduced plant material (e.g., DSC). In an embodiment, the reaction mixture can include about 1.2 to about 1.5 AGU per gram dry solids reduced plant material (e.g., DSC).

Acid Fungal Amylase

In certain embodiments, the present method employs an α-amylase. The α-amylase can be one produced by fungi. The α-amylase can be one characterized by its ability to hydrolyze carbohydrates under acidic conditions. An amylase produced by fungi and able to hydrolyze carbohydrates under acidic conditions is referred to herein as acid fungal amylase, and is also known as an acid stable fungal α-amylase. Acid fungal amylase can catalyze the hydrolysis of partially hydrolyzed starch and large oligosaccharides to sugars such as glucose. The acid fungal amylase that can be employed in the present process can be characterized by its ability to aid the hydrolysis of raw or native starch, enhancing the saccharification provided by glucoamylase. In an embodiment, the acid fungal amylase produces more maltose than conventional (e.g., bacterial) α-amylases.

Suitable acid fungal amylase can be isolated from any of a variety of fungal species, including *Aspergillus, Rhizopus, Mucor, Candida, Coriolus, Endothia, Enthomophtora, Irpex, Penicillium, Sclerotium* and *Torulopsis* species. In an embodiment, the acid fungal amylase is thermally stable and is isolated from *Aspergillus* species, such as *A. niger, A. saitoi* or *A. oryzae*, from *Mucor* species such as *M. pusillus* or *M. miehei*, or from *Endothia* species such as *E. parasitica*. In an embodiment, the acid fungal amylase is isolated from *Aspergillus niger*. The acid fungal amylase activity can be supplied as an activity in a glucoamylase preparation, or it can be added as a separate enzyme. A suitable acid fungal amylase can be obtained from Novozymes, for example in combination with glucoamylase.

The amount of acid fungal amylase employed in the present process can vary according to the enzymatic activity of the amylase preparation. Suitable amounts include about 0.1 to about 10 acid fungal amylase units (AFAU) per gram of dry solids reduced plant material (e.g., dry solids corn (DSC)). In an embodiment, the reaction mixture can include about 0.05 to about 3 AFAU/gram dry solids reduced plant material (e.g., DSC). In an embodiment, the reaction mixture can include about 0.1 to about 3 AFAU/gram dry solids reduced plant material (e.g., DSC). In an embodiment, the reaction mixture can include about 0.3 to about 3 AFAU/gram dry solids reduced plant material (e.g., DSC). In an embodiment, the reaction mixture can include about 1 to about 2 AFAU/gram dry solids reduced plant material (e.g., DSC).

Fermenting

The present process includes fermenting sugars from reduced plant material (e.g., fractionated plant material) to ethanol. Fermenting can be effected by a microorganism, such as yeast. The fermentation mixture need not, and in an embodiment does not, include protease. However, the process waters may contain protease. The amount of protease can be less than that used in the conventional process. According to the present invention, fermenting is conducted on a starch composition that has not been cooked. In an embodiment, the present fermentation process produces potable alcohol. Potable alcohol has only acceptable, nontoxic levels of other alcohols, such as fusel oils. Fermenting can include contacting a mixture including sugars from the reduced plant material (e.g., fractionated plant material) with yeast under conditions suitable for growth of the yeast and production of ethanol. In an embodiment, fermenting employs the saccharification mixture.

Any of a variety of yeasts can be employed as the yeast starter in the present process. Suitable yeasts include any of a variety of commercially available yeasts, such as commercial strains of *Saccharomyces cerevisiae*. Suitable strains include "Fali" (Fleischmann's), Thermosac (Alltech), Ethanol Red (LeSafre), BioFerm AFT (North American Bioproducts), and the like. In an embodiment, the yeast is selected to provide rapid growth and fermentation rates in the presence of high temperature and high ethanol levels. In an embodiment, Fali yeast has been found to provide good performance as measured by final alcohol content of greater than 17% by volume.

The amount of yeast starter employed is selected to effectively produce a commercially significant quantity of ethanol in a suitable time, e.g., less than 75 hours.

Yeast can be added to the fermentation by any of a variety of methods known for adding yeast to fermentation processes. For example, yeast starter can be added as a dry batch, or by conditioning/propagating. In an embodiment, yeast starter is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage, which is also aerated to encourage yeast growth. The prefermenter used to inoculate the main fermenter can be from 1 to 10% by volume capacity of the main fermenter, for example, from 2.5 to 5% by volume capacity relative to the main fermenter.

In an embodiment, the fermentation is conducted at a pH of about 6 or less, pH of about 3 to about 6, about 3 to about 4.5, about 3.5 to about 6, about 4 to about 5, about 4 to about 4.5, about 4.5 to about 5, or about 4.5 to about 4.8. The initial pH of the fermentation mixture can be adjusted by addition of, for example, ammonia, sulfuric acid, phosphoric acid, process waters (e.g., stillage (backset), evaporator condensate (distillate), side stripper bottoms, and the like), and the like.

Although not limiting to the present invention, it is believed that known distillery yeast grow well over the pH range of 3 to 6, but are more tolerant of lower pH's down to 3.0 than most contaminant bacterial strains. Contaminating lactic and acetic acid bacteria grow best at pH of 5.0 and above. Thus, in the pH range of 3.0 to 4.5, it is believed that ethanol fermentation will predominate because yeast will grow better than contaminating bacteria.

In an embodiment, the present method can include varying the pH. It is believed that varying the pH can be conducted to reduce the likelihood of contamination early in fermentation and/or to increase yeast growth and fermentation during the latter stages of fermentation. For example, fermentation can include filling the fermenter at pH of about 3 to about 4.5 during the first half of fill. Fermentation can include increasing the slurry pH to pH of about 4.5 to about 6 during the second half of the fermenter fill cycle. Fermentation can include maintaining pH by adding fresh substrate slurry at the desired pH as described above. In an embodiment, during fermentation (after filling), pH is not adjusted. Rather, in this embodiment, the pH is determined by the pH of the components during filling.

In an embodiment, the pH is decreased to about five (5) or below in the corn process waters. In an embodiment, the pH is about pH 4 (e.g. 4.1) at the start of fermentation fill and is increased to about pH 5 (e.g. 5.2) toward the end of fermentation fill. In an embodiment, the method includes stopping pH control of the mash slurry after the yeast culture becomes established during the initial process of filling the fermenter, and then allowing the pH to drift up in the corn process waters during the end stages of filling the fermenter.

In an embodiment, fermentation is conducted for about to 25 (e.g., 24) to about to 150 hours, about 25 (e.g., 24) to about 96 hours, about 40 to about 96 hours, about 45 (e.g., 44) to about 96 hours, about 48 (e.g., 47) to about 96 hours. For example, fermentation can be conducted for about 30, about 40, about 50, about 60, or about 70 hours. For example, fermentation can be conducted for about 35, about 45, about 55, about 65, or about 75 hours.

In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, the temperature can be decreased as ethanol is produced. For example, in an embodiment, during fermentation the temperature can be as high as about 99° F. and then reduced to about 79° F. This temperature reduction can be coordinated with increased ethanol titers (%) in the fermenter.

In an embodiment, the present method includes solids staging. Solids staging includes filling at a disproportionately higher level of solids during the initial phase of the fermenter fill cycle to increase initial fermentation rates. The solids concentration of the mash entering the fermenter can then be decreased as ethanol titers increase and/or as the fermenter fill cycle nears completion. In an embodiment, the solids concentration can be about 40% (e.g. 41%) during the first half of the fermentation fill. This can be decreased to about 25% after the fermenter is 50% full and continuing until the fermenter fill cycle is concluded. In the above example, such a strategy results in a full fermenter with solids at 33%.

It is believed that solids staging can accelerate enzyme hydrolysis rates and encourage a rapid onset to fermentation by using higher initial fill solids. It is believed that lowering solids in the last half of fill can reduce osmotic pressure related stress effects on the yeast. By maintaining overall fermenter fill solids within a specified range of fermentability, solids staging improves the capacity of the yeast to ferment high gravity mashes toward the end of fermentation.

Simultaneous Saccharification and Fermentation

The present process can include simultaneously converting reduced plant material (e.g., fractionated plant material) to sugars and fermenting those sugars with a microorganism such as yeast. Simultaneous saccharifying and fermenting can be conducted using the reagents and conditions described above for saccharifying and fermenting.

In an embodiment, saccharification and fermentation is conducted at a temperature of about 25 to about 40° C. or about 30 to about 35° C. In an embodiment, during saccharification and fermentation the temperature is decreased from about 40 to about 25° C. or from about 35 to about 30° C. during the first half of the saccharification, and the temperature is held at the lower temperature for the second half of the saccharification.

Although not limiting to the present invention, it is believed that higher temperatures early during saccharification and fermentation can increase conversion of starch to fermentable sugar when ethanol concentrations are low. This can aid in increasing ethanol yield. At higher ethanol concentrations, this alcohol can adversely affect the yeast. Thus, it is believed that lower temperatures later during saccharification and fermentation are beneficial to decrease stress on the yeast. This can aid in increasing ethanol yield.

Also not limiting to the present invention, it is believed that higher temperatures early during saccharification and fermentation can reduce viscosity during at least a portion of the fermentation. This can aid in temperature control. It is also believed that lower temperatures later during saccharification and fermentation are beneficial to reduce the formation of glucose after the yeast has stopped fermenting. Glucose formation late in fermentation can be detrimental to the color of the distillers dried grain co-product.

In an embodiment, saccharification and fermentation is conducted at a pH of about 6 or less, pH of about 3 to about 6, about 3.5 to about 6, about 4 to about 5, about 4 to about 4.5, about 4.5 to about 5, or about 4.5 to about 4.8. The initial pH of the saccharification and fermentation mixture can be adjusted by addition of, for example, ammonia, sulfuric acid, phosphoric acid, process waters (e.g., stillage (backset), evaporator condensate (distillate), side stripper bottoms, and the like), and the like.

In an embodiment, saccharification and fermentation is conducted for about to 25 (e.g., 24) to about to 150 hours, about 25 (e.g., 24) to about 72 hours, about 45 to about 55 hours, about 50 (e.g., 48) to about 96 hours, about 50 to about 75 hours, or about 60 to about 70 hours. For example, saccharification and fermentation can be conducted for about 30, about 40, about 50, about 60, or about 70 hours. For example, saccharification and fermentation can be conducted for about 35, about 45, about 55, about 65, or about 75 hours.

In an embodiment, simultaneous saccharifying and fermenting can be carried out employing quantities of enzyme and yeast selected to maintain high concentrations of yeast and high levels of budding of the yeast in the fermentation broth. For example, the present process can employ quantities of enzyme and yeast selected to maintain yeast at or above about 200 cells/mL, at or above about 300 cells/mL, or at about 300 to about 600 cells/mL.

In an embodiment, simultaneous saccharifying and fermenting can be carried out employing quantities of enzyme and yeast selected for effective fermentation without added exogenous nitrogen; without added protease; and/or without added backset. Backset can be added, if desired, to consume process water and reduce the amount of wastewater produced by the process. In addition, the present process maintains low viscosity during saccharifying and fermenting.

In an embodiment, simultaneous saccharifying and fermenting can be carried out employing quantities of enzyme and yeast selected to maintain low concentrations of soluble sugar in the fermentation broth. In an embodiment, simultaneous saccharifying and fermenting can be carried out employing quantities of enzyme and yeast selected to maintain low concentrations of glucose in the fermentation broth. For example, the present process can employ quantities of enzyme and yeast selected to maintain glucose at levels at or below about 2 wt-%, at or below about 1 wt-%, at or below about 0.5 wt-%, or at or below about 0.1 wt-%. For example, the present process can employ quantities of enzyme and yeast selected to maintain glucose at levels at or below about 2 wt-% during saccharifying and fermenting. For example, the present process can employ quantities of enzyme and yeast selected to maintain glucose at levels at or below about 2 wt-% from hours 0-10 (or from 0 to about 15% of the time) of saccharifying and fermenting. For example, the present process can employ quantities of enzyme and yeast selected to maintain glucose at levels at or below about 1 wt-%, at or below about 0.5 wt-%, or at or below about 0.1 wt-% from hours 12-54 (or from about 15% to about 80% of the time) of saccharifying and fermenting. For example, the present process can employ quantities of enzyme and yeast selected to maintain glucose at levels at or below about 1 wt-% from hours 54-66 (or about from 80% to about 100% of the time) of saccharifying and fermenting.

In an embodiment, simultaneous saccharifying and fermenting can be carried out employing quantities of enzyme and yeast selected to maintain low concentrations of maltose (DP2) in the fermentation broth. For example, the present process can employ quantities of enzyme and yeast selected to maintain maltose at levels at or below about 0.5 wt-% or at or below about 0.2 wt-%.

In an embodiment, simultaneous saccharifying and fermenting can be carried out employing quantities of enzyme and yeast selected to maintain low concentrations of dextrin in the fermentation broth. For example, the present process can employ quantities of enzyme and yeast selected to maintain maltotriose (DP3) at levels at or below about 0.5 wt-%, at or below about 0.2 wt-%, or at or below about 0.1 wt-%. For example, the present process can employ quantities of enzyme and yeast selected to maintain dextrin with a degree of polymerization of 4 or more (DP4+) at levels at or below about 1 wt-% or at or below about 0.5 wt-%.

In an embodiment, simultaneous saccharifying and fermenting can be carried out employing quantities of enzyme and yeast selected to maintain low concentrations of fusel oils in the fermentation broth. For example, the present process can employ quantities of enzyme and yeast selected to maintain fusel oils at levels at or below about 0.4 to about 0.5 wt-%.

For example, simultaneous saccharifying and fermenting can employ acid fungal amylase at about 0.05 to about 10 AFAU per gram of dry solids reduced plant material (e.g., DSC) and glucoamylase at about 0.5 to about 6 AGU per gram dry solids reduced plant material (e.g., DSC). For example, simultaneous saccharifying and fermenting can employ acid fungal amylase at about 0.1 to about 10 AFAU per gram of dry solids reduced plant material (e.g., DSC) and glucoamylase at about 0.5 to about 6 AGU per gram dry solids reduced plant material (e.g., DSC). For example, simultaneous saccharifying and fermenting can employ acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

Additional Ingredients for Saccharification and/or Fermentation

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like.

Recovering Ethanol from the Beer

The product of the fermentation process is referred to herein as "beer". For example, fermenting corn produces "corn beer". Ethanol can be recovered from the fermentation mixture, from the beer, by any of a variety of known processes. For example, ethanol can be recovered by distillation.

The remaining stillage includes both liquid and solid material. The liquid and solid can be separated by, for example, centrifugation. The recovered liquid, thin stillage, can be employed as at least part of the liquid for forming the saccharification and fermentation mixture for subsequent batches or runs.

The recovered solids, distiller's dried grain, include unfermented grain solids and spent yeast solids. Thin stillage can be concentrated to a syrup, which can be added to the distiller's dried grain and the mixture then dried to form distiller's dried grain plus solubles. Distiller's dried grain and/or distiller's dried grain plus solubles can be sold as animal feed.

Burn-out of Residual Starches for Subsequent Secondary Fermentation

In an embodiment, the present method can include heat treatment of the beer or stillage, e.g., between the beer well and distillation. In an embodiment, the present method can include heat treatment of the beer or stillage and enzyme addition, e.g., between the beer well and distillation. This heat treatment can convert starches to dextrins and sugars for subsequent fermentation in a process known as burn-out. Such a treatment step can also reduce fouling of distillation trays and evaporator heat exchange surfaces. In an embodiment, heat treatment staging can be performed on whole stillage or thin stillage. Following enzymatic treatment of the residual starches, in an embodiment, the resulting dextrins and sugars can be fermented within the main fermentation process as recycled backset or processed in a separate fermentation train to produce ethanol. In an embodiment, the liquefaction and saccharification on whole stillage or thin stillage produced by centrifugation can be accelerated after distillation.

Fractionation of Solids from Fermentation

Large pieces of germ and fiber can ferment the residual starch in the fermenter. After fermentation, the fractions could be removed prior to or after distillation. Removal can be effected with a surface skimmer before to distillation. In an embodiment, screening can be performed on the beer. The screened material can then be separated from the ethanol/ water mix by, for example, centrifugation and rotary steam drum drying, which can remove the residual ethanol from the cake. In embodiments in which the larger fiber and germ pieces are removed prior to bulk beer distillation, a separate stripper column for the fiber/germ stream can be utilized. Alternatively, fiber and germ could be removed by screening the whole stillage after distillation.

In an embodiment, all the components are blended and dried together. The fiber and germ can be removed from the finished product by aspiration and/or size classification. The fiber from the DDGS can be aspirated. Removal of fiber by aspiration after drying can increase the amount of oil and protein in the residual DDGS, for example, by 0.2 to 1.9% and 0.4 to 1.4%, respectively. The amount of NDF in the residual DDGS can decrease, for example, by 0.1 to 2.8%.

In an embodiment, fractionation can employ the larger fiber and germ pieces to increase the particle size of that part of the DDGS derived from the endosperm, as well as to improve syrup carrying capacity. A ring dryer disintegrator can provide some particle size reduction and homogenization.

Methods and Systems for Drying Wet Cake to Make Distiller's Dried Grains

The beer produced by fermentation includes ethanol, other liquids, and solid material. Centrifugation and/or distillation of the beer can yield solids known as wet cake and liquids known as thin stillage. The wet cake can be dried to produce distiller's dried grain. The thin stillage can be concentrated to a syrup, which can be added to the wet cake or distiller's dried grain and the mixture then dried to form distiller's dried grain plus solubles. The present method can include drying the wet cake to produce distiller's dried grain. The present method can include drying the syrup plus distiller's dried grain to produce distiller's dried grain plus solubles. The distiller's dried grain can be produced from whole grain (e.g., corn) or from fractionated grain (e.g., corn). The present method can produce high protein distiller's dried grain and/or distiller's dried grain with improved physical characteristics. Such distiller's dried grains are described hereinbelow.

Conventional ethanol production processes employed drum dryers. Advantageously, in an embodiment, the present method and system can employ a flash or ring dryer. Flash or ring dryers have not previously been employed in processes like the present one. Configurations of flash and ring dryers are known. Briefly, a flash or ring dryer can include a vertical column through which a pre-heated air stream moves the wet cake. For example, a flash or ring dryer can include one or more inlets that provide entry of heat or heated air into the dryer. This dries the wet cake. The dried wet cake is transported to the top of a column. In a ring dryer, further drying can be accomplished by moving the wet cake through one or more rings connected to the column. For example, a ring dryer can include one or more inlets through which heated air enters a ring structure which propels or circulates the wet cake in or around the ring structure. The dried wet cake can then be pneumatically conveyed to down-stream separating equipment such as a cyclone or dust collector.

The present method can include employing a flash dryer to dry (i.e., flash drying) the wet cake and to produce distiller's dried grain. The present method can include employing a flash dryer to dry (i.e., flash drying) the syrup plus distiller's dried grain to produce distiller's dried grain plus solubles. Employing a flash dryer can produce high protein distiller's dried grain and/or distiller's dried grain with improved physical characteristics. Such distiller's dried grains are described hereinbelow.

The present method can include employing a ring dryer to dry (i.e., ring drying) the wet cake and to produce distiller's dried grain. The present method can include employing a ring dryer (i.e., ring drying) to dry the syrup plus distiller's dried grain to produce distiller's dried grain plus solubles. Employing a ring dryer can produce high protein distiller's dried grain and/or distiller's dried grain with improved physical characteristics. Such distiller's dried grains are described hereinbelow.

The present method can include employing a fluid bed dryer to dry (i.e., fluid bed drying) the wet cake and to produce distiller's dried grain. The present method can include employing a fluid bed dryer to dry (i.e., fluid bed drying) the syrup plus distiller's dried grain to produce distiller's dried grain plus solubles. Employing a fluid bed dryer can produce high protein distiller's dried grain and/or distiller's dried grain with improved physical characteristics. Such distiller's dried grains are described hereinbelow.

The present method can include adding syrup (backset or thin stillage) to the wet cake before, during, or after drying. In an embodiment, the present method includes adding syrup (backset or thin stillage) to the wet cake during drying. For example, the method can include mixing wet cake and syrup in the dryer. For example, the method can include flowing or injecting syrup into the flash, ring, or fluid bed dryer. In an embodiment, the present method includes adding syrup into the column or ring of the dryer in the presence of wet cake and/or distiller's dried grain.

Although not limiting to the present invention, it is believed that flash and/or ring dryers differ from rotary or drum dryers by providing decreased exposure of wet cake to high temperatures of the drying process. A rotary or drum dryer generally has high temperature metal that is in prolonged contact with the wet cake product. It is believed that prolonged contact of this high temperature metal with the wet cake can result in browned, burned, or denatured distiller's dried grains or distiller's dried grains plus solubles. Further, the internal air temperature can be higher in a rotary or drum dryer.

Accordingly, in an embodiment, the present method can include drying the wet cake or wet cake plus syrup for a shorter time than employed with a rotary or drum dryer, and obtaining distiller's dried grain or distiller's dried grain plus solubles that has been sufficiently dried. Accordingly, in an embodiment, the present method can include drying the wet cake or wet cake plus syrup at a lower temperature than employed with a rotary or drum dryer, and obtaining distiller's dried grain or distiller's dried grain plus solubles that has been sufficiently dried. In an embodiment, the method includes changing the drying temperature during drying.

Although not limiting to the present invention, in certain embodiments, such drying systems and methods can provide one or more advantages such as decreased energy consumption in drying, decreased leakage from the drying system.

An embodiment of this invention is the use of flash or ring dryer(s) to change the conditions inside the dryer system to increase or decrease temperature. An embodiment of this invention is the use of flash or ring dryer(s) to change the conditions inside the dryer system to increase or decrease the moisture. An embodiment of this invention is the use of flash or ring dryer(s) to change the conditions inside the dryer system to increase or decrease recycle speed. An embodiment of this invention is the use of flash or ring dryer(s) to change the conditions inside the dryer system to increase or decrease the feed rate into the dryer system.

Continuous Fermentation

The present process can be run via a batch or continuous process. A continuous process includes moving (pumping)

the saccharifying and/or fermenting mixtures through a series of vessels (e.g., tanks) to provide a sufficient duration for the process. For example, a multiple stage fermentation system can be employed for a continuous process with 48-96 hours residence time. For example, reduced plant material (e.g., fractionated plant material) can be fed into the top of a first vessel for saccharifying and fermenting. Partially incubated and fermented mixture can then be drawn out of the bottom of the first vessel and fed in to the top of a second vessel, and so on.

Although not limiting to the present invention, it is believed that the present method is more suitable than conventional methods for running as a continuous process. It is believed that the present process provides reduced opportunity for growth of contaminating organisms in a continuous process. At present, the majority of dry grind ethanol facilities employ batch fermentation technology. This is in part due to the difficulty of preventing losses due to contamination in these conventional processes. For efficient continuous fermentation using traditional liquefaction technology, the conventional belief is that a separate saccharification stage prior to fermentation is necessary to pre-saccharify the mash for fermentation. Such pre-saccharification insures that there is adequate fermentable glucose for the continuous fermentation process.

The present method achieves efficient production of high concentrations of ethanol without a liquefaction or saccharification stage prior to fermentation. This is surprising since this conventional wisdom teaches that it is necessary to have adequate levels of fermentable sugar available during the fermentation process when practiced in a continuous mode. In contrast the present method can provide low concentrations of glucose and efficient fermentation. In the present method, it appears that the glucose is consumed rapidly by the fermenting yeast cell. It is believed that such low glucose levels reduce stress on the yeast, such as stress caused by osmotic inhibition and bacterial contamination pressures. According to the present invention, ethanol levels greater than 18% by volume can be achieved in about 45 to about 96 hours.

Endosperm, Fiber, and Germ Fermentation

In an embodiment, the present process can ferment a portion of a reduced plant material, such as corn. For example, the process can ferment at least one of endosperm, fiber, or germ. The present process can increase ethanol production from such a portion of corn. In an embodiment, the present process can saccharify and ferment endosperm. Endosperm fermentation is lower in free amino nitrogen (FAN) towards the beginning of fermentation due to the removal of germ, which contains FAN. The present process can, for example, preserve the FAN quality of the endosperm compared to conventional high temperature liquefaction. An embodiment of the present invention includes the use of endosperm FAN, which can increase flexibility and efficiency of fermentation.

In an embodiment, the present process can employ endogenous enzyme activity in the grain. In an embodiment, dramatic increase in FAN in whole corn and defibered corn fermentations are reached compared to the initial mash slurry.

Conventional grain dry milling operations separate germ (containing oil) and bran or pericarp (fiber fraction) from the endosperm (starch and protein) portion of the grain using a series of steps and procedures. These steps and procedures include: grain cleaning, tempering, degerming, particle size reduction, roller milling, aspirating, and sifting. This process differs from the traditional wet milling of grains (commonly corn) which are more expensive and water intensive, but capable of achieving cleaner separations of the components of the grain. Dry milling processes offer a version of separating components using lower capital costs for facilities. Also, these processes require less water for operation. The tempering process in dry milling requires less water than required in wet milling.

The competitiveness of dry grain fractionation processes is enhanced when the process of the present invention is utilized for ethanol conversion of these fractions. Traditionally dry milling processes produce various grades of each fraction (germ, bran, and endosperm). In an embodiment, the present method provides bran and endosperm fractions that can be more readily fermented. Depending on the desired purity of each fraction, the fractions can either be pooled to create composites of each stream, or the fractions can be processed individually.

Yeast uses FAN in the present process. In the conventional liquefaction process, FAN levels fall throughout fermentation as yeast cells assimilate and metabolize available FAN during the course of fermentation. Toward the end of fermentation in the conventional process, FAN levels rise illustrating the liberation of cellular FAN coinciding with death and lysis of yeast cells. In contrast, FAN utilization kinetics in the raw starch process is more rapid. FAN levels reach a minimum at least 24 hours earlier, and then begin increasing dramatically. Some of the increase of FAN is due to yeast cell death resulting from the accelerated fermentation.

High Alcohol Beer

The present invention also relates to a high alcohol beer. In an embodiment, the process of the present invention produces beer containing greater than 18 vol-% ethanol. The present process can produce such a high alcohol beer in about 40 to about 96 hours or about 45 to about 96 hours. In an embodiment, the beer includes 18 vol-% to about 23 vol-% ethanol. For example, the present method can produce alcohol contents in the fermenter of 18 to 23% by volume in about 45 to 96 hours.

By way of further example, the present method can produce alcohol content in the fermenter of 18 to 23% by volume in about 45 to 96 hours. In certain embodiments, the majority of the alcohol (80% or more of the final concentration) is produced in the first 45 hours. Then, an additional 2 to 5 vol-% alcohol can be produced in the final 12-48 hours. Concentrations of ethanol up to 23 vol-% can be achieved with fermentation time up to 96 hours. It can be economically advantageous to harvest after 48 to 72 hours of fermentation to increase fermenter productivity.

The present beer can include this high level of ethanol even when it includes high levels of residual starch. For example, the present beer can include ethanol at 18 to 23 vol-% when it contains 0 to 30% residual starch. The present beer can contain residual starches as low as 0% to as high as 20% residual starch.

By conventional measures, high levels of residual starch indicate inefficient fermentation, which yields only low levels of ethanol. In contrast, although not limiting to the present invention, it is believed that the present method results in fewer Maillard type reaction products and more efficient yeast fermentation (e.g., reduced levels of secondary metabolites). This is believed to be due to the low glucose levels and low temperatures of the present method compared to conventional saccharification and liquefaction. Thus, the present method can produce more alcohol even with higher levels of residual starch.

In an embodiment, the present beer includes fewer residual byproducts than conventional beers, even though residual starch can be higher. For example, residual glucose, maltose, and higher dextrins (DP3+) can be as much as 0.8 wt-% lower than in conventional beers produced under similar fermentation conditions. By way of further example, residual glycerol can be as much as 0.7 wt-% less. Lactic acid and fusel oils can also be significantly reduced. For example, the present beer can include less than or equal to about 0.2 wt-% glucose, about 0.4 wt-%, about 0.1 wt-% DP3, undetectable DP4+, 0.7 wt-% glycerol, about 0.01 wt-% lactic acid, and/or about 0.4 wt-% fusel oils.

Distiller's Dried Grain

High Protein Distiller's Dried Grain

The present invention also relates to a distiller's dried grain product. The distiller's dried grain can also include elevated levels of one or more of protein, fat, fiber (e.g., neutral detergent fiber (NDF)), and starch. For example, the present distiller's dried grain can include 34 or more wt-% protein, about 25 to about 60 wt-% protein, about 25 to about 50 wt-% protein, or about 30 to about 45 wt-% protein. In certain circumstances the amount of protein is about 1 to about 2 wt-% more protein than produced by the conventional process. For example, the distiller's dried grain can include 15 or more wt-% fat, about 13 to about 17 wt-% fat, or about 1 to about 6 wt-% more fat than produced by the conventional process. For example, the distiller's dried grain can include 31 or more wt-% fiber, about 23 to about 37 wt-% fiber, or about 3 to about 13 wt-% more fiber than produced by the conventional process. For example, the distiller's dried grain can include 12 or more wt-% starch, about 1 to about 23 wt-% starch, or about 1 to about 18 wt-% more starch than produced by the conventional process.

In an embodiment, the present distiller's dried grain includes elevated levels of B vitamins, vitamin C, vitamin E, folic acid, and/or vitamin A, compared to conventional distiller's dried grain products. The present distiller's dried grain has a richer gold color compared to conventional distiller's dried grain products.

Distiller's Dried Grain With Improved Physical Characteristics

The present invention also relates to a distiller's dried grain with one or more improved physical characteristics, such as decreased caking or compaction or increased ability to flow. The present process can produce such an improved distiller's dried grain.

Although not limiting to the present invention, it is believed that the present process can produce fermentation solids including higher molecular weight forms of carbohydrates. Such fermentation solids can, it is believed, exhibit a higher glass transition temperature (i.e. higher $T_g$ values) compared to solids from the conventional process. For example, residual starches can have a high $T_g$ value. Thus, through control of starch content in the DDG and DDGS, the present process can manufacture DDG or DDGS with target $T_g$ values.

Further, according to the present invention, adding an alkaline syrup blend (e.g., syrup plus added lime or other alkaline material) to the fermentation solids (e.g., distiller's dried grains) can provide decreased caking or compaction or increase ability to flow to the distiller's dried grain with solubles (DDGS).

Although not limiting to the present invention, it is believed that organic acids such as lactic, acetic, and succinic acids which are produced in fermentation have a lower $T_g$ value than their corresponding calcium salts. Maintenance of residual carbohydrate in higher molecular weight form, or addition of lime to form calcium salts of organic acids, are two strategies for forming higher $T_g$ value co-products that will be less likely to undergo the glass transition, resulting in the deleterious phenomenon known as caking.

In an embodiment, DDG or DDGS of or produced by the method of the present invention flows more readily than DDG or DDGS produced by the conventional process.

Although not limiting to the present invention, it is believed that process of the present invention can need not destroy protein in the fermented plant material (e.g., fractionated plant material). Corn contains prolamins, such as zein. Grain sorghum, for example, contains a class of zein-like proteins known as kafirins, which resemble zein in amino acid composition. The thermal degradation that occurs during liquefaction, distillation, and high temperature drying produces DDG and DDGS including significant amounts of degraded protein. It is believed that the process of the present invention can provides improved levels of the prolamin fraction of cereal grains.

It is believed that extended exposure to high alcohol concentrations that can be achieved by the present process can condition the proteins in the plant material (e.g., fractionated plant material). This can solubilize some of the proteins. For example, it is believed that in distillation the ethanol concentration reaches levels that can solubilize prolamins (e.g., zein) in the beer. Upon the removal, or "stripping," of ethanol from the beer, prolamins (such as zein) can be recovered in concentrated form in DDG and DDGS. The resulting high protein content of DDG and DDGS can be advantageous for various end uses of DDG and DDGS, for example in further processing or compounding.

In an embodiment, efficient fermentation of the present process removes from the DDG or DDGS non zein components such as starch. Fractionating the plant material, e.g., corn, can also increase levels of proteins, such as zein, in the DDG or DDGS. For example, removing the bran and germ fractions prior to fermentation can concentrate zein in the substrate. Zein in corn is isolated in the endosperm. Fermentation of zein enriched endosperm results in concentration of the zein in the residuals from fermentation.

In an embodiment, the present method can operate on fractionated plant material (such as endosperm, fiber, other parts of cereal grain) to provide a protein enriched solid product from fermentation. For example, the present method operated on fractionated plant material can produce a DDG enriched in prolamin, such as zein.

In an embodiment, the process of the present invention can provide DDG and DDGS with different, predetermined $T_g$ values. The process of the present invention can ferment fractions containing high, medium, or low levels of zein, thus varying the glass transition temperature of the resulting DDG or DDGS. The resulting co-product $T_g$ can be directly proportional to the prolamin protein (such as zein) content. The process of the current invention is desirable for the fermentation of high protein corn. This also allows production of DDG and DDGS with a higher prolamin (zein) content.

Residual starch remaining at the end of fermentation preferentially segregates into the thin stillage fraction, which is subsequently evaporated to produce syrup. The wet cake fraction produced by the present method, which can be dried separately to produce DDG, can be higher in prolamin protein (such as zein) than conventional DDG. The present process allows syrup and wet cake blend ratios to be varied. This results in DDG/DDGS with varying ratios of prolamin protein (such as zein) and residual starch. As the residual starch in the wet cake reduces the protein in the wet cake increases. This indicates an inverse relationship. A similar response occurs in the syrup fraction.

It is believed that starch can segregate into the liquid fraction. The amount of starch in the DDGS can be varied by blending syrup at rates ranging from 0 lbs. dry weight of syrup solids to 1.2 lbs. of syrup solids per lb. of wet cake solids before, and various times during drying to create the final DDGS product. The disproportionate segregation of residual starches into the backset or thin stillage fraction can provide both the aforementioned burn-out and secondary fermentation to be performed on these fractions. Since the thin stillage is evaporated to produce syrup, the centrifuge mass balance also enables DDGS production at various $T_g$ values depending on the desired properties and their dependence on $T_g$.

Emissions

The present invention has emissions benefits. Emissions benefits result in the reduction in byproducts created in the ethanol manufacturing process. There is a marked reduction in extraction of fats and oils in the mash from the germ fraction of cereal grains. There is a reduction of byproducts from Maillard reactions typically formed during cooking and liquefaction. And there is a reduction in fermentation byproducts. These observations result in reduced emissions during the recovery of co-products. The concentration and emission rates of volatile organic compounds (VOC), carbon monoxide (CO), nitric oxide compounds (NOx), sulfur oxides (e.g., $SO_2$), and other emissions are considerably lower. See Table 1. Note that other manufacturers have attempted to lower emissions by manufacturing wet cake instead of drying to DDG or DDGS.

The present invention also relates to volatile organic compounds (VOC), such as those produced by drying products of a fermentation process. The present method includes producing ethanol, distiller's dried grain, and additional useful fermentation products with production of lower levels of VOC compared to conventional processes. For example, in the present method, drying distillation products (e.g., spent grain) produces reduced levels of VOC.

Conventional fermentation processes using corn, for example, produces about 2.1 pounds of VOC's from drying distillation products from each ton of corn processed. The actual stack emissions can be less due to pollution control equipment. The present method results in at least 30% reduction in VOC production to about 1.47 or less pounds per ton of corn processed. These emissions reductions are unexpected yet highly significant, and provide for more efficient use of emissions reduction control technology, such as thermal oxidizers.

VOC produced by fermentation processes include ethanol, acetic acid, formaldehyde, methanol, acetaldehyde, acrolein, furfural, lactic acid, formic acid, and glycerol.

The present invention also relates to carbon monoxide (CO), such as those produced by drying products of a fermentation process. The present method includes producing ethanol, distiller's dried grain, and additional useful fermentation products with production of lower levels of CO compared to conventional processes. For example, in the present method, drying distillation products (e.g., spent grain) produces reduced levels of CO.

Conventional fermentation processes using corn, for example, produces about 1.4 pounds of CO's from drying distillation products from each ton of corn processed. The actual stack emissions can be less due to pollution control equipment. The present method results in a 30% reduction in CO production to about 0.98 or less pounds per ton of corn processed. These emissions reductions are unexpected yet highly significant, and provide for more efficient use of emissions reduction control technology, such as thermal oxidizers.

TABLE 1

| Emissions Reductions | | | | | |
|---|---|---|---|---|---|
| Emission Type | | Units | Conventional Run | Inventive Process | Emissions Reduction % |
| VOC | Concentration | ppmv lb/dscf | 663 | 459.65 | 30.67 |
| | Emission Rate | lb/hr | 13.35 | 7.91 | 40.75 |

TABLE 1-continued

| Emissions Reductions | | | | | |
|---|---|---|---|---|---|
| Emission Type | | Units | Conventional Run | Inventive Process | Emissions Reduction % |
| CO | Concentration | ppmv lb/dscf | 434 | 234.13 | 46.05 |
| | Emission Rate | lb/hr | 9.1 | 4.94 | 45.71 |

System for Producing Ethanol

In an embodiment, the invention relates to a system that produces ethanol. The present system can include a saccharification apparatus 1, a fermentation apparatus 2, a distillation apparatus 3, and a dryer apparatus 4.

The saccharification apparatus 1 can be any of a variety of apparatus suitable for containing or conducting saccharification. The saccharification apparatus 1 can be, for example, a vessel in which reduced plant material can be converted to a sugar, which can be fermented by a microorganism such as yeast. The saccharification apparatus 1 can be configured to maintain a saccharification mixture under conditions suitable for saccharification. The saccharification apparatus 1 can be configured to provide for the conversion of reduced plant material with the addition of enzymes. In an embodiment, the saccharification apparatus 1 is configured for mixing reduced plant material with a liquid and adding a saccharifying enzyme composition to the liquid. In an embodiment, the saccharification apparatus 1 is configured for saccharification at a variety of pHs and temperatures, but preferably at a pH of 6.0 or less, and at a temperature of about 25 to about 40° C.

The fermentation apparatus 2 can be any of a variety of apparatus suitable for containing or conducting fermentation. The saccharification apparatus 1 can be, for example, a vessel in which sugar from reduced plant material can be fermented to ethanol. The fermentation apparatus 2 can be configured to maintain a fermentation mixture under conditions suitable for fermentation. In an embodiment, the fermentation apparatus 2 can be configured for fermenting through use of a microorganism, such as yeast. In an embodiment, the fermentation apparatus 2 can be configured to ferment a starch composition that has not been cooked, specifically the saccharification mixture. In an embodiment, the apparatus can employ any variety of yeasts that yields a commercially significant quantity of ethanol in a suitable time. Yeast can be added to the apparatus by any of a variety of methods known for adding yeast to a system that conducts fermentation. The fermentation apparatus 2 can be configured for fermentation for about 25 to 150 hours at a temperature of about 25 to about 40 degrees C.

The saccharification apparatus 1 and the fermentation apparatus 2 can be a single, integrated apparatus. In an embodiment, this apparatus is configured to provide higher temperatures early on during simultaneous conversion of reduced plant material to sugars and fermentation of those sugars. In an embodiment, this apparatus is configured to provide lower temperatures later during the simultaneous saccharification and fermentation. The apparatus also may utilize the reagents and conditions described above for saccharification and fermentation, including enzymes and yeast.

The distillation apparatus 3 can be any of a variety of apparatus suitable for distilling products of fermentation. The distillation apparatus 3 can be, for example, configured to recover ethanol from the fermentation mixture ("beer"). In an embodiment, the fermentation mixture is treated with heat prior to entering the distillation apparatus 3. In another embodiment, fractions of large pieces of germ and fiber are removed with a surface skimmer or screen prior to or after entering the distillation apparatus 3.

The dryer apparatus 4 can be any of a variety of apparatus suitable for drying solids remaining after distillation (and optional centrifugation, for example, in a centrifuge system). In an embodiment, the dryer apparatus 4 is configured to dry recovered solids, which can result in production of distiller's dried grain. After the distillation system separates the ethanol from the beer, recovered solids remain. These recovered solids can then be dried in the dryer apparatus 4. This produces distiller's dried grain and/or distiller's dried grain plus solubles. In an embodiment, the dryer apparatus 4 can be or include a ring dryer. In an embodiment, the dryer apparatus 4 can be or include a flash dryer. In an embodiment, the dryer apparatus 4 can be or include a fluid bed dryer.

Endogenous Enzyme

In certain embodiments, the present invention includes methods of fermenting plant material (e.g., corn) that result in enhanced ethanol yields by the use of lower drying temperatures and endogenous enzyme activity. The drying of plant material (e.g., corn) at high temperatures can damage the extractable starch content, resulting in lower starch yields in wet milling. For example, high temperature drying can decrease starch yield (accessibility) and endogenous enzyme activity (proteases and alpha-glucosidases). Although not limiting to the present invention, it is believed that the inactivation of endogenous protease can reduce the formation of free amino acids. Amino acids are yeast nutritional factors for high gravity fermentation. Although not limiting to the present invention, it is believed that the inactivation of endogenous protease can reduce the formation of free amino nitrogen (FAN). FAN is a known yeast nutritional factor for high gravity fermentation. Although not limiting to the present invention, it is believed that inactivating native alpha-glucosidases can reduce the formation of supplemental glucose.

In an embodiment, the present process can employ endogenous enzyme activity in the plant material (e.g., grain). It is known, for example, that plant material (e.g., corn) possesses endogenous alpha-glucosidase and protease activity. It has been discovered that partially or fully preserving the activity of one or more endogenous enzymes is advantageous in achieving improved fermentation performance and ethanol yield.

In an embodiment, endogenous alpha-glucosidase activity is employed in the fermentation process. It is believed that endogenous alpha-glucosidase activity increases the formation of supplemental glucose, and that supplemental glucose improves the performance of the process of the invention. It is further believed that supplemental glucose improves the performance of exogenous enzymes added during the fermentation process.

In an embodiment, endogenous protease activity is employed in the fermentation process. Although not limiting to the present invention, it is believed that the FAN increase in an embodiment of the present method can result from the action of endogenous proteases in plant material (e.g., corn). Accordingly, in certain embodiments, additional nitrogenous sources in the present method do not show the same level of positive effect as they do in the conventional process. Although not limiting to the present invention, it is believed that embodiments of the present method are more self-sufficient in utilizable FAN, and possibly other nutrients for the yeast. Accordingly, in certain embodiments, the glycerol levels are reduced compared to conventional processes.

The presence of increased FAN levels can be advantageous in achieving improved ethanol yield without increasing glycerol production. Ethanol and glycerol formation can be tightly coupled; the higher the ethanol concentration, the greater the glycerol concentration. Glycerol is used to regenerate NADH for continued glycolysis and fermentation. When extra FAN is present, such as that generated from endogenous protease, the relationship between glycerol formation and ethanol formation can be decoupled, and it is possible to achieve higher ethanol concentrations without the concomitant increase in glycerol formation.

In an embodiment, the enzyme activity of one or more endogenous enzymes present in the plant material (e.g., grain) is partially or fully preserved by optimizing the temperature range used when drying the plant material (e.g., grain). It has surprisingly been discovered that reducing the temperature at which plant material (e.g., grain) is dried can increase fermentation performance and ethanol production. It is believed that the use of lower drying temperatures preserves endogenous enzyme activity.

In an embodiment, the enzyme activity of one or more endogenous enzymes present in the plant material (e.g., grain) is partially or fully preserved by using plant material (e.g., corn) having a lower initial moisture content. It has been discovered that low moisture plant material (e.g., corn) hybrids produce higher ethanol yields in a process of the invention. It is believed that drying of low-moisture plant material (e.g., corn) can result in less inactivation of endogenous enzyme activity in the plant material (e.g., grain). Furthermore, low-moisture plant material (e.g., corn) requires less time to dry at a given temperature, resulting in a reduced opportunity for starch damage or enzyme denaturation to occur.

In an embodiment, a process of the invention includes the step of selecting plant material (e.g., corn) that has a lower initial moisture content and drying the plant material (e.g., corn) at a reduced temperature. This can decrease the variability in processing a given batch. It has been discovered that drying plant material (e.g., grain) at a reduced temperature can reduce variability in plant material (e.g., grain) processability. A positive correlation exists between the temperature at which plant material (e.g., corn) is dried and the level of variability in plant material (e.g., corn) processability, as measured by the yield of ethanol product. Although not limiting to the present invention, it is believed that the lower moisture hybrids exhibited less impact from drying temperature. Although not limiting to the present invention, it is believed that the lower the initial moisture of the plant material (e.g., corn), the lower the impact of high temperature drying on the plant material (e.g., grain).

In an embodiment, the present method can employ reducing glycerol concentrations through the addition of osmoprotectants.

In an embodiment, the present method can employ the endogenous enzyme activity of germinated plant material (e.g., grain). The method can include steeping the plant material (e.g., grain) under controlled conditions to increase the moisture content and oxygenating to stimulate the dormant kernel's natural metabolic processes, which function to increase enzyme activity in the aleurone layer. The kernel can then be allowed to germinate. In such an embodiment, it is believed that enzymes such as β-amylase, protease (exo-peptidase, carboxy-peptidase, and endo-proteases), β-glucanase, α-amylase, and pentosanase are formed in the aleurone layer. Formation and induction (activation) of these enzymes can be promoted by the moisture and oxygen present in the steep tank. Endogenous enzyme activity can increase (e.g., 5× to 15×) during the germination process.

In an embodiment, whole plant material (e.g., grain, such as, corn) can be rinsed in a dilute solution of an antimicrobial (e.g., anthium dioxide) to reduce the bacterial load. The plant material (e.g., grain, such as, corn) can then be rinsed with water and infused with air in one or more steep tanks for about ~24 hours. This can induce germination. After steeping, the moistened and swollen kernels can be ground in a wet mill mill to separate the fiber from the endosperm and germ components. Separation of fiber and germ is possible, but not necessary, prior to fermentation. This embodiment of the method can induce the endogenous enzymes in the plant material (e.g., grain, such as, corn), effectively increasing their concentration.

Although not limiting to the present invention, it is believed that starch accessibility can be enhanced through the steeping and/or germination process. It is further believed that such a method can effectively produce high levels of ethanol employing a coarser grind of plant material (e.g., grain) than previous methods for raw starch hydrolysis. Further, although not limiting to the present invention, it is believed that induction of native fiber degrading enzymes can improve ethanol yield from the cellulose fraction.

In an embodiment, the fiber and germ components can be floated off the endosperm substrate prior to fermentation if a finer grind is desired for the endosperm fraction. In an embodiment, separation of the fiber and germ post fermentation and/or drying allows conversion of the starch typically lost to these fractions. In an embodiment, separation of the fiber and germ post fermentation and/or drying allows co-products (e.g., DDG or DDGS) to be obtained which are enhanced in one or more component. In an embodiment, all of the plant material (e.g., grain) can be fermented together in a one step "brew", followed by separation of fiber and germ via elutriation and sieving post ethanol recovery.

In an embodiment, a coarse grind can provide clarification efficiencies, and minimize the formation of solubles which occurs when plant material (e.g., corn) is ground to a finer particle size. In an embodiment, a coarser grinds can provide advantageous DDG/DDGS.

In certain embodiments, the present method provides advantageous fouling characteristics, changes in the viscosity/cooling capacity, increased settling/sedimentation of insoluble fiber components in fermenters, and/or heat exchanger cleanliness.

In an embodiment, the present method can employ germination and increase the lysine and tryptophan content of the plant material (e.g., grain). In an embodiment, the process of germination can be accelerated by naturally occurring plant growth regulators known as gibberellin.

Phytate is an antinutritional factor present in cereal plant material (e.g., grain). Several methods exist for decreasing the phytate content of cereals, including methods to stimulate the activity of phytase enzymes, which hydrolyze phytate to remove inorganic phosphate from the myo-inositol phosphate ring, and thus reduce its mineral binding capacity. In an embodiment of the present method, endogenous cereal phytase can be activated by soaking, germination or fermentation, and employed for the benefit of the process.

In an embodiment, the present method including germination can be employed to provide enhanced levels of bioactive products, such as, for example, gamma amino butyric acid (e.g., from wheat) or saponins, oestrogenic compounds, almost all phytosterols, as well as several enzymes (e.g., from soy).

The present invention may be better understood with reference to the following examples. These examples are intended to be representative of specific embodiments of the invention, and are not intended as limiting the scope of the invention.

EXAMPLES

Example 1

Production of Improved Distiller's Dried Grain from Corn

A method according to the present invention was employed to produce distiller's dried grain from corn. This method produced high protein, high fat, and high fiber distiller's dried grain. Comparison with a conventional saccharification and liquefaction process indicates superior performance of the present method.

Materials and Methods
Raw Starch Fermentation

Yeast inoculum was prepared by adding glucoamylase (0.088 ml of Novozymes' Spirizyme Plus gluco-amylase at 400 AGU/g) and protease (0.018 ml of Genencor International's GC 106 protease 1000 SAPU/g) to 400 ml of stillage containing 70 grams of maltodextrin. Stillage (backset) used was prepared from prior conventional or raw starch fermentations by distilling off the alcohol and subjecting the resulting whole stillage to centrifugal separation to produce backset. 1.07 grams of urea, 0.13 grams of zinc sulfate, and 0.00067 ml of a 1:1000 dilution of Antibiotic (Alltech Lactocide) were also added. About 300-400 million cells/ml of viable cells of yeast (*Saccharomyces cervisiae*) (0.48 g of Fleischmann's Fali yeast) was added to this mixture and propagation was conducted without stirring, or agitating, for 8 hours at an incubation temperature of 90° F. Flasks were periodically swirled under gentle conditions to effect mixing of the contents. The resulting yeast culture (10.8 ml) was added directly to each fermenter for inoculation.

Corn was obtained from commercial suppliers of seed corn and was ground through a 0.5 mm screen using a hammer mill prior to fermentation. Several varieties of conventional number 2 yellow dent corn were compared, and in several experiments their isogenically equivalent of waxy corn was also tested. Different corn varieties were tested to demonstrate that the present methods produce improved DDG using any of a variety of corn hybrids.

Approximately 129 to 134 grams of the appropriate corn was mixed in about 225 ml of water. Actual grams of flour (ground corn) and water volumes were adjusted for each fermenter based on the moisture content of the flour so that all fermentations were run at approximately 33.4 grams of dry solids corn per 100 grams of water (33.4% DSC). All raw starch fermenters were adjusted to pH 5.0 with sulfuric acid.

Fermentations were conducted at 82° F. Antibiotic (Alltech Lactocide. 3 mg) was added to each fermentation batch. The raw starch fermentations employed a commercially available glucoamylase preparation (Novozymes' Spirizyme Plus 0.317 ml of GAU/ml) which also includes acid fungal amylase activity.

Fermentations were conducted for 72 hours with sampling conducted at approximately 24 (e.g. 25) hour intervals. All samples were analyzed by HPLC. At the end of fermentation beer samples were placed in metal pans, pH was decreased to <3.5 to inactivate residual enzyme activity, and dried.
Conventional Fermentation Preparation of yeast inoculum and grinding of corn to corn flour was accomplished as described above for the raw starch fermentation.

For fermentations employing the conventional process, pH adjustment was not necessary; the natural pH of the water and corn flour was 5.8 to 6.0. The conventional fermentations started with a saccharification or cooking stage to liquefy the starch in the mixture. The cook stage was conducted for 60 minutes at a temperature of 85° C. 0.044 ml of Novozymes Liquozyme SC Alpha-amylase (0.044 ml of Novozymes Liquozyme SC 120 AFAU (KNU)/ml) was added to liquefy the corn mash.

Conventional fermentations were also run at 82° F. and included Antibiotic (3 mg of Alltech Lactocide antibiotic). Protease (0.0047 ml of GC 106 protease (1000 SAPU/g/ml) and 0.64 ml of 50% urea liquor (50% of industrial grade urea) were added to fermenters using the conventional process. A commercially available glucoamylase (0.095 ml of Genencor International's GC 480 glucoamylase at 400 AGU/ml) was added for fermentation. Otherwise, fermentations were generally conducted as described above for raw starch fermentations.
Results and Discussion Fermentation Results are shown in Table 2 and summarized in Table 3.

TABLE 2

Comparison of Process Impacts on Proximate Analysis of DDGS

| Corn Hybrid | Residual Sugars as Glucose (%) | | % Acids Lactic & Acetic | | % Glycerol | | % Starch | | % Protein | | % Fat | | % NDF | |
|---|---|---|---|---|---|---|---|---|---|---|---|---|---|---|
| | Conv | RSH | Conv | RSH | Conv | RSH | Conv | RSH | Conv | RSH | Conv | RSH | Conv | RSH |
| #2 Yellow Hybrid A | 2.57 | 0.58 | 0.09 | 0.06 | 1.09 | 0.86 | 6.86 | 22.24 | 31.25 | 32.15 | 11.05 | 13.65 | 20.45 | 29.00 |
| #2 Yellow Hybrid B | 1.67 | 0.84 | 0.09 | 0.06 | 1.12 | 0.77 | 2.78 | 21.14 | 31.90 | 33.20 | 13.30 | 17.00 | 24.90 | 32.30 |
| Waxy Isogenic Pair to Hybrid B | 1.70 | 2.11 | 0.10 | 0.06 | 1.11 | 0.75 | 1.97 | 14.35 | 31.10 | 30.40 | 14.30 | 16.40 | 25.30 | 34.10 |
| #2 Yellow Hybrid C | 1.18 | 0.62 | 0.08 | 0.06 | 1.20 | 0.85 | 1.68 | 17.51 | 31.50 | 33.80 | 15.00 | 21.30 | 22.00 | 31.00 |
| Waxy Isogenic Pair to Hybrid C | 1.43 | 1.49 | 0.10 | 0.07 | 1.13 | 0.82 | 1.79 | 9.92 | 30.00 | 29.70 | 15.20 | 17.10 | 24.60 | 37.40 |
| #2 Yellow Hybrid D | 0.84 | 0.49 | 0.06 | 0.05 | 1.03 | 0.74 | 0.83 | 14.61 | 36.40 | 37.60 | 11.90 | 14.80 | 23.40 | 28.90 |
| Waxy Isogenic Pair to Hybrid D | 0.58 | 0.89 | 0.06 | 0.07 | 1.06 | 0.78 | 1.11 | 3.39 | 33.30 | 34.20 | 12.80 | 15.70 | 24.60 | 31.70 |
| Waxy Hybrid E | 1.15 | 0.50 | 0.10 | 0.06 | 1.11 | 0.76 | 0.65 | 1.90 | 35.60 | 35.90 | 11.60 | 13.30 | 26.90 | 29.90 |
| #2 Yellow Hybrid F | 1.86 | 0.61 | 0.11 | 0.07 | 1.17 | 0.78 | 3.27 | 15.99 | 31.80 | 31.10 | 12.50 | 13.30 | 28.10 | 33.10 |
| Waxy Hybrid G | 1.23 | 0.97 | 0.12 | 0.09 | 1.11 | 0.84 | 10.49 | 1.04 | 39.70 | 41.10 | 12.10 | 14.00 | 20.30 | 23.70 |
| Hetero Waxy Isogenic Pair to Hybrid G | 1.14 | 0.39 | 0.10 | 0.07 | 1.05 | 0.84 | 12.15 | 13.74 | 36.60 | 38.90 | 8.96 | 10.90 | 20.80 | 26.50 |
| Averages | 1.40 | 0.86 | 0.09 | 0.07 | 1.11 | 0.80 | 3.96 | 12.35 | 33.56 | 34.37 | 12.61 | 15.22 | 23.76 | 30.69 |

TABLE 3

Comparison of Process Impacts on Proximate Analysis of DDGS (Summary)

| Proximate Analysis | Process | |
|---|---|---|
| | Conventional | Raw Starch |
| Starch | 3.96 | 12.35 |
| Protein | 33.56 | 34.37 |
| Fat | 12.61 | 15.22 |
| Fiber | 23.76 | 30.69 |
| Ash | 4.06 | 4.29 |
| Unknown | 22.05 | 3.08 |
| Summation | 100.00 | 100.00 |

An interesting feature of the raw starch process is that it results in distiller's dried grain with solubles (DDGS) with equal or higher levels of several components, even when it appears that fermentation efficiency, as measured by residual starch, was decreased for the raw starch process. One would expect that, with the lower efficiency, the other components of the DDGS would be lower based on mass balance. The raw starch process apparently results in less damage to the constituents of the grain.

Another interesting feature of the raw starch process is the performance improvement realized using waxy corn hybrids. Waxy corn is almost entirely comprised of amylopectin starch, whereas normal #2 yellow corn is about 25 to 28% amylose starch with the remainder being amylopectin. Waxy corn is generally not used in the conventional process because of the high peak viscosity and more rapid rate of viscosity development compared to regular corn. The high initial viscosity makes the corn slurry more difficult to pump during the initial primary high temperature liquefaction. Waxy corn varieties can, however, be readily employed in the present process. Because no cook stage is employed, the high peak viscosity is not a processing issue.

Example 2

The Present Process Provides Improved Yield Potential

The yield potential of the method of the present invention was compared to a conventional process. The present method exhibited improved yield using temperature staging. The present method exhibited an increased potential maximum yield for ethanol production. Comparison with conventional saccharification and liquefaction process indicates superior performance of the present method.

Materials and Methods

Fermentations were prepared in a similar manner as in Example 1 except for intentional differences in particle size, alpha amylase enzyme dose, gluco-amylase enzyme dose, or acid fungal amylase enzyme dose. Conditions for this experiment are described in Table 4. Corn for all tests was obtained from Broin Enterprises (BEI), Scotland, S. Dak., USA. Corn representing a coarse particle size by raw starch standards was ground at BEI. Finely ground corn was produced using a lab hammer mill through a 0.5 mm screen.

The conventional process utilized indicated levels of Liquozyme SC and GC 480. The raw starch process used indicated levels of Spirizyme Plus and SP 288 acid fungal amylase at 1700 AFAU's per gm. Dosages of urea liquor, zinc sulfate, and antibiotic were adjusted accordingly for the conventional process. Stillage (backset) used was prepared from prior conventional or raw starch fermentations by distilling off the alcohol and subjecting the resulting whole stillage to centrifugal separation to produce backset. Fermentation temperatures were staged according to the following set points: 0-18 hours at 90° F., 18-42 hours at 86° F., and 42-72 hours at 82° F. Samples were taken at 65 hours to represent the end of fermentation.

Results and Discussion

The objective of these experiments was to illustrate the sensitivities of the two processes to changes in enzyme dose rate and compare differences in ethanol % and residual starch. The results are shown in Table 4 and FIGS. 1A, 1B, 1C, 1D and 1E. The impact of grind size and enzyme dose on the two processes is apparent. Note that SP 288 acid fungal amylase is effective at accessing raw starch. Acid fungal amylase appears to improve the ability to access starch such that grind size has less effect on yield when SP 288 is present. The present process achieved significantly better alcohol yields at equivalent or higher residual starch levels. FIG. 1B illustrates a similar effect of grind size on ethanol yield in the conventional process, and demonstrates the importance of GA dosage level on accessing starch in coarse grain particles.

Extrapolation of the results for both the conventional and raw starch process shown in FIGS. 1A and 1B to zero residual starch reveals an embodiment of the raw starch process. As residual starch levels decrease based on improving conversion efficiencies, this process can achieve higher ethanol % than the conventional process. For example, in the absence of residual starch, the present process in this example would produce 21.3 vol-% ethanol, but the conventional process would produce only 20.6 vol-% ethanol. Such an increase is significant. The present process potential of the new process compared to the existing process is shown in FIGS. 1C and 1D. These figures summarize the results for both processes run under the varying grind size and enzyme dosage combinations. FIG. 1C illustrates the potential for the new process to produce more alcohol than the conventional process, even when residual starch levels are higher. Conventional wisdom would suggest the raw starch process is less efficient due to the higher levels of residual starch, however, this is not the case. The present process is superior to the conventional method. Note that fermentation efficiency can also be assessed by examining the fermentation drop solids. This is shown in the composite data comparing both processes in FIG. 1D. Since all fermentations in the above example were started at the same initial set solids, a lower drop solids suggests a more efficient conversion of starch to ethanol. The potential of this process is also indicated by the achievement of an equal to or reduced level of drop solids, despite the higher residual starches observed.

FIG. 1E shows the temperature staging done during the present process. Fermentation temperatures were staged according to the following set points: 0-18 hours at approximately 90° F. (ranging from about 95° F. to about 90° F.), 18-42 hours at approximately 86° F. (ranging from 90° F. to 86° F.), and 42-72 hours at about 82° F. (ranging from 86° F. to 84° F.). Staging of temperature helps to increase ethanol production process by reducing stress on yeast. The temperature is decreased as ethanol is produced to reduce the stress on yeast caused by ethanol production.

TABLE 4

Comparison of the Yield Potential of Conventional vs. Raw Starch Processes

Conventional Fermentation Process

| Grind Used | Enzyme Dosages | | Process Water Amounts | | Corn | Slurry | | | Residual Starch |
|---|---|---|---|---|---|---|---|---|---|
| | AA (ml) | GA (ml) | Water (ml) | Backset % | Flour Wt. % | Dry Solids | AA Dose | Ethanol Vol % | Dry Wt. % |
| BEI | 0.04 | 0.08 | 285 | 40 | 190 | 35.91 | Low | 16.21 | 19.49 |
| BEI | 0.04 | 0.12 | 285 | 40 | 190 | 35.89 | Low | 17.57 | 14.69 |
| BEI | 0.06 | 0.08 | 285 | 40 | 190 | 35.90 | Medium | 16.22 | 15.14 |
| BEI | 0.06 | 0.12 | 285 | 40 | 190 | 35.89 | Medium | 17.12 | 14.03 |
| BEI | 0.08 | 0.08 | 285 | 40 | 190 | 35.89 | High | 15.93 | 16.72 |
| BEI | 0.08 | 0.12 | 285 | 40 | 190 | 35.88 | High | 17.47 | 12.78 |
| 0.5 mm | 0.04 | 0.08 | 295 | 40 | 176 | 35.85 | Low | 16.78 | 15.64 |
| 0.5 mm | 0.04 | 0.12 | 295 | 40 | 176 | 35.83 | Low | 18.40 | 9.58 |
| 0.5 mm | 0.06 | 0.08 | 295 | 40 | 176 | 35.84 | Medium | 16.57 | 15.77 |
| 0.5 mm | 0.06 | 0.12 | 295 | 40 | 176 | 35.83 | Medium | 18.19 | 10.36 |
| 0.5 mm | 0.08 | 0.08 | 295 | 40 | 176 | 35.83 | High | 16.92 | 16.48 |
| 0.5 mm | 0.08 | 0.12 | 295 | 40 | 176 | 35.82 | High | 18.31 | 9.27 |

Raw Starch Fermentation Process

| Grind Used | Enzyme Dosages | | Process Water Amounts | | Corn | Slurry | | | Residual Starch |
|---|---|---|---|---|---|---|---|---|---|
| | AA (ml) | GA (ml) | Water (ml) | Backset % | Flour Wt. % | Dry Solids | GA Dose | Ethanol Vol % | Dry Wt. % |
| BEI | 0.00 | 0.34 | 285 | 40 | 190 | 36.35 | Low | 17.53 | 22.37 |
| BEI | 0.03 | 0.34 | 285 | 40 | 190 | 36.35 | Low | 19.19 | 14.45 |
| BEI | 0.00 | 0.42 | 285 | 40 | 190 | 36.32 | Medium | 17.82 | 19.65 |
| BEI | 0.03 | 0.42 | 285 | 40 | 190 | 36.32 | Medium | 19.14 | 11.15 |
| BEI | 0.00 | 0.53 | 285 | 40 | 190 | 36.28 | High | 18.11 | 19.83 |
| BEI | 0.03 | 0.53 | 285 | 40 | 190 | 36.28 | High | 19.13 | 12.80 |
| 0.5 mm | 0.00 | 0.34 | 295 | 40 | 176 | 36.31 | Low | 18.20 | 19.30 |
| 0.5 mm | 0.03 | 0.34 | 295 | 40 | 176 | 36.31 | Low | 19.22 | 13.54 |
| 0.5 mm | 0.00 | 0.42 | 295 | 40 | 176 | 36.28 | Medium | 18.51 | 17.24 |
| 0.5 mm | 0.03 | 0.42 | 295 | 40 | 176 | 36.28 | Medium | 19.56 | 10.50 |
| 0.5 mm | 0.00 | 0.53 | 295 | 40 | 176 | 36.24 | High | 18.75 | 16.38 |

| Screen Size (mm) | No. 12 1.70 mm | No. 16 1.18 mm | No. 20 0.85 mm | No. 25 0.71 mm | No. 30 0.60 mm | No. 35 0.50 mm | Pan <0.50 mm | Sieve Size Pore Size (mm) |
|---|---|---|---|---|---|---|---|---|
| BEI Grind | 0.02 | 0.26 | 2.53 | 7.91 | 12.14 | 20.80 | 54.96 | |
| 0.5 mm | 0.00 | 0.00 | 0.00 | 0.00 | 0.00 | 0.00 | 100.00 | Percentage on Pan |

| Process | AA | GA |
|---|---|---|
| Conventional | Liquozyme SC | GC 480 |
| Raw Starch | SP 288 | Spirizyme Plus |

Example 3

Impact of Grind Particle Size, Glucoamylase Type, and Acid Fungal Amylase Dosage on Fermentation Efficiency Results of an embodiment of the method of the present invention were evaluated with varying particle size of the ground plant material, varying glucoamylase type, and dosage of acid fungal amylase.

Materials and Methods

Whole Corn and corn flour was obtained from Dakota Ethanol LLC in Wentworth, S.D. The whole corn was ground through a 2.0 mm screen as in prior examples using a lab scale hammer mill. Fermentations were set up in a similar manner as prior Examples according to the outline in Table 5.

Results and Discussion

Figure 4A:
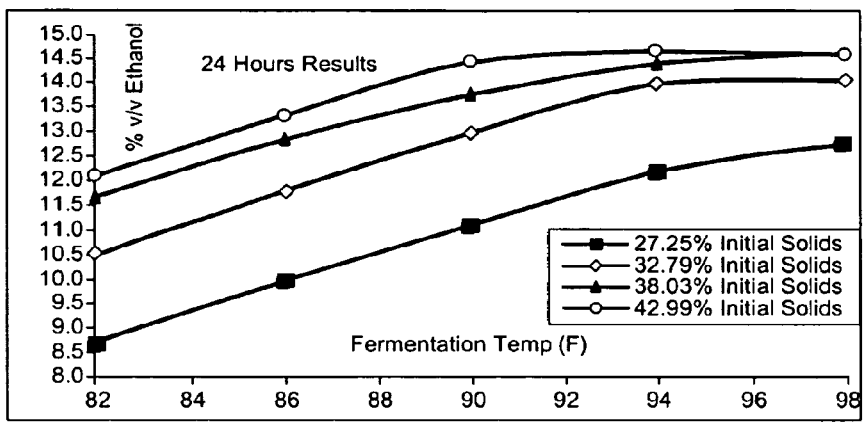
FIGS. 4A-4J schematically illustrate the effect of initial dry solids and temperature on fermentation performance in the present process.
Figure 4B:
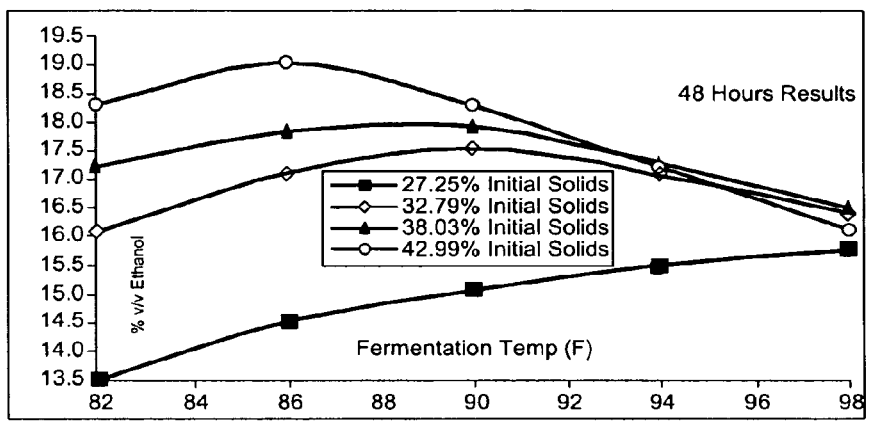
Figure 4C:
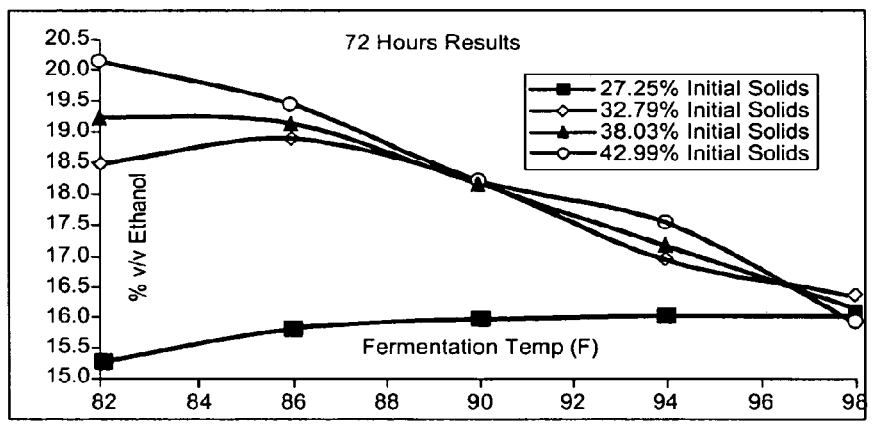
Figure 4D:
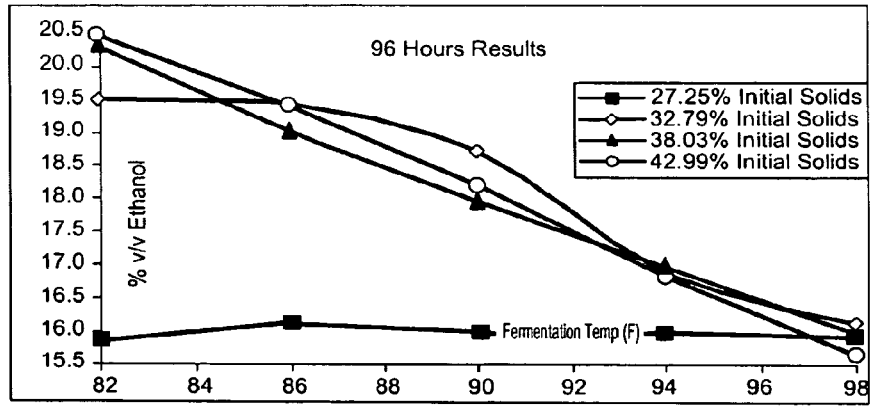
Figure 4E:
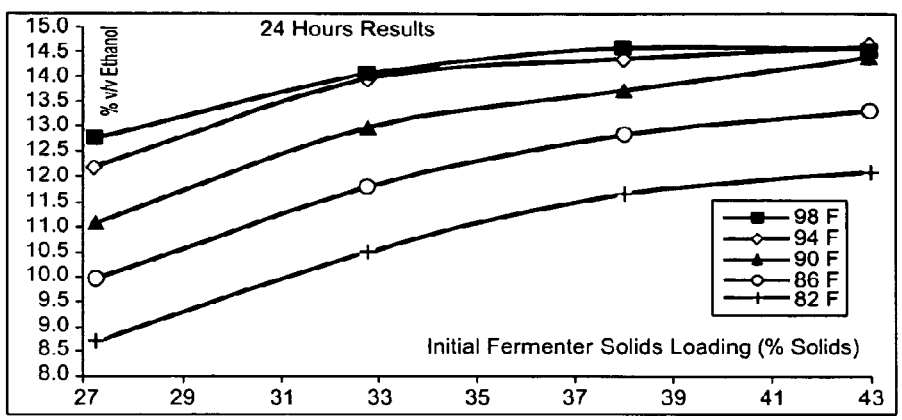
Figure 4F:
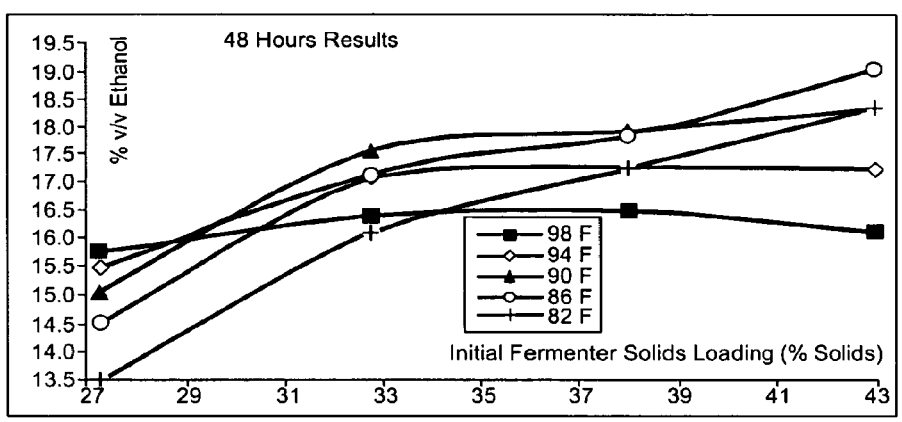
Figure 4G:
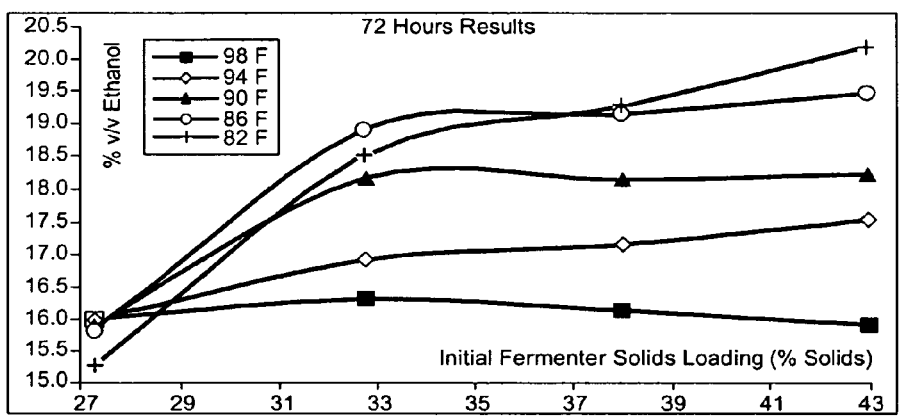
Figure 4H:
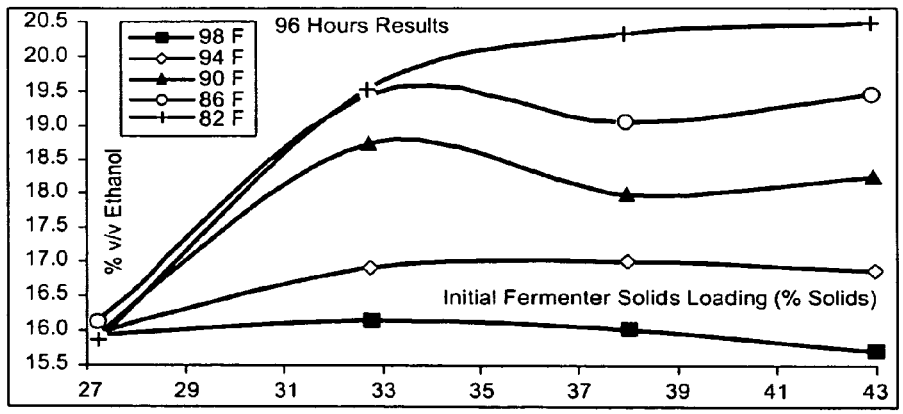
Figure 4I:
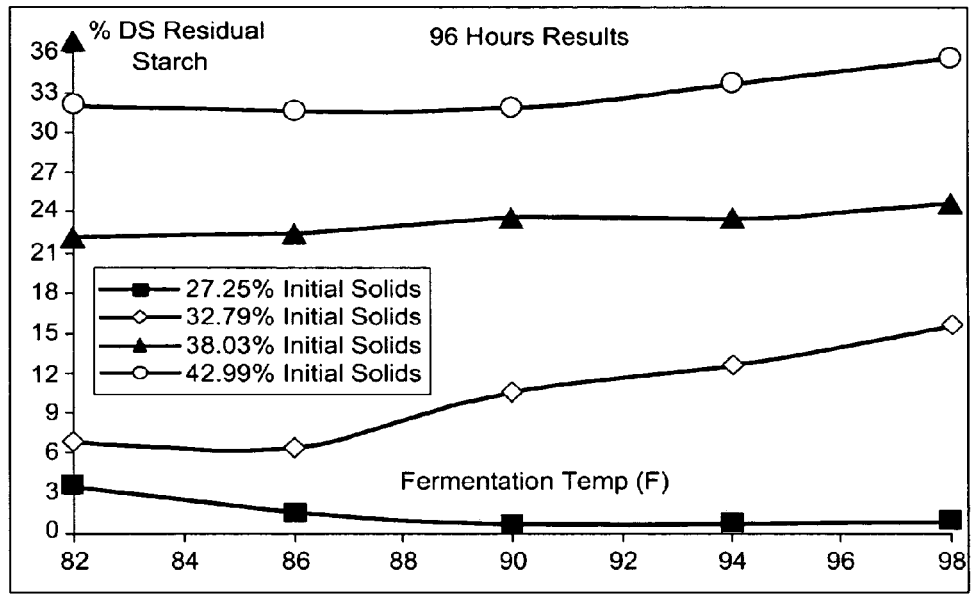
Figure 4J:
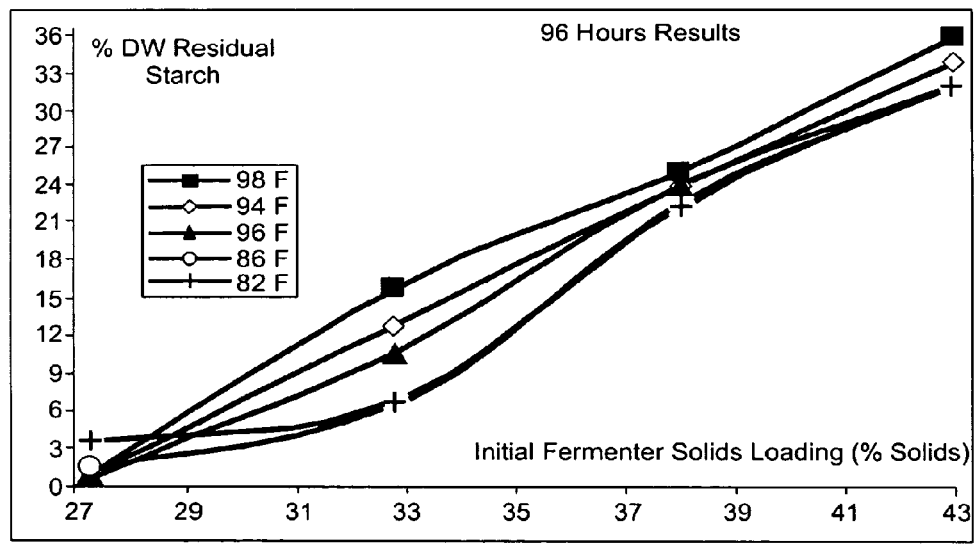
Figure 5A:
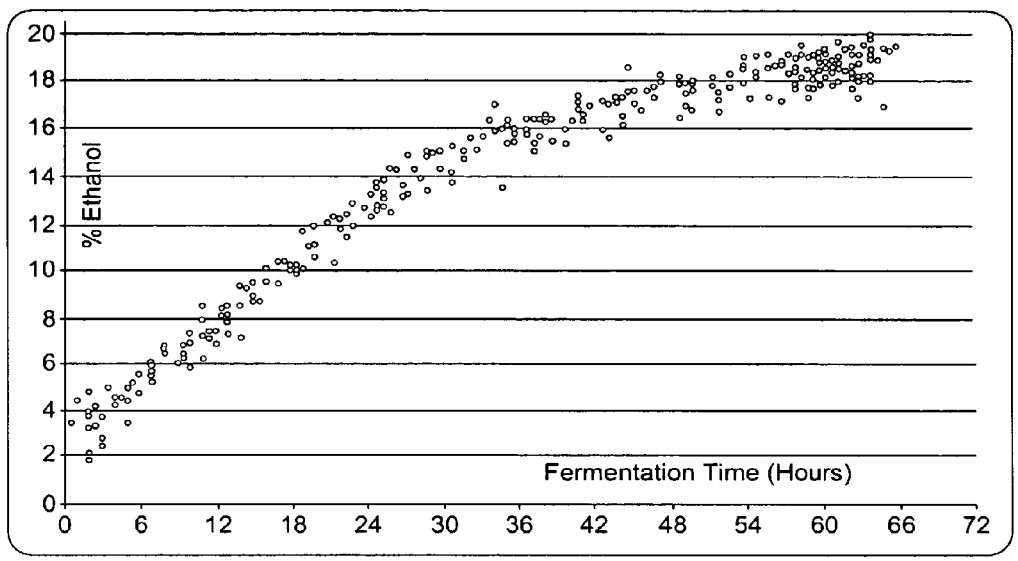
FIGS. 5A and 5B schematically illustrate high levels of ethanol production from the process of the present invention using simultaneous saccharification and fermentation (SSF) batch or continuous modes of operation.
Figure 5B:
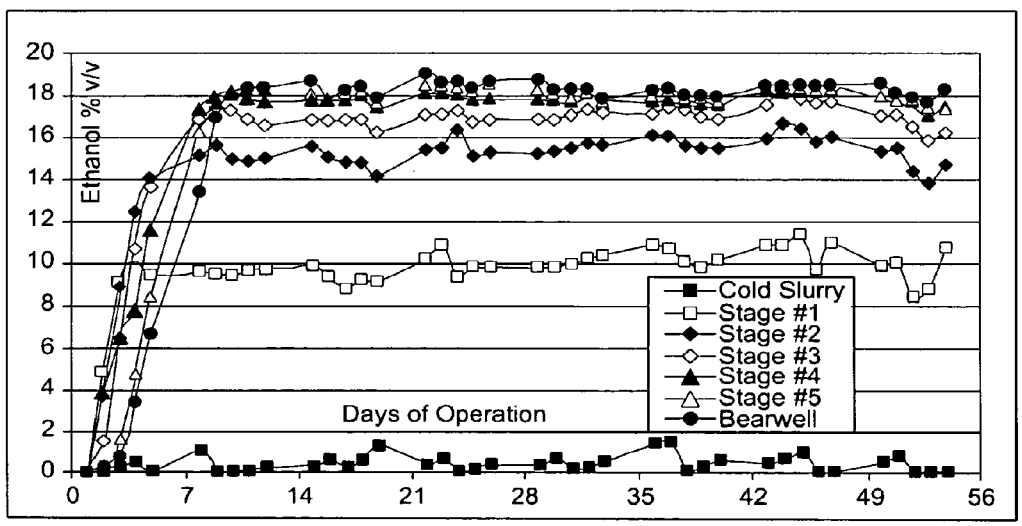

Final fermenter results are shown in FIGS. 4A, 4B, and 4C. Conventional glucoamylase enzymes such as Distillase from Genencor International contained a very low level of acid fungal amylase activity. Spirizyme Plus contained about 2.5 times as much AFAU activity per ml of enzyme and exhibited improved performance for hydrolyzing raw starch. SP 288 acid fungal amylase contained a relatively low level of glucoamylase.

It was possible to gain an understanding of the importance of grind size, glucoamylase dosage level, and acid fungal amylase dosage level on fermentation performance. Improved results were obtained when a "finer" grind was combined with glucoamylase containing enhanced acid fungal amylase levels. With a courser grind, high dosage levels of glucoamylase including acid fungal amylase yielded improved fermentation performance. Glucoamylase including acid fungal amylase provided benefits as grind size decreased.

TABLE 5

Impact of Grind Particle Size, Glucoamylase Type, and Acid Fungal Amylase Dosage on Fermentation Efficiency

| Screen Size (mm) | No. 12 1.70 | No. 16 1.18 | No. 20 0.85 | No. 25 0.71 | No. 30 0.60 | No. 35 0.50 | Pan <0.50 | Sieve Size Pore Size (mm) |
|---|---|---|---|---|---|---|---|---|
| 2.0 mm Plant Hammer mill #7 | 0.0 10.2 | 0.2 18.9 | 1.4 14.0 | 3.2 7.4 | 3.6 3.8 | 15.3 7.9 | 73.0 38.1 | "Finer Grind" "Coarser Grind" |

Experimental Outline for Example 5

| AFAU Dose Per Gram DSC ||| AGU Activity per gram DSC ||| | | |
|---|---|---|---|---|---|---|---|---|
| From SP 288 SP 288 Units/ gm DSC | From GA GA Units/ gm DSC | Total AFAU Total AFAU Units/gm DSC | From SP 288 SP 288 Units/ gm DSC | From GA GA Units/ gm DSC | Total AGU's Total AGU's Units/gm DSC | Flour Grind | L-400 GA Applied | Fermenter # |
| 0 | 0.20 | 0.20 | 0.00 | 1.10 | 1.10 | Finer | Spirizyme+ | 1 |
| 0.20 | 0.20 | 0.39 | 0.02 | 1.10 | 1.12 | Finer | Spirizyme+ | 2 |
| 0.59 | 0.20 | 0.78 | 0.05 | 1.10 | 1.15 | Finer | Spirizyme+ | 3 |
| 0.00 | 0.20 | 0.20 | 0.00 | 1.10 | 1.10 | Coarser | Spirizyme+ | 4 |
| 0.20 | 0.20 | 0.39 | 0.02 | 1.10 | 1.12 | Coarser | Spirizyme+ | 5 |
| 0.59 | 0.20 | 0.78 | 0.05 | 1.10 | 1.15 | Coarser | Spirizyme+ | 6 |
| 0.00 | 0.08 | 0.20 | 0.00 | 1.10 | 1.10 | Finer | Distillase | 7 |
| 0.20 | 0.08 | 0.39 | 0.02 | 1.10 | 1.12 | Finer | Distillase | 8 |
| 0.59 | 0.08 | 0.78 | 0.05 | 1.10 | 1.15 | Finer | Distillase | 9 |
| 0.00 | 0.08 | 0.20 | 0.00 | 1.10 | 1.10 | Coarser | Distillase | 10 |
| 0.20 | 0.08 | 0.39 | 0.02 | 1.10 | 1.12 | Coarser | Distillase | 11 |
| 0.59 | 0.08 | 0.78 | 0.05 | 1.10 | 1.15 | Coarser | Distillase | 12 |

| | | 72 Hour Results ||||||||||
|---|---|---|---|---|---|---|---|---|---|---|---|
| Fermenter # | % Ethanol | Residual Carbohydrates Wt. % |||| Byproducts Wt. % ||| Total % Solids | Residual Starch % dw |
| | | DP4+ | DP3 | Malt | Gluc | Fruc | Glyc | Lactic | Acetic | | |
| 1 | 17.84 | 0.36 | 0.01 | 0.01 | 0.01 | 0.12 | 0.89 | 0.07 | ND | 15.31 | 17.09 |
| 2 | 18.17 | 0.36 | 0.01 | 0.01 | 0.01 | 0.12 | 0.89 | 0.06 | ND | 15.12 | 16.53 |
| 3 | 18.57 | 0.36 | 0.01 | 0.01 | 0.02 | 0.12 | 0.90 | 0.06 | ND | 14.72 | 16.31 |
| 4 | 19.46 | 0.45 | 0.02 | 0.03 | 0.28 | 0.16 | 0.92 | 0.04 | ND | 14.36 | 15.14 |
| 5 | 19.65 | 0.44 | 0.02 | 0.04 | 0.57 | 0.17 | 0.92 | 0.04 | ND | 14.49 | 14.97 |
| 6 | 19.74 | 0.42 | 0.01 | 0.04 | 0.59 | 0.19 | 0.90 | 0.04 | ND | 14.40 | 13.81 |
| 7 | 14.42 | 0.37 | 0.01 | 0.01 | ND | 0.05 | 0.65 | 0.16 | ND | 20.24 | 36.27 |
| 8 | 15.89 | 0.37 | 0.01 | 0.01 | ND | 0.10 | 0.77 | 0.07 | ND | 16.68 | 27.24 |
| 9 | 17.25 | 0.37 | ND | 0.01 | 0.01 | 0.11 | 0.86 | 0.06 | ND | 15.97 | 20.43 |
| 10 | 17.19 | 0.46 | 0.01 | 0.01 | 0.01 | 0.10 | 0.80 | 0.05 | ND | 18.19 | 31.43 |
| 11 | 18.35 | 0.44 | 0.01 | 0.01 | 0.03 | 0.14 | 0.87 | 0.05 | ND | 16.16 | 24.07 |
| 12 | 19.30 | 0.42 | 0.01 | 0.01 | 0.06 | 0.15 | 0.92 | 0.05 | ND | 14.95 | 18.01 |

Example 4

Impact of Fermenter Dry Solids Loading and Temperature on Fermenter Kinetics and Ethanol Performance An embodiment of the present invention was employed to produce ethanol from corn. This process produced high alcohol corn beer, high protein, high fat, and high fiber distiller's dried grain. Comparison with conventional saccharification and liquefaction process indicate superior performance of the present method.

Materials and Methods

Example 6 was set up in a manner similar to prior examples except the initial fermentation solids and temperature were varied as described in the presentation of the results.

Results

An interesting feature of the present raw starch fermentation process is the ability to enhance the rate of fermentation through increasing the solids content or initial temperature of fermentation. Solids loading, temperature, grind size, glucoamylase dosage, acid fungal amylase dosage, and yeast dosage can be combined to increase the performance of raw starch fermentation. FIGS. 5A, 5B, 5C, 5D, 5E, 5F, 5G, 5H, 5I, and 5J illustrate the influence of temperature at different solids loadings.

The residual starch values reported for this Example suggest that temperature can be used to improve the efficiency of raw starch fermentations at intermediate fermentation gravities, which are defined as fermentation solids levels which would yield between 15% to 18% ethanol. The fermentation temperature could be used to accelerate raw starch fermentations so that they finish in less than 48 hours, yet still achieve alcohol levels of 15% to 18%, with acceptable residual starch levels. The increased fermentation set point will help to accelerate enzymatic conversion of native starch to glucose, which appears to be the rate limiting step in the raw starch process. Fermentation performance using higher temperature set points is an aspect of the process for intermediate ethanol ranges, especially when viewed from the perspective of prior examples establishing that raw starch fermentations can tolerate a higher level of residual starch in the residual distillers dried grains and with distillers dried grains solubles, and still produce excellent quality DDG or DDGS according to the proximate analysis. Alternatively, the dry substance of raw starch fermentations can be increased by approximately 20% to increase the rate of fermentation, while producing higher alcohol content in the fermenter and more DDGS with excellent quality even if the residual starch levels are high. By balancing the above inputs, a yield versus throughput economic optimization can be done with a significant decrease in difficulty. The ease of operating a high gravity, high throughput process while producing a saleable DDGS is significantly enhanced by the raw starch process.

Example 5

Advantageous Aspects of Ethanol Production by the Present Process

A variety of fermentation runs were conducted and the results were evaluated and compiled to demonstrate the increased alcohol production and production of distiller's dried grain by the present process.

Ethanol Production

Figure 6:
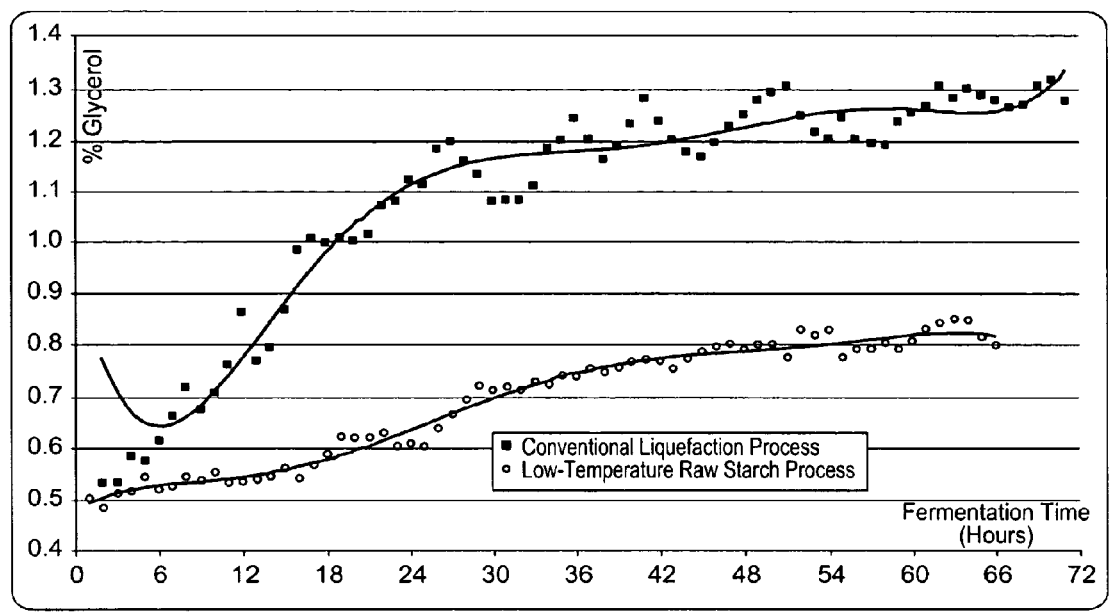
FIG. 6 schematically illustrates that the present process maintained low levels of glycerol during SSF batch operations.

The present method produced ethanol containing corn beer with greater than 18 vol-% ethanol. Runs produced at least 18 vol-% ethanol and up to 23 vol-% ethanol within 48 to 96 hours of incubation and fermentation. The beer contained these high levels of ethanol even when it also included higher levels of residual starch. After 24 hours of incubating and fermenting the corn beer contained 9-16.5 or 12-15 vol-% ethanol. After 48 hours of incubating and fermenting the corn beer contained 13-20 vol-% ethanol. Ethanol production was linear up to a level of 14-16 vol-%. A compilation of ethanol production results from various runs is illustrated at least in FIGS. 6A and 6B.

Figure 7:
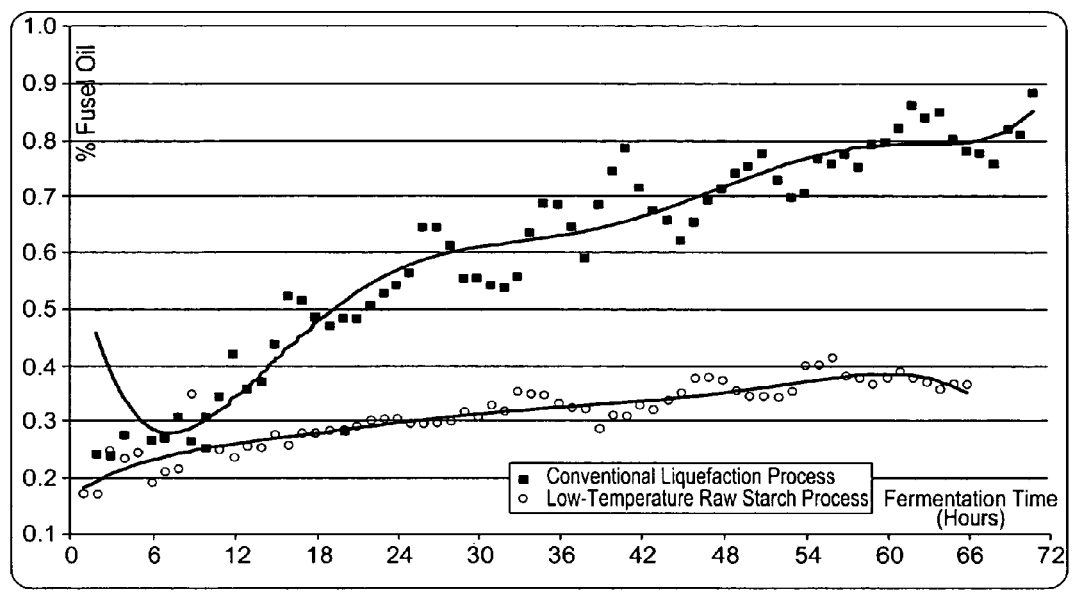
FIG. 7 schematically illustrates that the present process maintained low levels of fusel oils during SSF batch operations.
Figure 8:
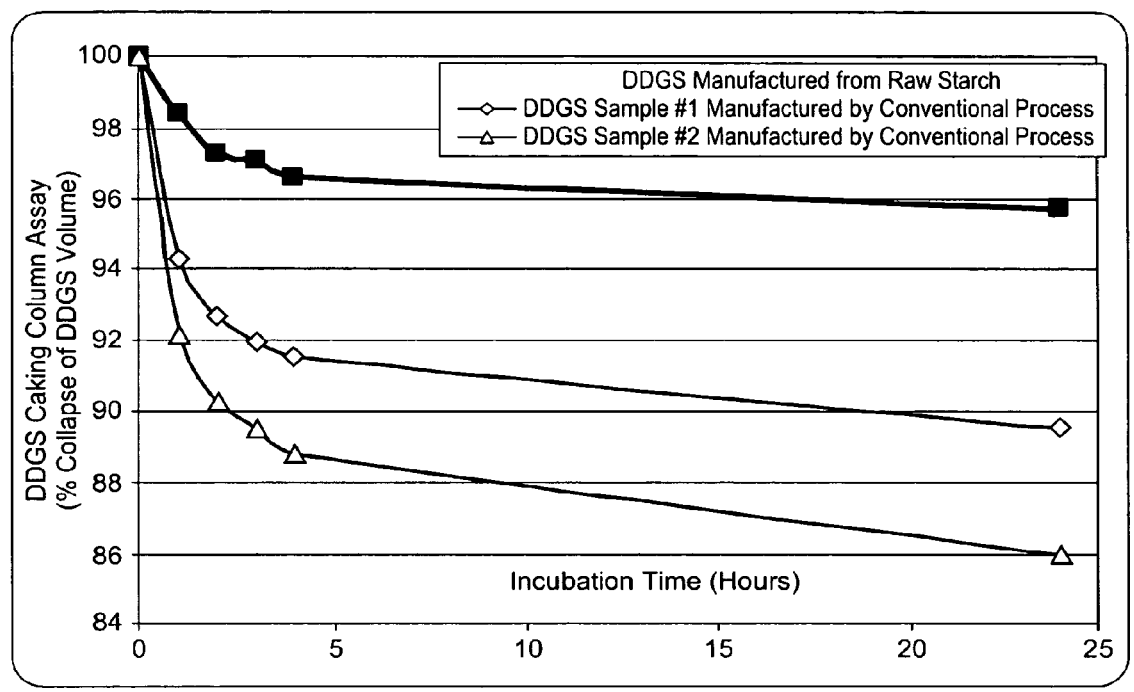
FIG. 8 schematically illustrates that the present process impacts DDGS quality favorably based on caking tendency.
Figure 9A:
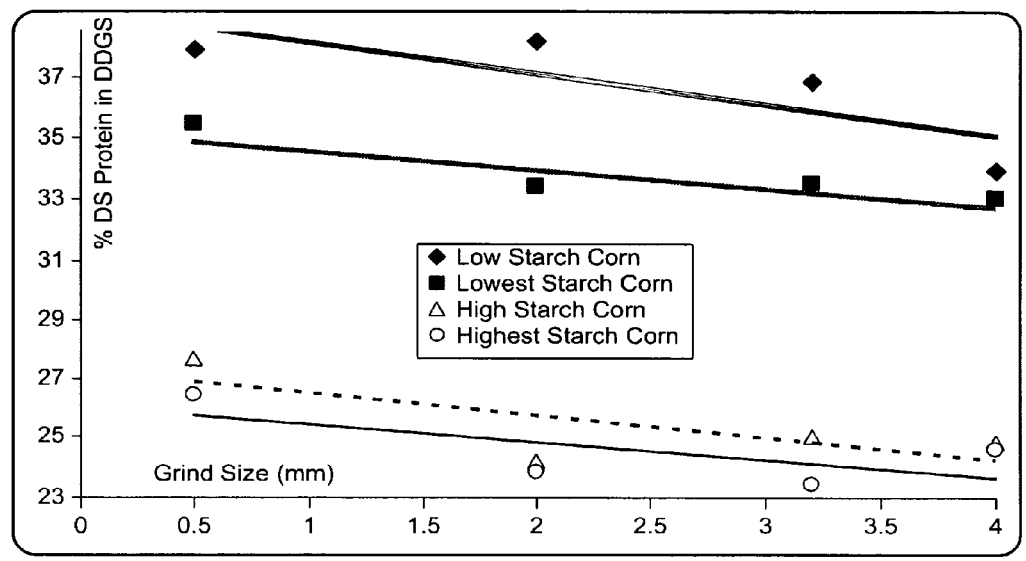
FIGS. 9A-9D schematically illustrate that the present process affords advantageous fermentation of non traditional feedstocks.
Figure 9B:
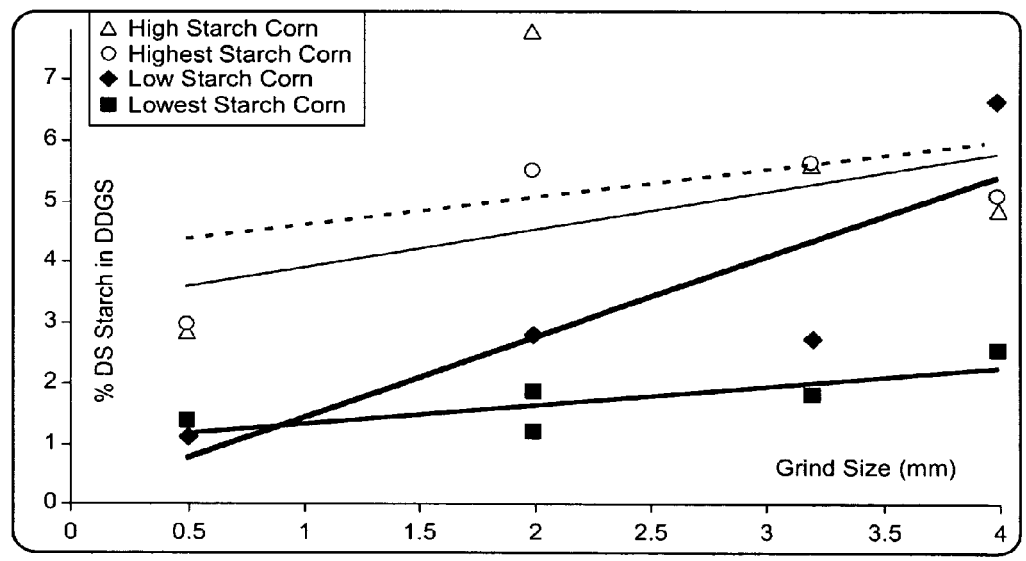
Figure 9C:
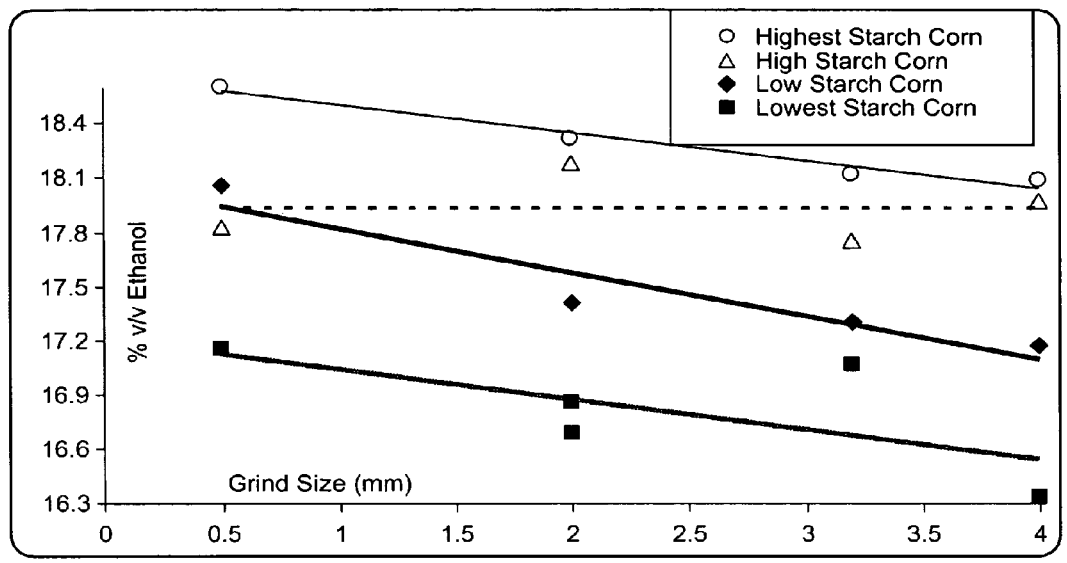
Figure 9D:
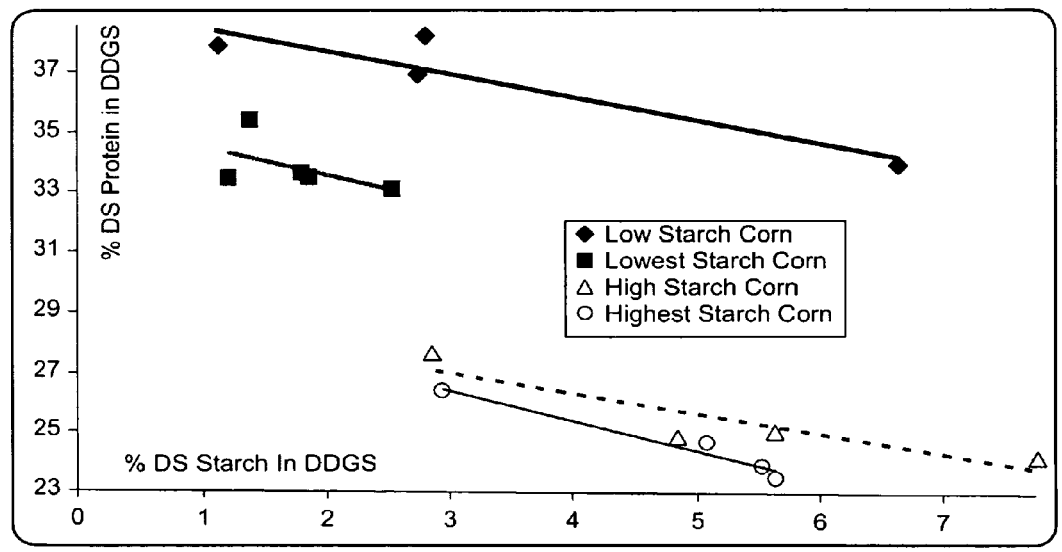
Figure 10A:
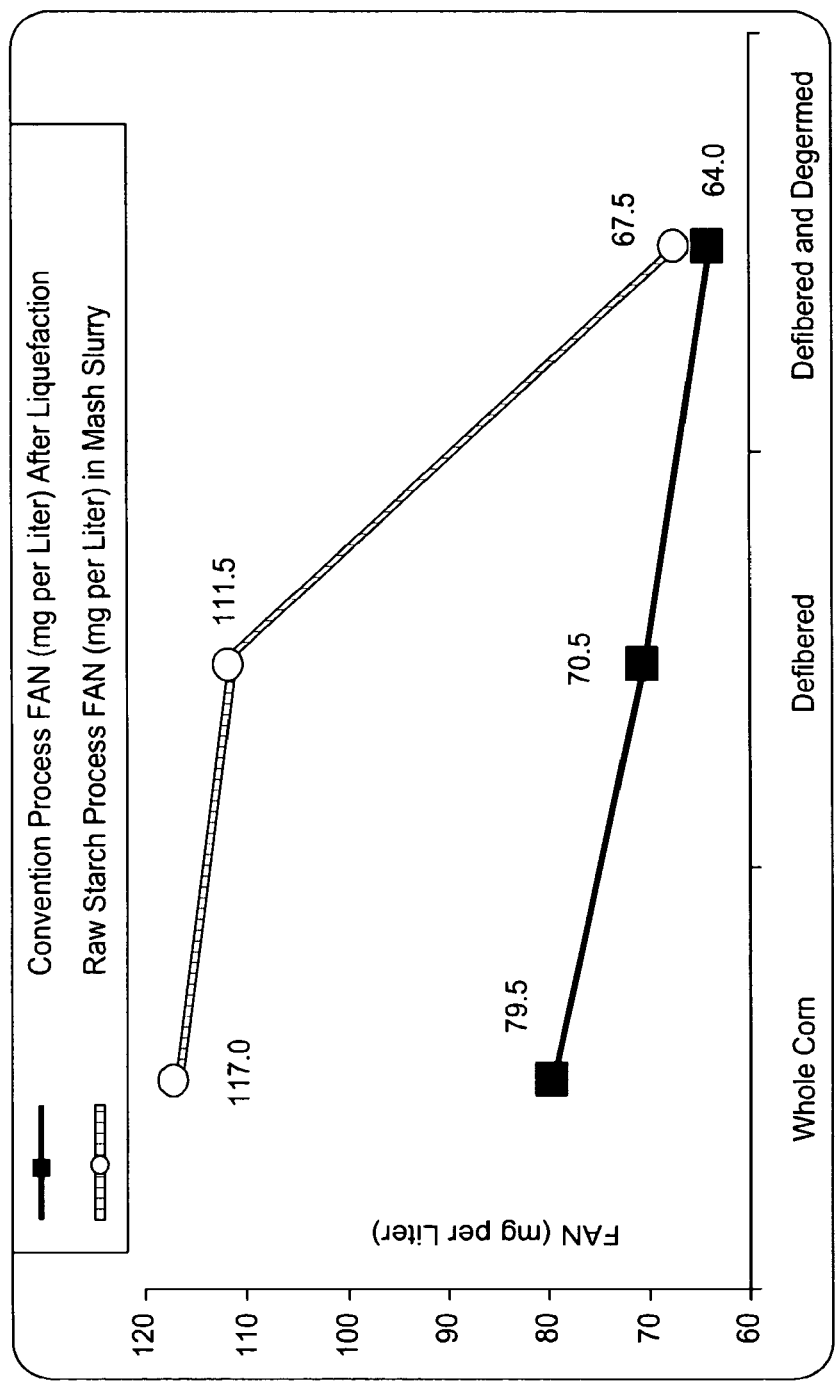
FIGS. 10A-10C schematically illustrate that the present process provides improved efficiency for fermentation of corn fractions produced by dry milling fractionation processes.
Figure 10B:
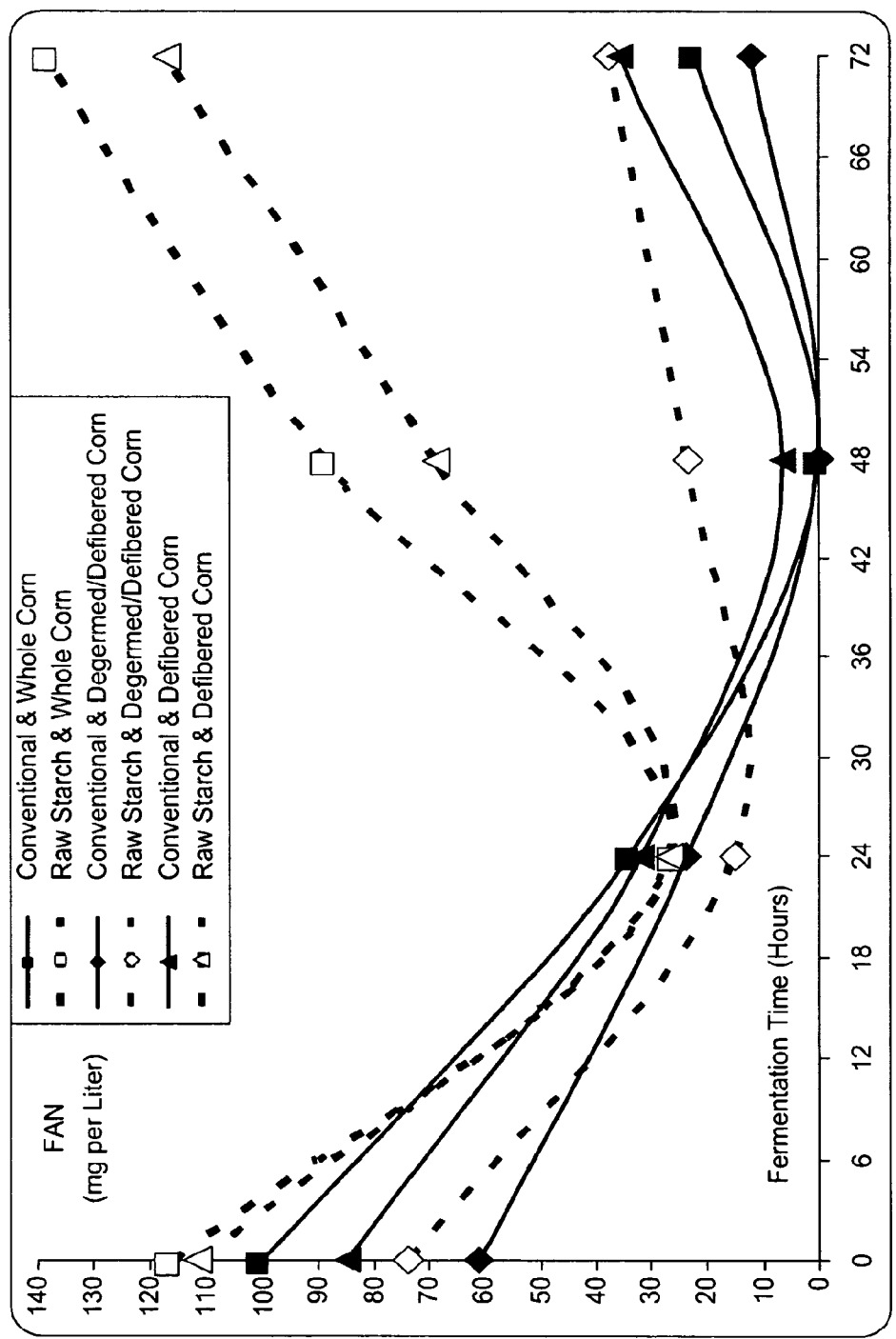
Figure 10C:
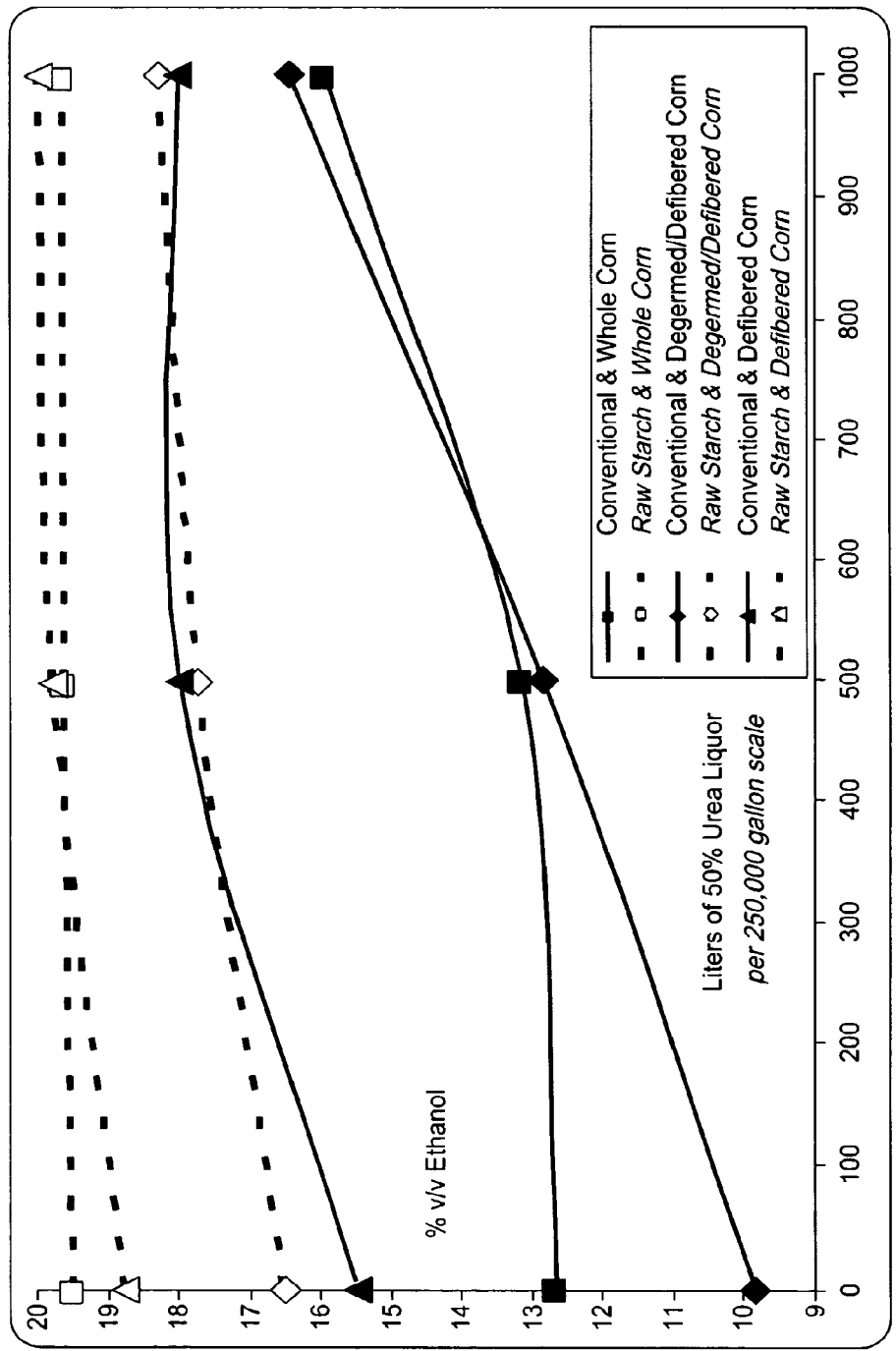
Figure 11A:
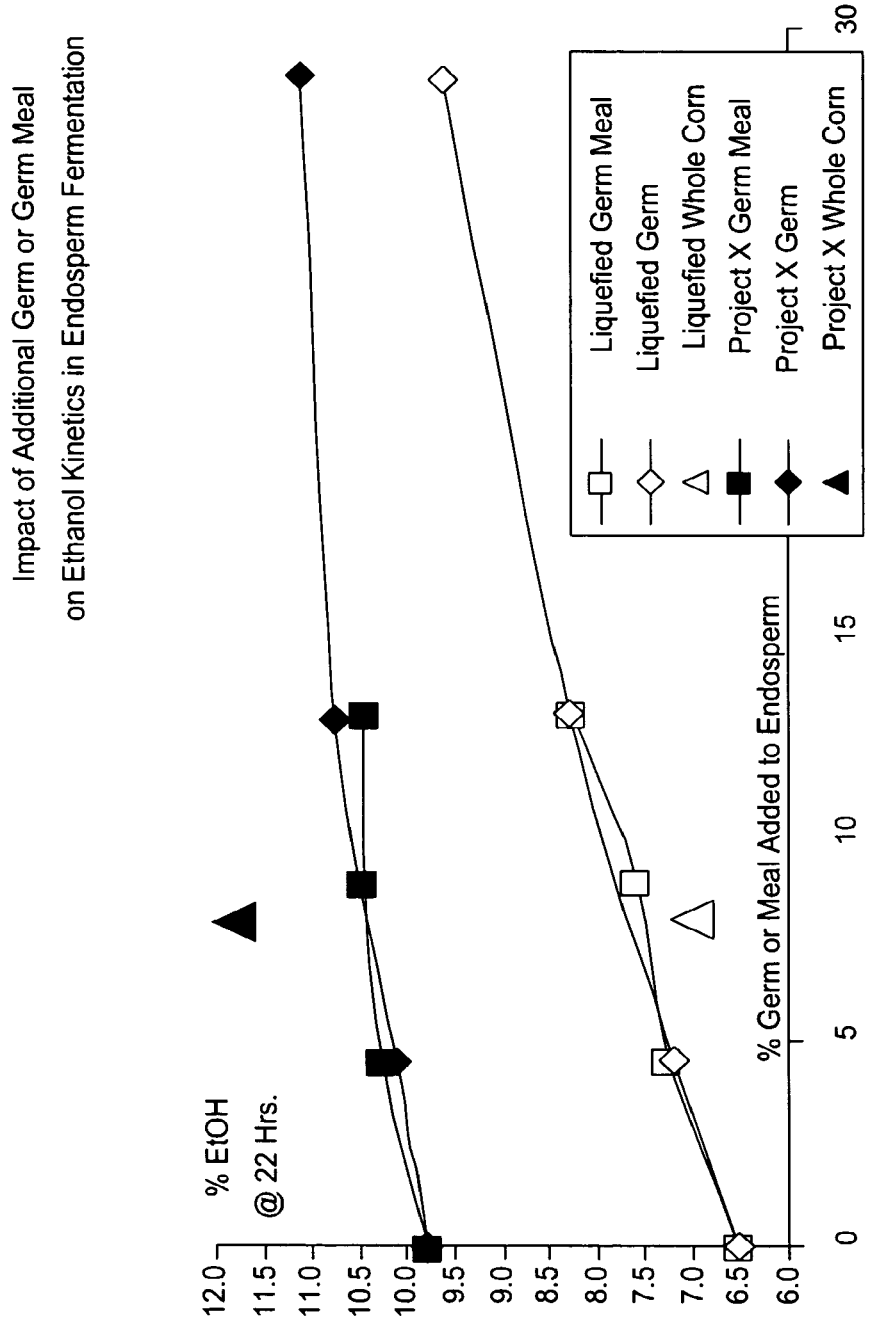
FIGS. 11A-11C schematically illustrate that the present process provides improved efficiency for fermentation of corn fractions produced by dry milling fractionation processes.
Figure 11B:
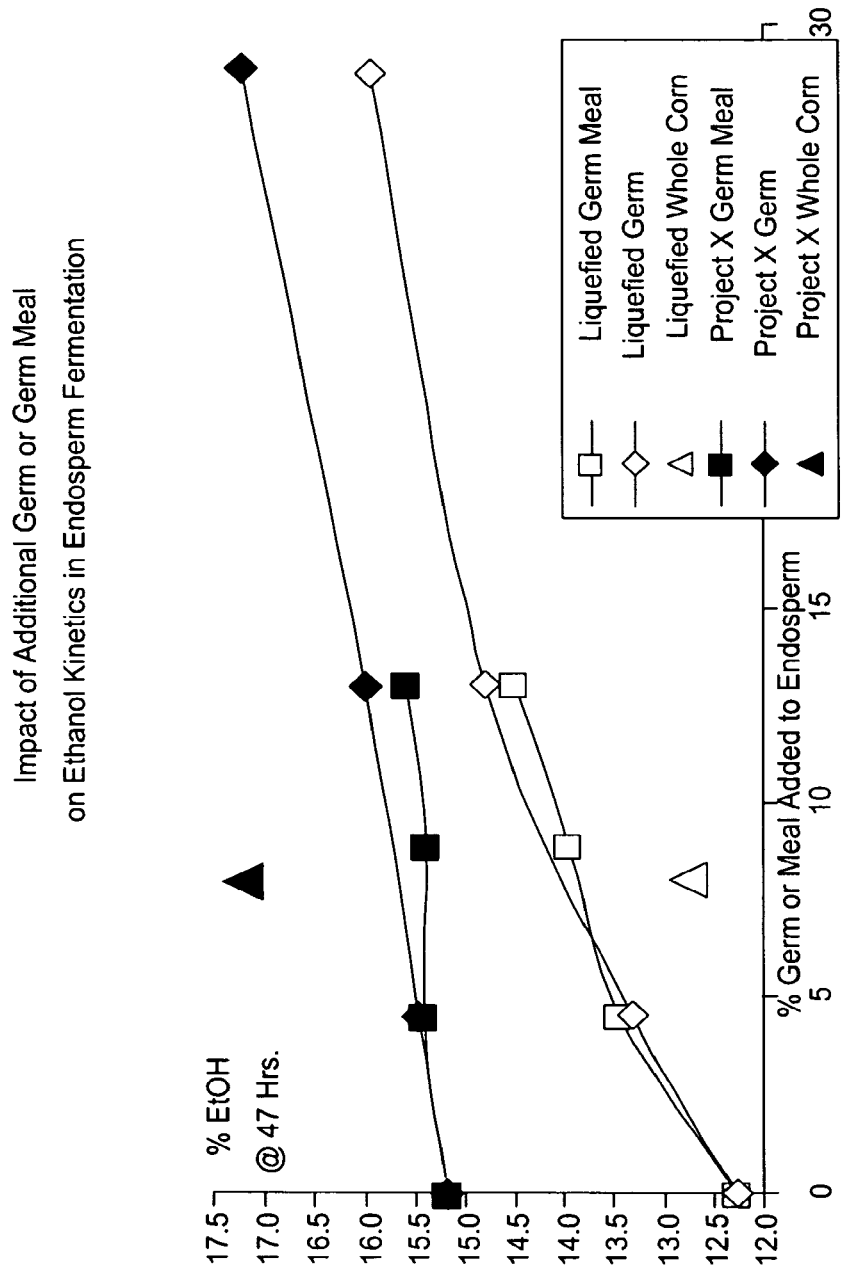
Figure 11C:
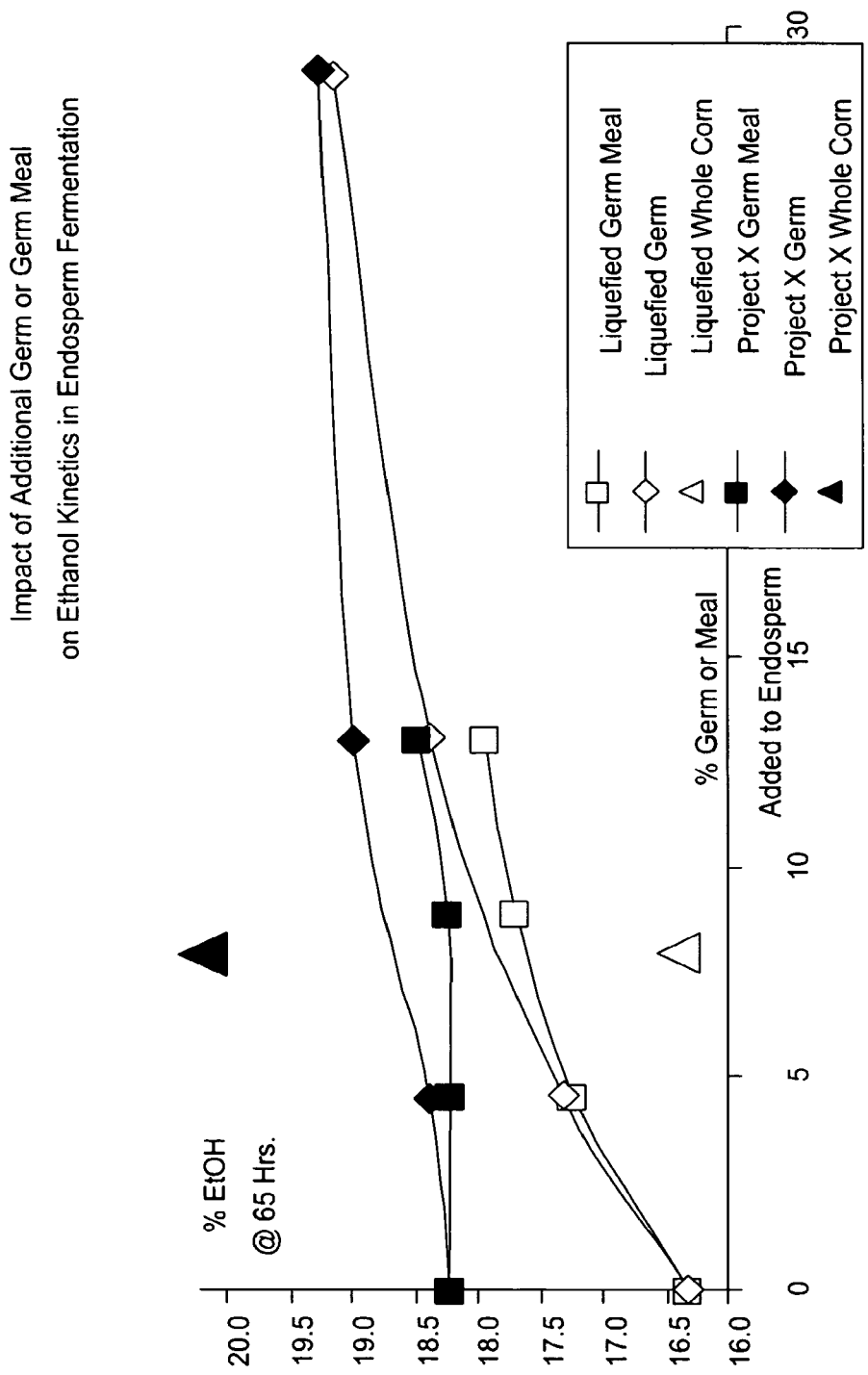

The beer contained approximately 0.4 to 0.5 wt-% less glycerol than conventional fermentation at otherwise identical fermentation conditions (FIG. 7). The beer contained less extracted oil from the germ fraction, resulting in reduced fouling and lower VOC emissions in the water vapor during drying of the residual animal feed product. (Table 1) The beer contained less extracted oil from the germ fraction, resulting in reduced fouling and lower CO emissions in the water vapor during drying of the residual animal feed product (Table 1). The beer contained less fusel oil (FIG. 8), which inhibits yeast cell growth and fermentation if these alcohol compounds are unintentionally recycled in distillation side stripper bottoms streams. Fusel oils are also an undesirable component of potable alcohol manufacturing operations, so the present process offers an improved method of production of potable alcohol. The beer also contained less lactic and acetic acid relative to the conventional process. The beer also contained higher yeast cell counts, which contributes to improved feed products.

In addition, the present process maintained yeast at or above 300 cells/mL in these numerous runs. Yeast budding was observed in at least 40% of the yeast from hours 0-20 of incubating and fermenting and/or at least 15-20% of the yeast after hours 60 of incubating and fermenting. These yeast counts and budding are higher than observed in the conventional process.

Example 6

The Present Process Produces DDGS with Less Caking and Compacting

The DDGS according to an embodiment of the present invention was compared to that produced by a conventional process. The present method produced an inventive DDGS that exhibited less caking compared to DDGS produced by the conventional process. The present DDGS with less caking is superior to conventional DDGS.

Materials and Methods

The DDGS was collected as a co-product of ethanol production from the conventional high temperature liquefaction process and from the process of the present invention. The caking/collapse assay was performed by filling a 500 ml cylinder with approximately 400 ml of DDGS. Attention was given to avoiding physical packing of the DDGS when filling the cylinder. After filling, a 4.4 cm diameter disc weighing 78 grams was placed on top of the DDGS, followed by placement of 1.5 kg of lead shot (in an appropriately sized plastic bag) on top of the disc. Assay preparation was completed by covering each cylinder with a plastic bag and sealing the apparatus with a rubber band to prevent moisture loss. The weight applied to the DDGS is used to exaggerate the effect and approximate the conditions which DDGS is exposed to during transport, for example, in a railcar. The level of the DDGS is noted at the beginning of storage and at various times during storage at a temperature of 50° C. The measured height of the collapsed (caked) DDGS was compared to the initial height of the DDGS. The measured height was compared to the initial height as an estimate of the tendency of the product to collapse or cake.
Results The DDGS from the present invention shows less caking collapse over time (FIG. 13) when compared to the DDGS of the conventional process. Over a twenty-five hour compaction time the DDGS according to the present invention collapsed only 4-5% of the initial volume as compared to 10-14% of the volume collapse for DDGS of the conventional process.
Discussion The compaction of DDGS at controlled conditions models the DDGS caking observed in the containers of transportation vehicles, for example railcars and trucks. DDGS produced using the process of this invention exhibited less caking related collapse than that of the conventional process, indicating superior performance of the present method.

Although not limiting to the present invention, it is believed that the observed compaction is consistent with that suggested by glass transition theory. For example, glass transition temperature increases with molecular weight for polymers such as those found in DDGS. The present DDG includes higher levels of such polymers and should exhibit a higher glass transition temperature. It is believed that product moisture, storage temperature, and chemical composition can impact the transition of DDGS from an amorphous glass to an amorphous rubber phase. DDGS in the rubber phase compacts more readily that DDGS in the glass phase.

Example 7

The Present Process can Employ High Protein Corn to Produce High Protein DDGS and High Levels of Ethanol In an embodiment, the present invention can include fermenting high protein corn to produce high protein DDGS and high levels of ethanol. This provides for advantageous flexibility for processing high protein corn.
Materials and Methods DDGS was collected as a co-product of ethanol production from fermentation of various corn hybrids with fermentations set up in a similar manner as Example 1. All fermentations were set up using identical conditions. Different corn hybrids were tested using various grind sizes using a lab scale hammer mill. The hammer mill screen size was varied from 0.5 mm to 4.0 mm to create flour particle sizes ranging from fine (0.5 mm screen) to coarse (4.0 mm screen).
Results FIG. 15A illustrates the dependence of protein level in DDGS on grind size. This figure illustrates the inverse correlation between grind size and protein: as particle size increases the protein content of DDGS decreases for each tested corn hybrid (FIG. 15A). FIG. 15B illustrates the dependence of starch level in DDGS on grind size. This figure illustrates a positive correlation between grind size and starch content in: as particle size increases the starch content of the DDGS increases for each tested corn hybrid (FIG. 15B). FIG. 15C illustrates the dependence of ethanol production on grind size. This figure illustrates that as particle size decreases there is an increase in ethanol production (FIG. 15C).
Discussion Reduced particle size arising from grinding of the corn enables higher ethanol yields and higher protein DDGS to be created. A strong correlation is also seen between the initial protein content of the corn and the resulting protein content of the DDGS. In the conventional process, higher protein corn is undesirable because it lowers fermentable starch content. The conventional process, being more constrained by viscosity arising from liquefaction, limits the processor's ability to maintain fermentables by increasing the solids level in fermentation. The present method is less constrained by viscosity, such that fermentable solids can be increased to maintain potential ethanol production titers while simultaneously producing a higher protein DDGS. The higher protein DDGS can be used for any of a variety of purposes.

It should be noted that there is significant effort within the current industry to encourage the use of "highly fermentable corn" hybrids. The "highly fermentable corn" hybrids can have a higher starch concentration and not a high protein concentration. This example demonstrates that higher protein corn hybrid varieties of standard #2 yellow corn can be used to obtain high levels of ethanol production. Despite standard #2 yellow corn lower starch contents, fermenter dry solids can be increased to maintain ethanol % levels in the fermenter while producing a higher protein DDGS.

Example 8

The Present Process Provides Improved Efficiency with Substrates Derived From Grain Dry Milling Operations (Endosperm, Fiber, & Germ)

Figure 2A:
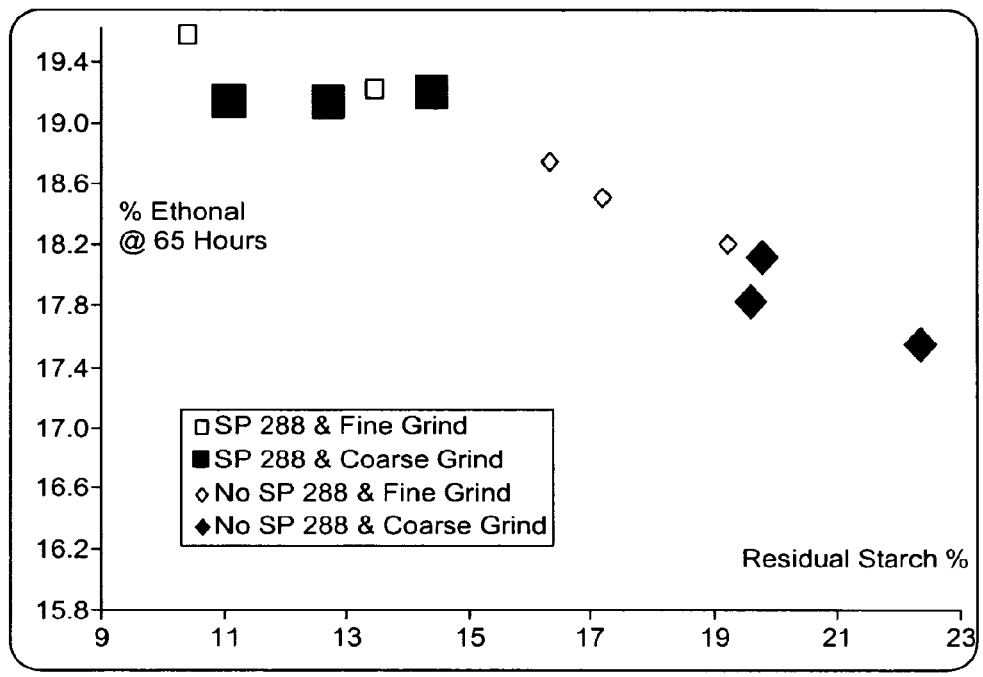
FIGS. 2A-2E schematically illustrate a comparison of the yield of the process of the present invention compared to the conventional process.
Figure 2B:
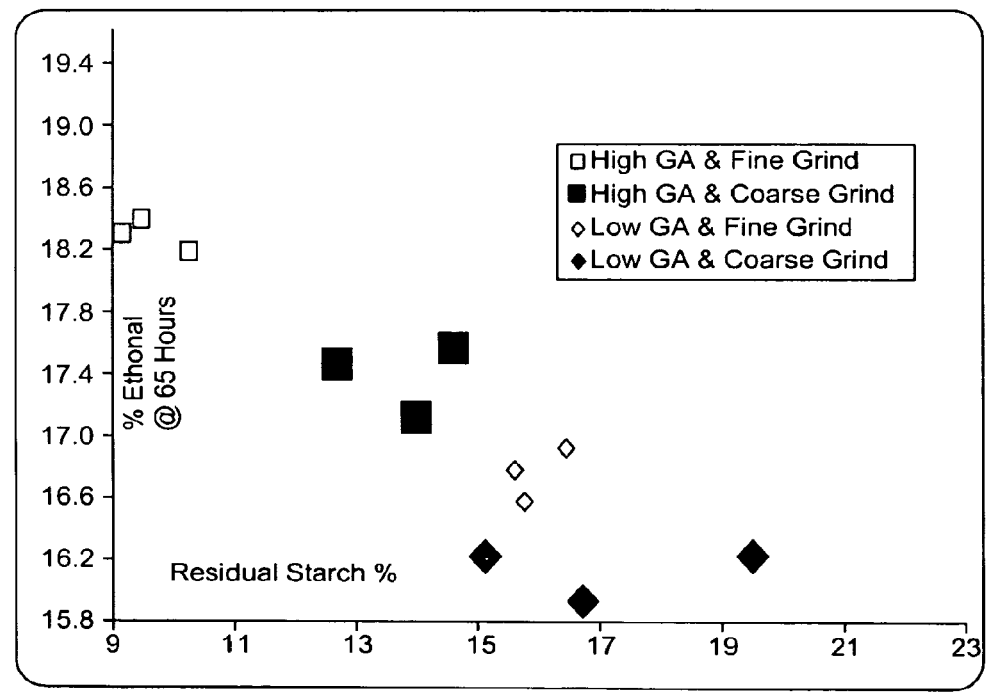

The present invention provides an improved method for fermenting substrates derived from grain milling (dry fractionation) processes. The present process is useful for endosperm fermentation since FAN levels in the mash are reduced to the removal of germ. The present process contributes to the endogenous enzymes activity in the grain. Dramatic increase in FAN in whole corn and defibered corn fermentations are reached compared to the initial mash slurry.
Results and Discussion The present process is useful for endosperm fermentation since FAN levels in the mash are reduced due to the removal of germ, as shown in FIG. 2A. FAN supplies necessary nitrogen for yeast growth and reducing ethanol related stress in high gravity ethanol fermentations. FIG. 2A also reveals the negative impact of liquefaction on reducing the amount of FAN available in fermentation. The generation of dextrins and soluble sugars during the high temperature liquefaction results in Maillard condensation reactions between carbonyl groups on sugars and amino groups on amino acids and peptides. This results in a loss in potential yield (due to unavailable carbohydrate) as well as a reduction in the nutritional quality of the mash for sustaining efficient high gravity fermentation (due to reduction in FAN). The present process also enables the endogenous enzyme activity in the grain to contribute to the generation of soluble sugars and amino nitrogen in the mash. These beneficial activities are lost during the conventional liquefaction stage. The kinetics of FAN utilization is illustrated in FIG. 2B for fermentation of various dry milled grain fractions.

It is interesting to note that FAN kinetics in the conventional process all follow a similar utilization pathway for each corn fraction. During the first half of fermentation, FAN is consumed in the course of yeast growth. Later, FAN levels are observed to increase, presumably due the liberation of cellular FAN corresponding to yeast cell death and lysis. Initial FAN utilization in the raw starch process is observed to be much more rapid. Also note the dramatic increase in FAN at the end of raw starch fermentations. This increase in FAN could be the result of yeast cell death since the rate of ethanol production is much faster in raw starch fermentations. It could also be due to generation of FAN from endogenous enzymes in the grain. Note that when germ is removed, there is less of an increase in FAN during the latter half of the fermentation. These observations suggest an additional aspect of the raw starch process.

Figure 2C:
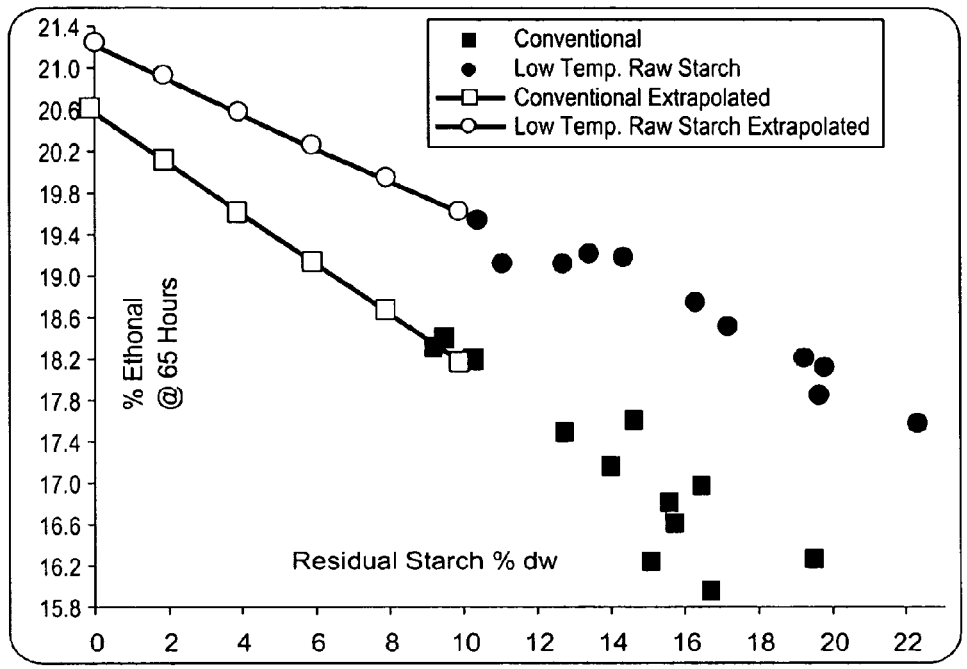
Figure 2D:
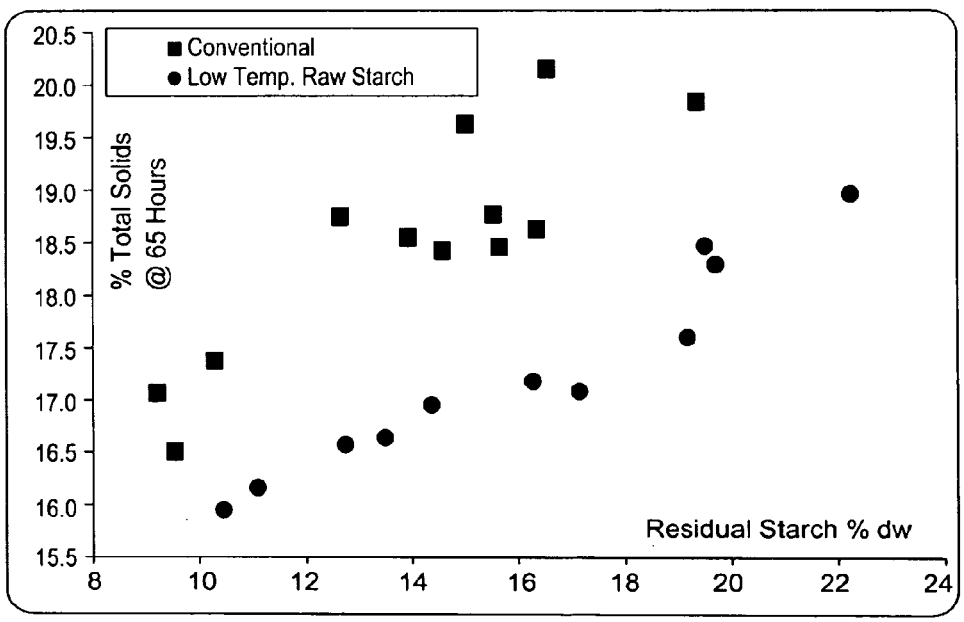
Figure 2E:
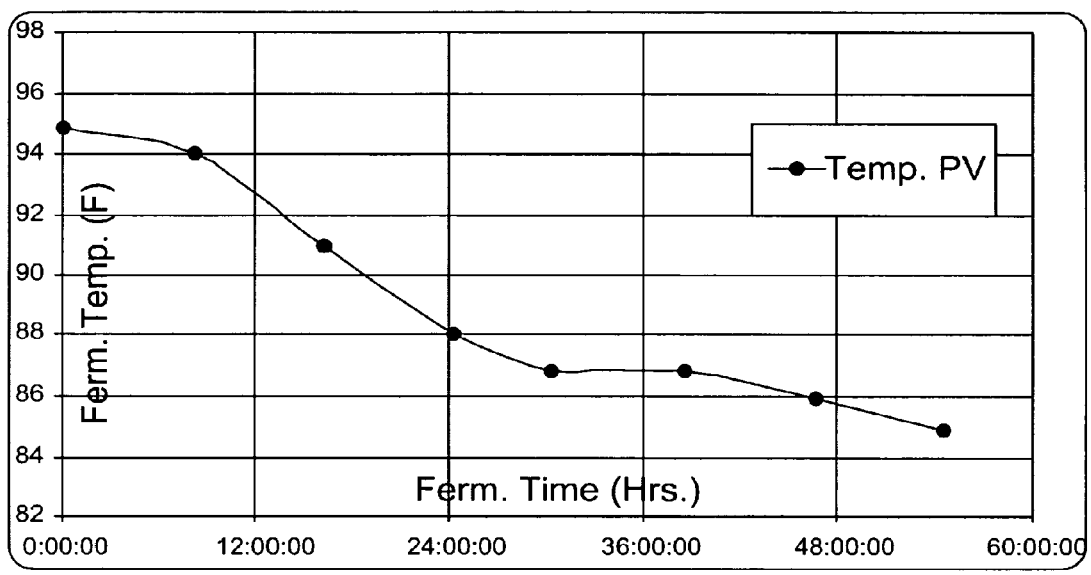

FIG. 2C illustrates the impact of FAN on corn fraction fermentations run in the absence of backset, comparing and contrasting the sensitivity of the two processes to additional FAN addition. It is apparent that the process of the present invention significantly improves the potential substrate quality from a dry milling fractionation facility for fermentation, reducing the importance of additional FAN. The present process is superior to the conventional liquefaction process, since the conventional liquefaction process is more sensitive to disruptive impact of substrate quality as measured by FAN levels.

Example 9

The Present Method Produced High Protein DDG From Fractionated Plant Product

The present invention demonstrated that fractionation of corn prior to fermentation provides high levels of protein in the resulting DDG.
Materials and Methods Corn was fractionated prior to fermentation through use of a Satake fractionation system. After fractionation, the corn was fermented according to the present invention employing for saccharification glucoamylase and acid fungal amylase without cooking. The fermentation was conducted at 90° F. and at a pH of 5. After the corn solids were fermented, the ethanol was distilled out. The remaining solids were then dried, and samples of fiber, germ, and starch were taken. All fractionation samples were ground for twenty seconds on a Knifetec. These samples were then analyzed for starch, protein, fat, and neutral detergent fiber content. The percent ethanol yield was also calculated for each sample. See also the Materials and Methods sections for the other examples for additional information about how these experiments were conducted.
Results and Discussion The present method produced high protein DDG and high levels of ethanol compared to a conventional process (Table 6). Table 6 shows results for ethanol and DDG produced from two representative samples of each of fiber, starch, and germ samples. Fermentations B and C, the representative starch samples, resulted in the highest yield of ethanol and produced DDG with the largest percentage of protein (Table 6). The two germ samples generated the lowest yield of ethanol and the highest percentage of fat (Table 6). The fiber samples produced the lowest amount of protein (Table 6). In general, this table illustrates that fractionation increased the rate of protein retention throughout the fermentation and distillation process (Table 6).

TABLE 6

Ethanol and DDG Proximate Levels Produced From Corn Fractions

| Fermentation | Ethanol vol-% | Starch % dw | Protein % dw | Fat % dw | NDR % dw | Sample Type |
|---|---|---|---|---|---|---|
| A | 8.10 | 0.00 | 22.51 | 17.93 | 30.90 | Fiber |
| B | 12.11 | 3.58 | 42.46 | 5.66 | 12.99 | Starch |
| C | 11.75 | 0.55 | 43.83 | 7.73 | 13.84 | Starch |
| D | 6.39 | 0.57 | 26.18 | 26.81 | 13.33 | Germ |
| E | 6.58 | 0.00 | 18.31 | 14.43 | 42.34 | Fiber |
| F | 4.68 | 0.34 | 22.70 | 29.49 | 17.63 | Germ |

Example 10

The Present Process Provided Improved Ethanol Kinetics in Endosperm Fermentation Via Additional Germ or Germ Meal The present invention provides an improved method for fermenting fractionated grain, such as fractionated corn derived from a grain milling (dry fractionation) process.
Materials and Methods Cook Standard Ingredients at Plant Equivalent Dose (Lab Dose) of 308 L Liquizyme SC AA (0.30 ml of a 25×) was used. Fermentation standard ingredients at plant equivalent dose (lab dose) to include 660 L Spirizyme Plus glucoamylase (0.25 ml of a 10×), 33 L protease (0.13 ml of a 100×), 4.4 lbs Lactrol (0.16 ml of a 2,000×), and no urea liquor. Fermentation temperature staging conditions included 90° F. from 0-24 hours, 84° F. from 24-48 hours, and 82° F. from 48-65 hours. Yeast propagator standard ingredients at laboratory dose to include 230 mL deionized water, 100 mL backset, 70 grams maltodextrin MO40, 0.44 mL of a 5×, 1.76 mL of a 100×, 1.07 grams, 1.07 grams, 1.70 mL of a 1000×, 0.13 grams zinc sulfate, 0.48 grams FaliYeast for an eight (8) hour propagation, propagation temperature of ninety degrees (90° F.), with a 2.88 mL transfer of yeast propagator to each fermenter for inoculation.

Figure 3A:
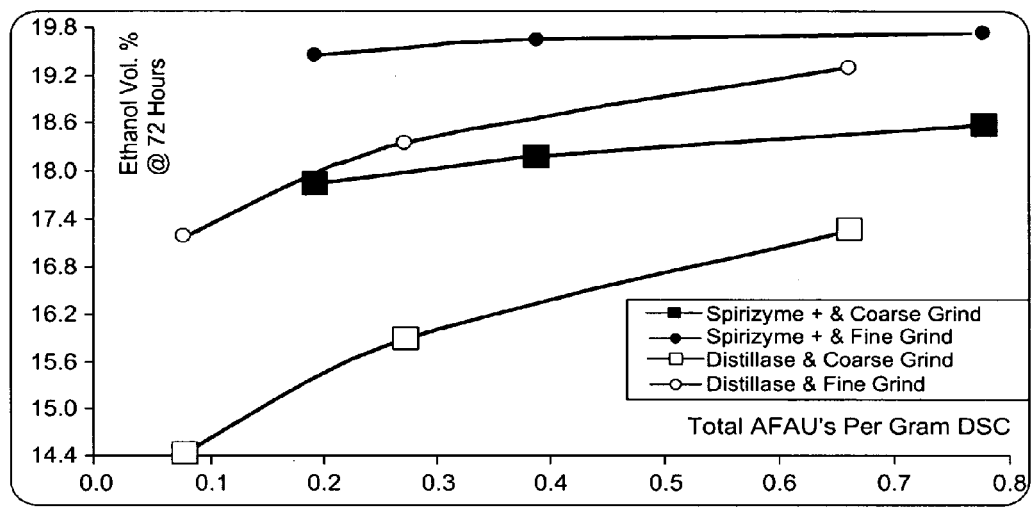
FIGS. 3A-3C schematically illustrate the effect of grind particle size, glucoamylase type, and acid fungal amylase dosage on fermentation efficiency in the present process.
Figure 3B:
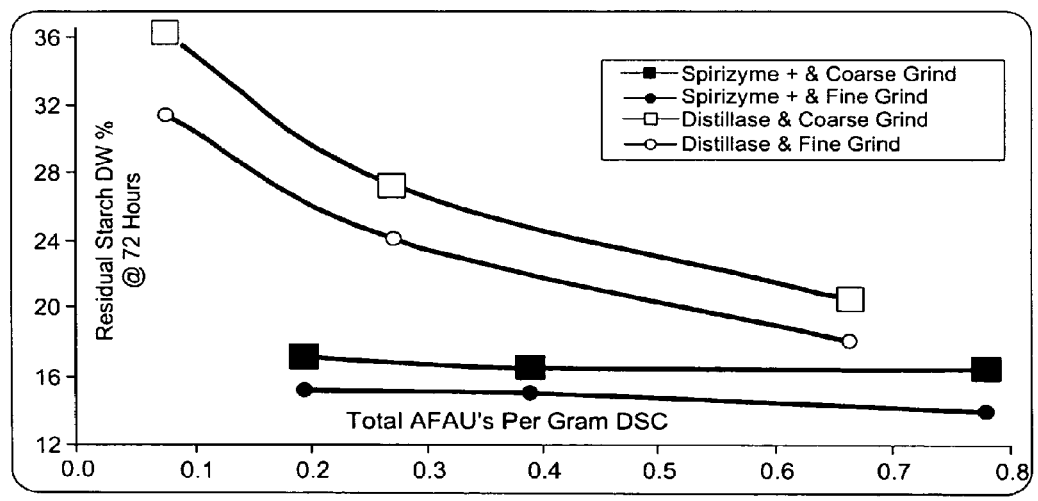
Figure 3C:
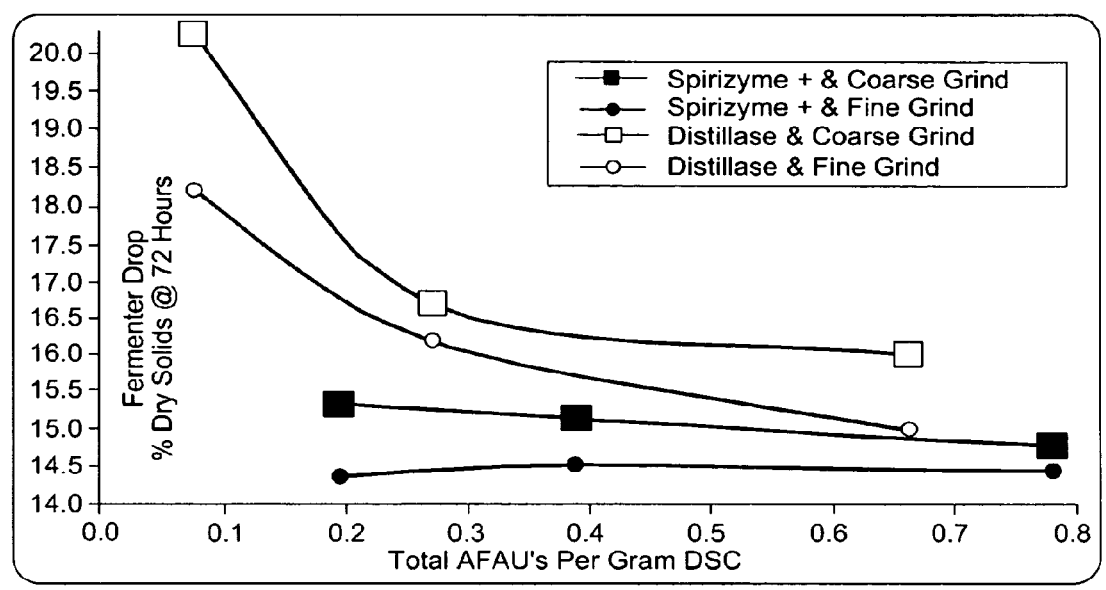

Plant scale dosages refer to 550,000 gallon fermenters with 80 mL lab fermenters used. The grams of flour used and the makeup water added was adjusted for each fermenter to keep the starch content consistent. The pH of all fermenters was adjusted to 6.0 with sulfuric acid. All endosperm flour used was collected from BEI already ground, and all germ flour was ground in the KnifeTech mill (3×10 sec). The whole corn used as control was ground through a Lab 1.0 mm Screen. The pH of all drop samples was adjusted to less than 3.50 with sulfuric acid to deactivate residual enzyme activity prior to drying samples for proximate analysis.
Results and Discussion At the start of fermentation there was a measured difference in the ethanol percentage in the germ produced according to the present method compared to the liquefied germ. This difference continued throughout forty-seven hours of fermentation. A similar trend was observed between the present invention germ meal and the liquefied germ meal. The present process provided improved ethanol kinetics in endosperm fermentation via additional germ or germ meal. These results are illustrated in FIGS. 3A, 3B, and 3C.

Example 11

The Present Process Provides Improved Fermentation Performance

An embodiment of the method of the present invention was evaluated to determine the level of endogenous enzyme activity present in plant material (e.g., corn) slurry during fermentation, as indicated by the amount of glucose and/or FAN measured after 24 hours of fermentation. The present method was found to provide enhanced levels of both glucose and FAN compared to conventional fermentation processes.
Materials and Methods Fermentations were prepared in a similar manner to the description in Example 1.
Results and Discussion Table 7 shows the increase in glucose and FAN concentration as a result of endogenous enzyme activity during fermentation according to an embodiment of the present invention, and in contrast to the decreases in glucose and FAN concentration during conventional fermentation. Table 7 shows the amount of glucose produced by activities of endogenous enzymes on corn slurry from each of 11 corn hybrids, using a process of the present invention. As shown in Table 7, the corn slurries exhibited average increases in glucose concentration of 1.56% w/v after 24 hours. The corn slurries processed by conventional fermentation, by contrast, experienced an average reduction in glucose concentration of 0.42% w/v after 24 hours (bottom of Table 7).

reduces endogenous enzyme activity, resulting in reduced glucose production, ethanol titers, and starch accessability.

Example 12

The Initial Moisture Content of Corn can Affect Ethanol Yields in the Present Process of the Invention The effects of post harvest handling (plant material (e.g., grain) drying and storage) and initial moisture content of corn on ethanol yields of an embodiment of the present invention

TABLE 7

The increase in glucose and FAN concentration as a result of endogenous enzyme activity during fermentation according to an embodiment of the present invention, and in contrast to the decreases in glucose and FAN concentration during conventional fermentation.

| | PRESENT PROCESS | | | | | |
|---|---|---|---|---|---|---|
| Hybrid | Initial T = 0 Hr. Corn Slurry Composition | | Initial T = 24 Hr. Corn Slurry Composition | | Increase in Glucose or FAN due to Endogenous Enzymes | |
| ID # | Gluc % w/v | FAN ppm | Gluc % w/v | FAN ppm | –Gluc ↑ % w/v | –FAN ↑ ppm |
| 1 | 0.46 | 85.2 | 1.77 | 230.5 | 1.31 | 145.3 |
| 2 | 0.51 | 105.6 | 2.46 | 234.5 | 1.95 | 128.9 |
| 3 | 0.48 | 92.4 | 2.66 | 227.5 | 2.18 | 135.1 |
| 4 | 0.63 | 92.8 | 2.68 | 249.5 | 2.05 | 156.7 |
| 5 | 0.53 | 78.0 | 2.15 | 245.5 | 1.62 | 167.5 |
| 6 | 0.50 | 84.0 | 2.31 | 218.0 | 1.81 | 134.0 |
| 7 | 0.36 | 52.4 | 1.69 | 200.0 | 1.33 | 147.6 |
| 8 | 0.48 | 65.6 | 1.57 | 222.0 | 1.09 | 156.4 |
| 9 | 0.74 | 91.0 | 2.23 | 245.0 | 1.50 | 154.0 |
| 10 | 0.52 | 66.2 | 1.53 | 222.5 | 1.01 | 156.3 |
| 11 | 0.57 | 59.2 | 1.89 | 208.5 | 1.32 | 149.3 |
| AVG. | 0.52 | 79.3 | 2.09 | 227.6 | 1.56 | 148.3 |

| | CONVENTIONAL PROCESS | | | | | | |
|---|---|---|---|---|---|---|---|
| Hybrid | Post Liq. 0 Hr. corn Slurry Composition | | Initial T = 24 Hr. Corn Slurry Composition | | Increase in Glucose or FAN due to Endogenous Enzymes | | FAN Lost Due to Maillard Rxns. |
| ID # | Gluc % w/v | FAN ppm | Gluc % w/v | FAN ppm | –Gluc ↑ % w/v | –FAN ↑ ppm | –FAN ↓ ppm |
| 1 | 1.04 | 53.6 | 0.87 | 43.2 | −0.17 | −10.4 | −31.6 |
| 2 | 1.06 | 81.8 | 0.62 | 48.8 | −0.45 | −33.0 | −23.8 |
| 3 | 0.90 | 73.0 | 0.49 | 30.8 | −0.41 | −42.2 | −19.4 |
| 4 | 1.14 | 56.0 | 0.25 | 8.8 | −0.89 | −47.2 | −36.8 |
| 5 | 0.93 | 43.0 | 0.04 | NT | −0.89 | — | −35.0 |
| 6 | 0.87 | 51.2 | 0.32 | 16.0 | −0.55 | −35.2 | −32.8 |
| 7 | 1.03 | 37.4 | 0.60 | 16.6 | −0.44 | −20.8 | −15.0 |
| 8 | 0.86 | 39.6 | 0.64 | 30.0 | −0.22 | −9.6 | −26.0 |
| 9 | 1.14 | 64.0 | 1.01 | 59.6 | −0.13 | −4.4 | −27.0 |
| 10 | 0.82 | 42.8 | 0.55 | 29.0 | −0.27 | −13.8 | −23.4 |
| 11 | 1.02 | 45.8 | 0.76 | 35.4 | −0.26 | −10.4 | −13.4 |
| AVG | 0.98 | 53.5 | 0.56 | 31.8 | −0.42 | −22.7 | |

Similarly, an average increase of 148.3 ppm in FAN concentration was observed after 24 hours in corn slurries processed according to the present invention, while the conventional fermentation process resulted in an average loss of 22.7 ppm in FAN concentration.

Figure 12A:
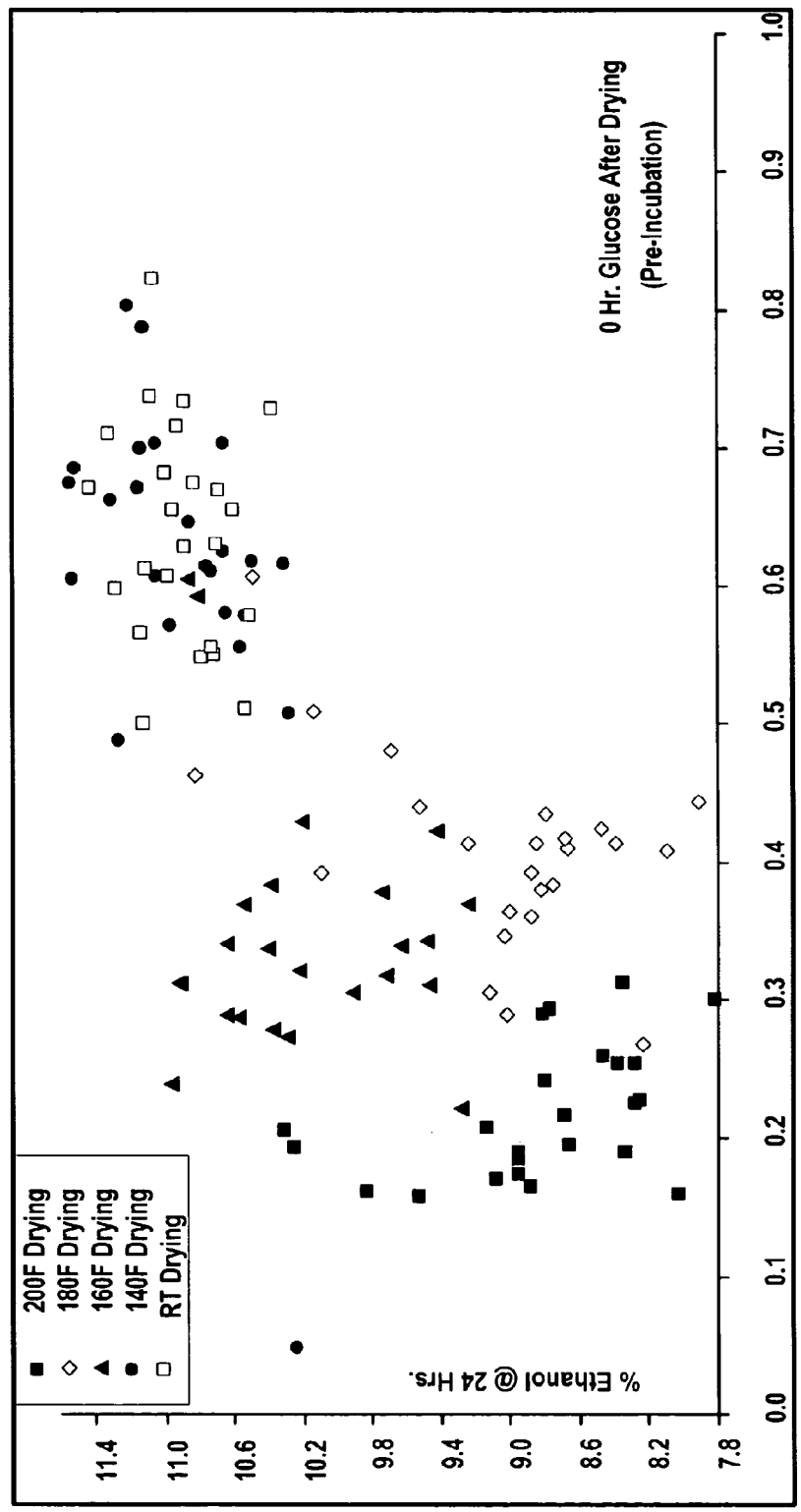
FIGS. 12A, 12B, and 12C illustrate the adverse effects on ethanol yields as a result of high drying temperatures of corn prior to fermentation.
Figure 12B:
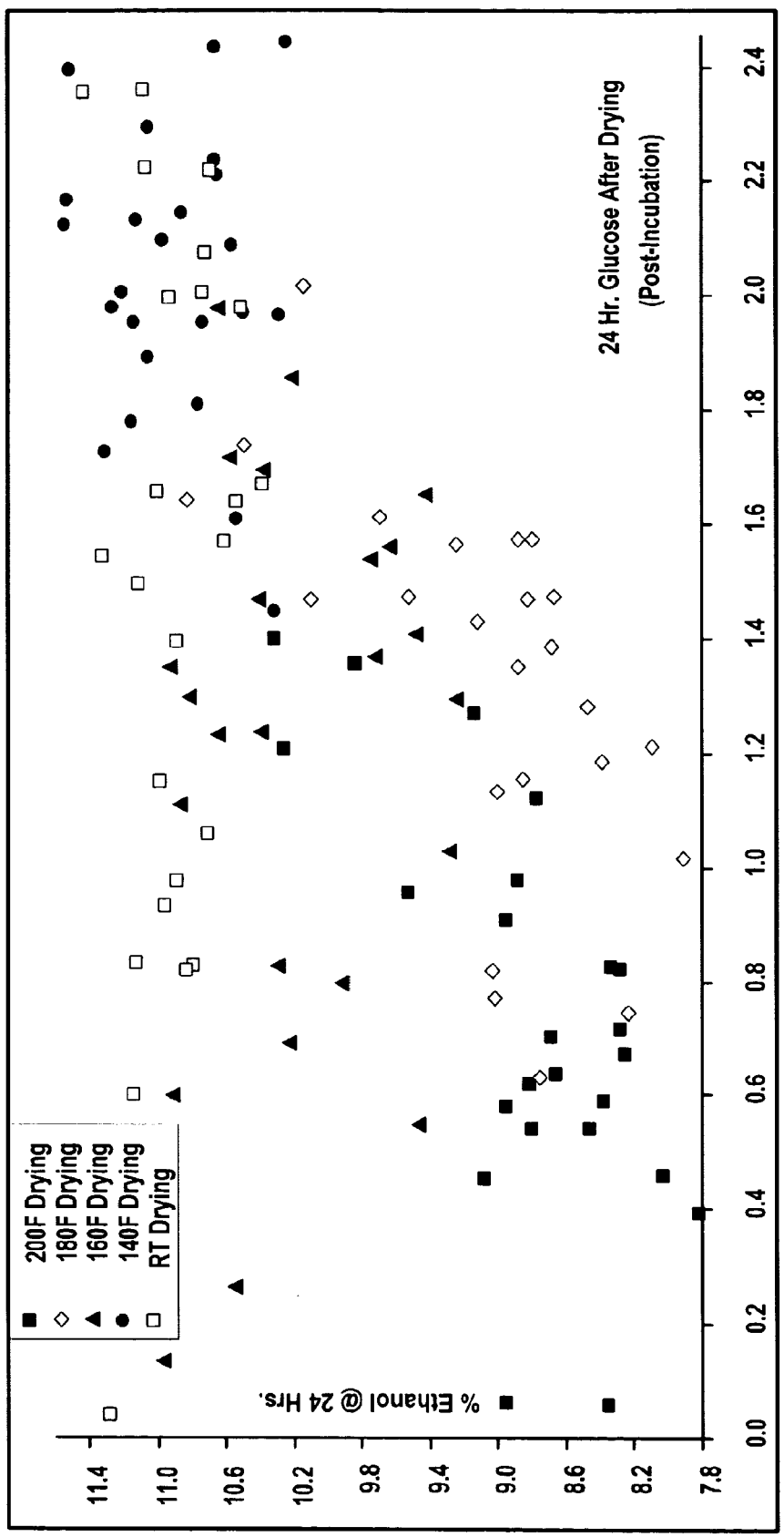
Figure 12C:
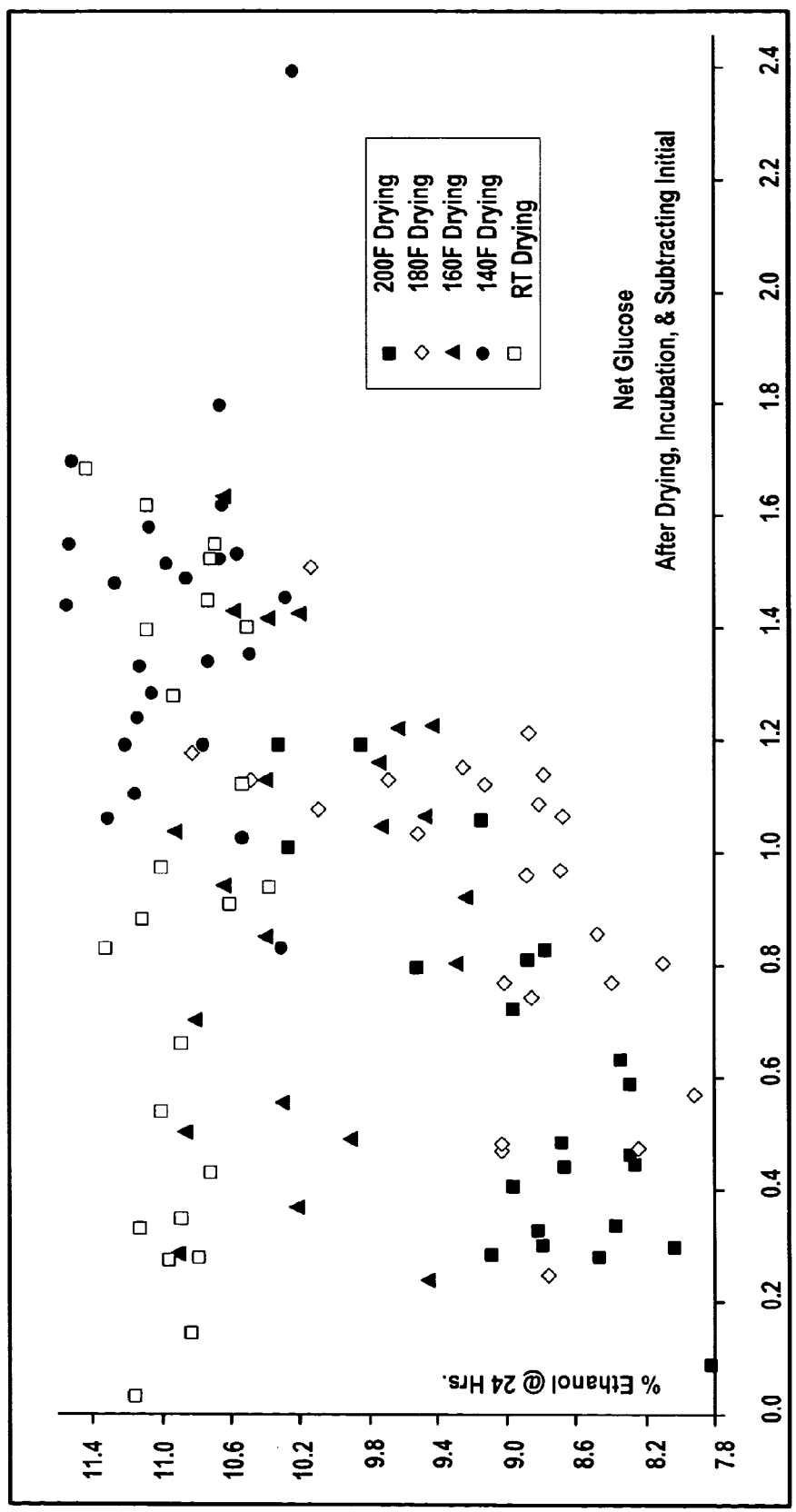

FIGS. 12A-12C depict the yield of ethanol from corn dried at varying temperatures (room temperature, 140, 160, 180 or 200 degrees Fahrenheit), as a function of glucose concentration at: preincubation (FIG. 12A); 24 hours after drying and post-incubation (FIG. 12B); or as a function of net glucose concentration after drying and incubation (FIG. 12C). The results demonstrate that higher glucose concentrations correlated with improved ethanol yields.

As can be seen in FIGS. 12A-12C, higher drying temperatures correlated with lower ethanol yields. Without limiting the invention, it is believed that high temperature drying was explored. It was observed that excess drying temperatures resulted in reduced ethanol yields, and that corn having lower initial moisture content was less affected by changes in the drying temperature.

Materials and Methods

Twenty-four corn hybrids were fermented after drying at varying temperatures. Fermentations were otherwise prepared in a similar manner to the description in Example 1.

Results and Discussion

The effects of post harvest handling (grain drying and storage) and initial moisture content of corn on the present method were evaluated, with the results depicted in FIGS. 13A-13E. Twenty-four corn hybrids were harvested at 25 to 39% initial moisture, and subjected to lab scale drying.

Figure 13A:
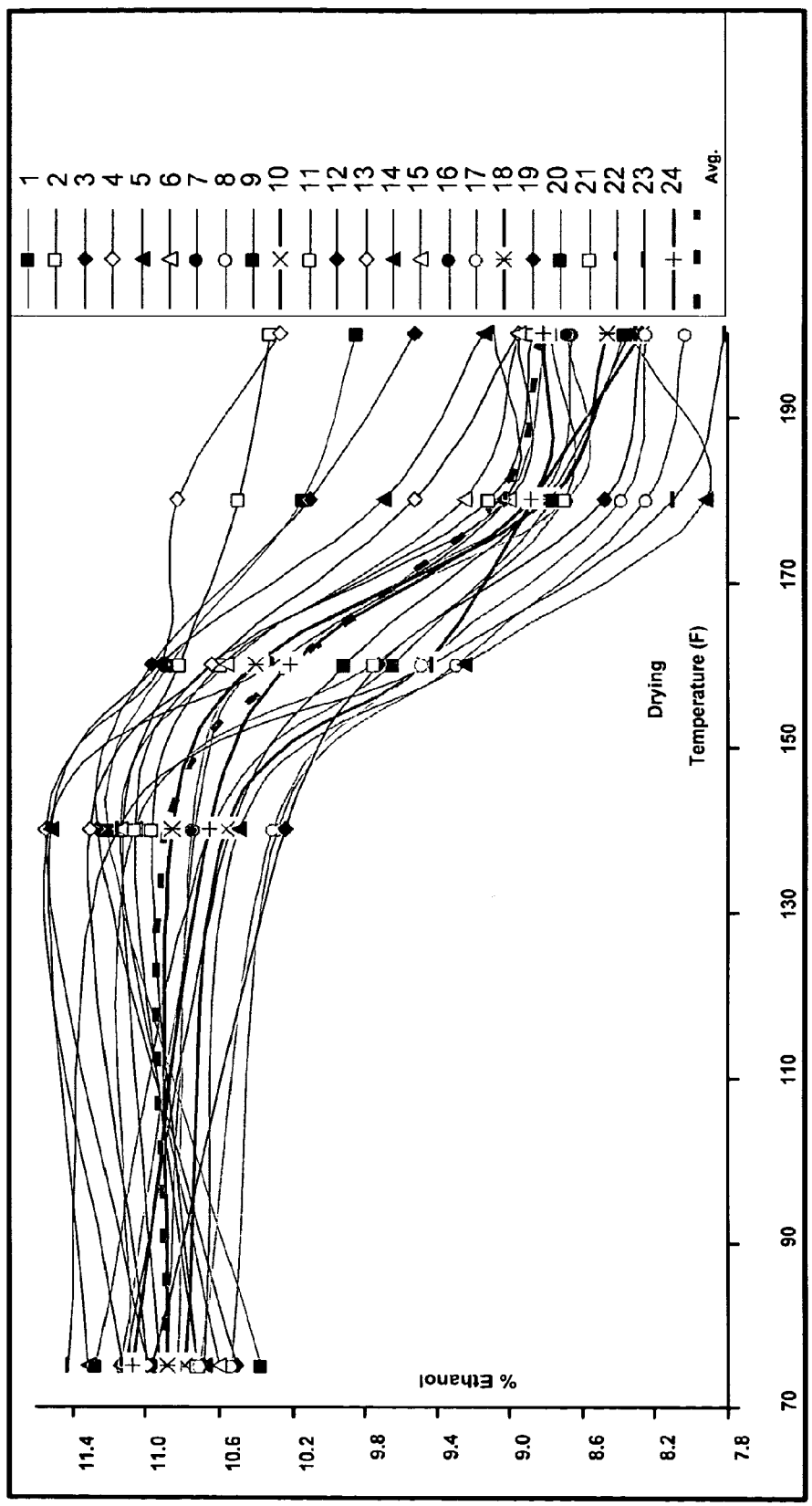

FIGS. 13A-13E demonstrates that post-harvest handling (grain drying and storage) can have an impact on an embodiment of the present method. It was discovered that ethanol yields peaked at a drying temperature of between about 130-150° F. (FIG. 13A). Overall, fermentation of the corn hybrids resulted in a marked loss in ethanol yields when drying temperatures of above approximately 150° F. were used. It was observed that ethanol yields bottomed out at drying temperatures of about 180-200° F. (FIG. 13A).

Figure 13B:
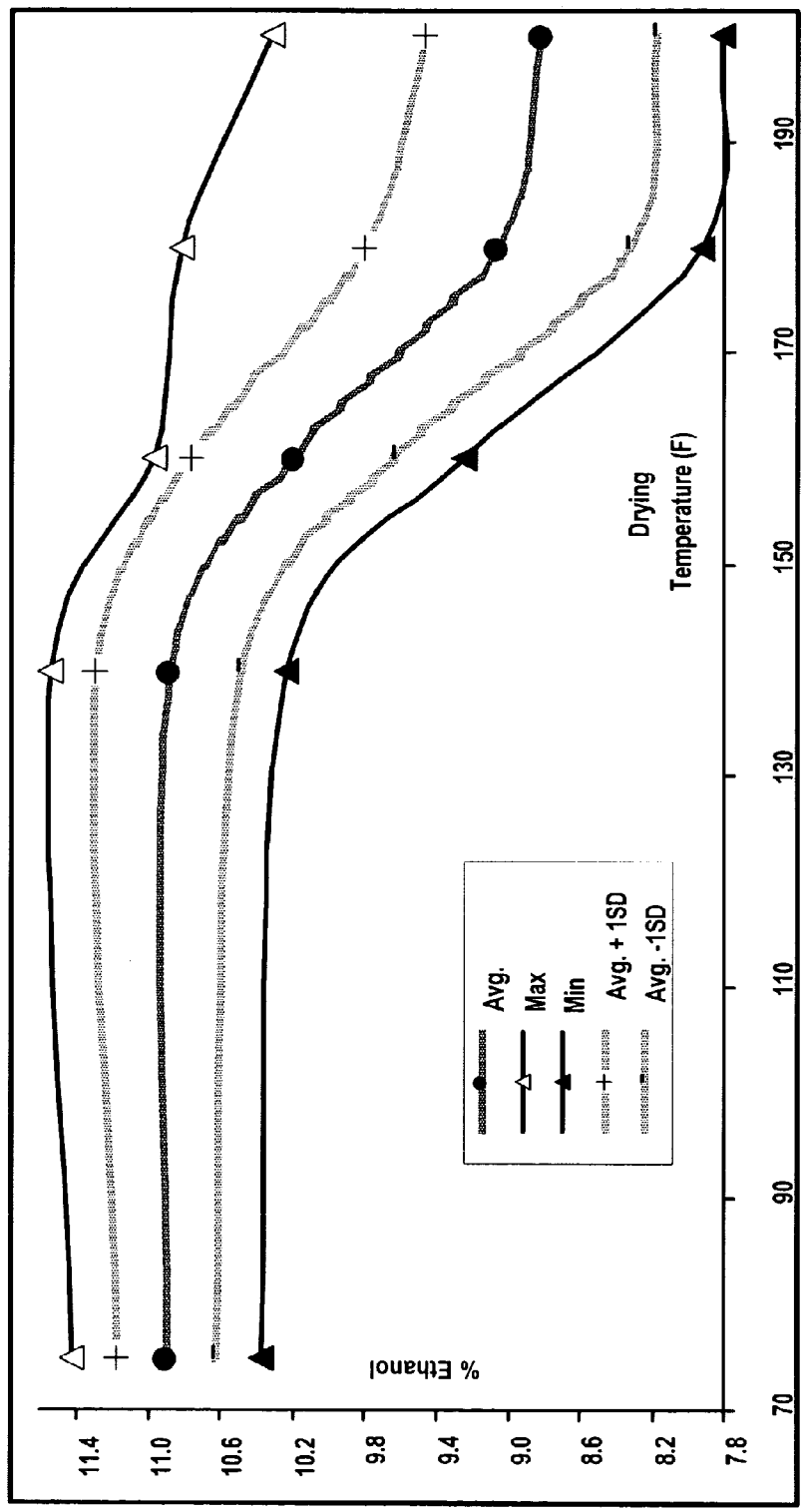

The average ethanol yields of the 24 hybrids, as well as the maximum and minimum yields, are depicted in FIG. 13B. Although not limiting to the present invention, it was observed that the processability (fermentability) of higher temperature dried corn was more variable than lower temperature dried corn (FIG. 13B).

The effect of initial corn moisture content on ethanol yield was also explored. The twenty-four corn hybrids were classified into three groups according to their initial moisture content. The average moisture content of the "high" group was measured at 37%, while the moisture content of the middle group was 33%, and that of the "low" group was 29%.

Figure 13C:
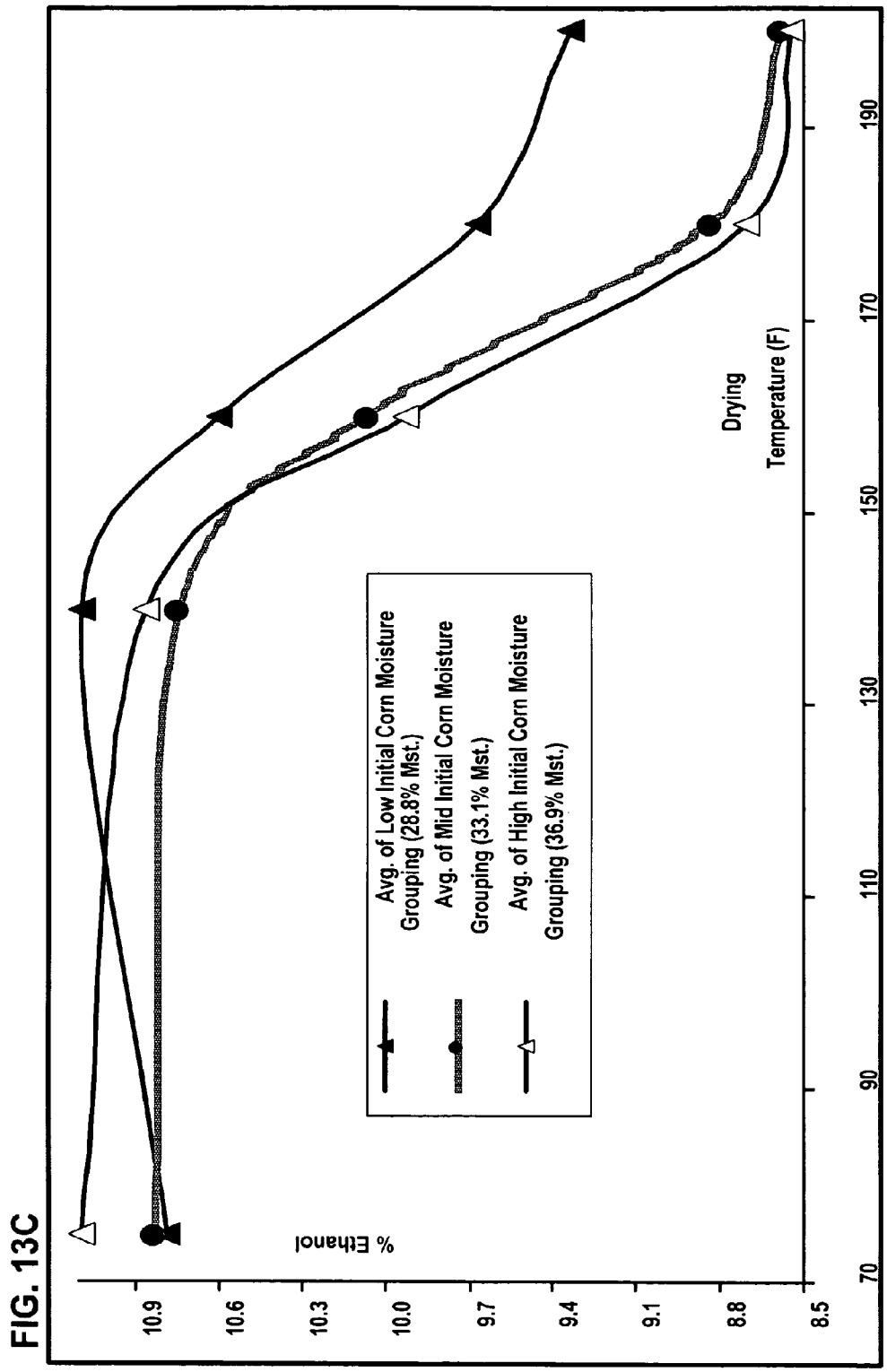

The results are depicted in FIG. 13C. It was observed that hybrids having a lower initial moisture content were more resistant to the impact of drying temperature on ethanol yields (FIG. 13C). Although not limiting to the present invention, it is believed that the lower the initial moisture of the corn, the lower the impact of high temperature drying on the grain.

The effects of increased FAN concentrations on ethanol yield and glycerol production were also evaluated, with the results depicted in FIG. 13D. Ethanol and glycerol formation can be tightly coupled; the higher the ethanol concentration, the greater the glycerol concentration. Glycerol is used to regenerate NADH for continued glycolysis and fermentation. When extra FAN is present, however, such as that generated from endogenous protease, the relationship between glycerol formation and ethanol formation can be decoupled, and it is possible to achieve higher ethanol concentrations without the concomitant increase in glycerol formation (FIG. 13D).

Figure 13E:
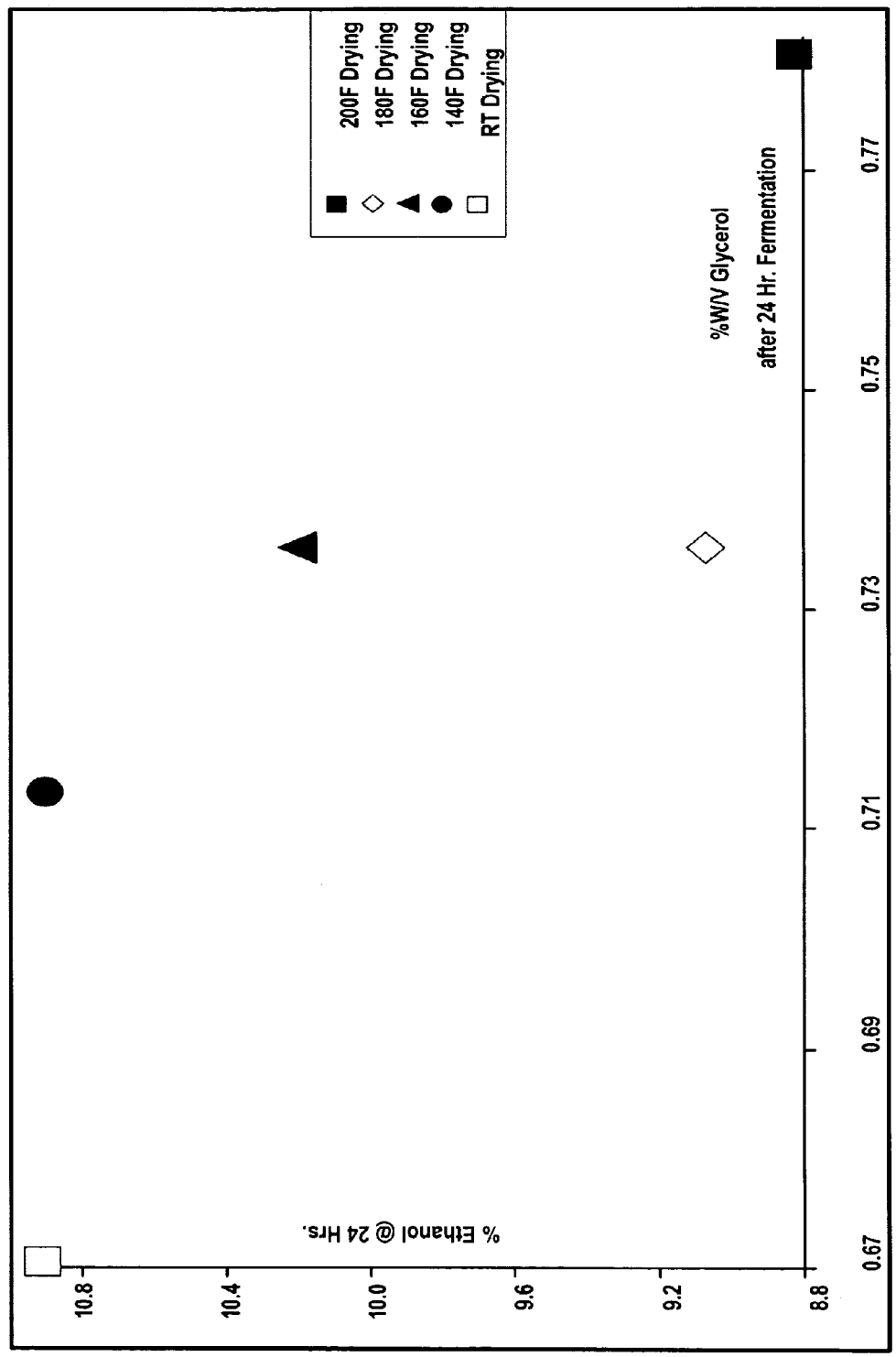

The relationship between ethanol yield, glycerol formation, and drying temperature during processing of corn according to the present invention was also explored. The twenty-four corn hybrids were dried at one of five different temperatures (room temperature, 140, 160, 180, or 200 degrees Fahrenheit). As shown in FIG. 13E, the use of higher drying temperatures correlated with higher glycerol concentration and lower yields of ethanol after 24 hours of fermentation. The maximum ethanol yield and lowest glycerol concentration was obtained from corn dried at room temperature (FIG. 13E). The lowest ethanol yield was obtained from the fermentation of corn that had been dried at the highest temperature of 200 degrees Fahrenheit, and that exhibited the highest amounts of glycerol (FIG. 13E).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

I claim:

1. An aqueous corn composition for fermentation comprising:
    An aqueous corn composition for fermentation comprising:
    corn which has been dried at a temperature between about room temperature and about 170 ° F. under conditions such that the activity of endogenous enzymes within the corn is maintained; and
    a fungal acid amylase and a glucoamylase wherein the aqueous composition is maintained at a pH of 3 to 6;
    wherein the corn has a particle size such that at least about 50% of the particles fit through a sieve with a 0.5 mm mesh.

2. The corn composition of claim 1, wherein the corn has been dried at an elevated temperature with a short exposure to higher temperature air to maintain a moisture content of the corn to about 13 wt-%.

3. The corn composition of claim 1, wherein the corn which has been dried at a temperature that does not exceed about 160° F.

4. The corn composition of claim 1, wherein the corn which has been dried at a temperature that does not exceed about 140° F.

5. The corn composition of claim 1, wherein the corn comprises corn endosperm.

6. The corn composition of claim 1, wherein the corn comprises waxy corn or high protein corn.

7. The corn composition of claim 1, comprising about 0.1 to about 10 acid fungal amylase units per gram of dry solids of corn and about 0.1 to about 6 glucoamylase units per gram of dry solids of corn.

* * * * *